US008485419B2

(12) United States Patent
Gaynor et al.

(10) Patent No.: US 8,485,419 B2
(45) Date of Patent: *Jul. 16, 2013

(54) FLEXIBLE MULTI-PANEL STERILIZATION ASSEMBLY

(75) Inventors: Melissa R. Gaynor, Roswell, GA (US); Laureen C. Clark, Johns Creek, GA (US); Steven Scott Friderich, Roswell, GA (US); Alice Susan Gordon, Roswell, GA (US); Brian L. Gustin, Canton, GA (US); Shawn E. Jenkins, Duluth, GA (US); Corinna Schwarz, Roswell, GA (US); Tara Denise Smith, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/560,368

(22) Filed: Jul. 27, 2012

(65) Prior Publication Data
US 2013/0020380 A1    Jan. 24, 2013

Related U.S. Application Data

(63) Continuation of application No. 12/850,697, filed on Aug. 5, 2010, now Pat. No. 8,261,963.

(51) Int. Cl.
*B65D 65/00*  (2006.01)
*A61L 2/00*   (2006.01)

(52) U.S. Cl.
USPC ........................................ 229/87.01; 422/294

(58) Field of Classification Search
USPC ........................................ 229/87.01; 422/294
See application file for complete search history.

(56) References Cited

U.S. PATENT DOCUMENTS

| 2,997,166 | A | 8/1961 | Pratt |
| 3,107,786 | A | 10/1963 | Adelman |
| 3,409,121 | A | 11/1968 | Michael |
| 3,616,114 | A | 10/1971 | Hamaguchi et al. |
| 3,680,772 | A | 8/1972 | Hoover |
| 3,746,152 | A | 7/1973 | Allen |
| 4,020,842 | A | 5/1977 | Richman et al. |
| 4,241,828 | A | 12/1980 | Bourdelle et al. |
| 4,342,392 | A | 8/1982 | Cox |

(Continued)

FOREIGN PATENT DOCUMENTS

| EP | 0 754 796 A1 | 1/1997 |
| EP | 1 760 130 A2 | 3/2007 |

(Continued)

*Primary Examiner* — Jes F Pascua
(74) *Attorney, Agent, or Firm* — Karl V. Sidor

(57) ABSTRACT

A multi-panel sterilization assembly includes a barrier panel formed of a permeable material, a fold protection panel, and at least one panel attachment means. The barrier panel has a first end, an opposed second end, and a midpoint delineating the barrier panel into a content receiving region and a content covering region. Panel attachment means are located at or near edges of the barrier panel to identify the content receiving region. The fold protection panel has a proximal end and an opposed distal end. After the barrier panel is folded at or near the midpoint to bring its second end near its first end and its edges are brought together and secured by the panel attachment means to form a package, the fold protection panel folds at or near a pre-determined fold line to cover at least a portion of the edges of the folded barrier panel.

16 Claims, 32 Drawing Sheets

U.S. PATENT DOCUMENTS

| | | | |
|---|---|---|---|
| 4,801,480 A | 1/1989 | Panza et al. | |
| 4,887,615 A | 12/1989 | Taylor | |
| 5,035,687 A | 7/1991 | Sandbank | |
| 5,462,540 A | 10/1995 | Caldwell | |
| 5,510,161 A | 4/1996 | Lloyd | |
| 5,922,428 A | 7/1999 | Pufahl | |
| 6,406,674 B1 | 6/2002 | Bourne et al. | |
| 6,578,348 B1 | 6/2003 | Banks | |
| 6,656,171 B1 | 12/2003 | Matsuda et al. | |
| 6,866,928 B2 | 3/2005 | Narum et al. | |
| 8,261,963 B2 * | 9/2012 | Gaynor et al. | 229/87.01 |
| 2006/0104857 A1 | 5/2006 | Pigott et al. | |
| 2007/0095699 A1 | 5/2007 | Frieze et al. | |
| 2007/0128094 A1 | 6/2007 | Paris Jolly et al. | |
| 2008/0253947 A2 | 10/2008 | Davis | |
| 2010/0021671 A1 | 1/2010 | Tu | |
| 2010/0262061 A1 | 10/2010 | Fitzgerald et al. | |

FOREIGN PATENT DOCUMENTS

| | | |
|---|---|---|
| JP | 2000-265132 A | 9/2000 |
| WO | WO 94/16884 A1 | 8/1994 |
| WO | WO 2004/048665 A2 | 6/2004 |
| WO | WO 2005/037333 A1 | 4/2005 |
| WO | WO 2005/066406 A1 | 7/2005 |
| WO | WO 2006/038978 A1 | 4/2006 |
| WO | WO 2006/055083 A1 | 5/2006 |
| WO | WO 2007/018645 A1 | 2/2007 |
| WO | WO 2008/083426 A1 | 7/2008 |
| WO | WO 2008/108135 A1 | 9/2008 |
| WO | WO 2009/143551 A1 | 12/2009 |
| WO | WO 2010/042847 A1 | 4/2010 |

* cited by examiner

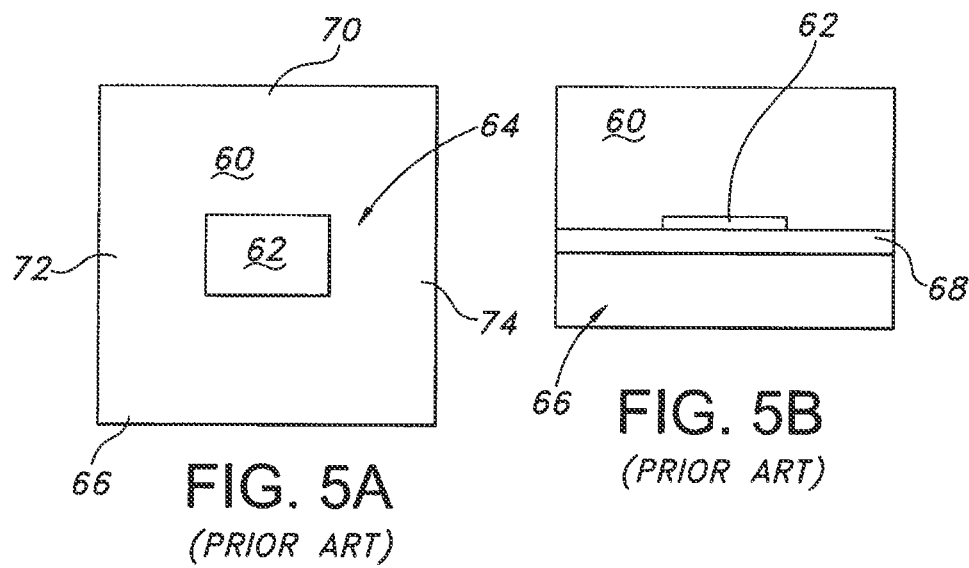
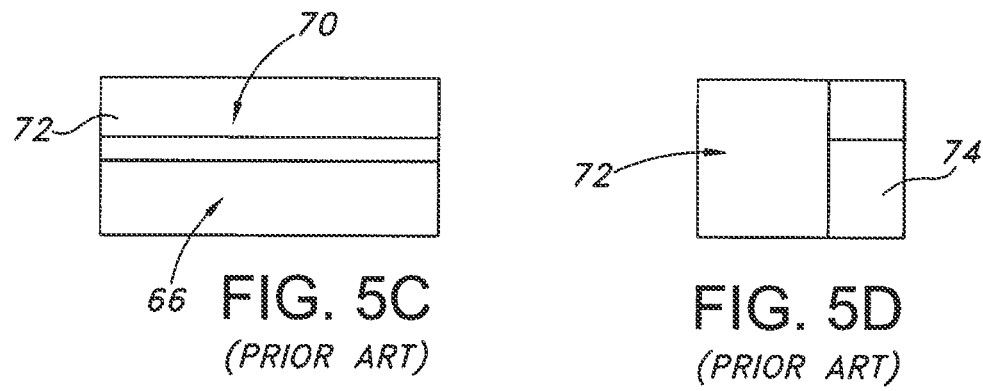
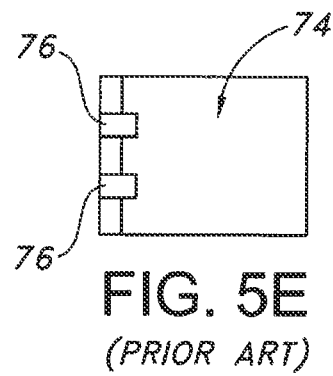

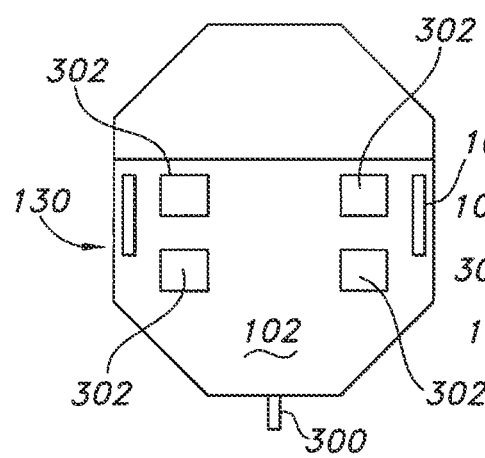
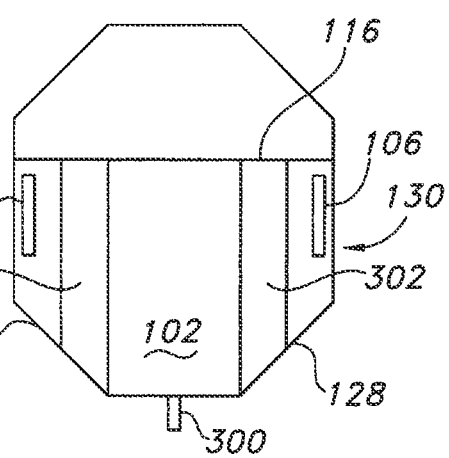
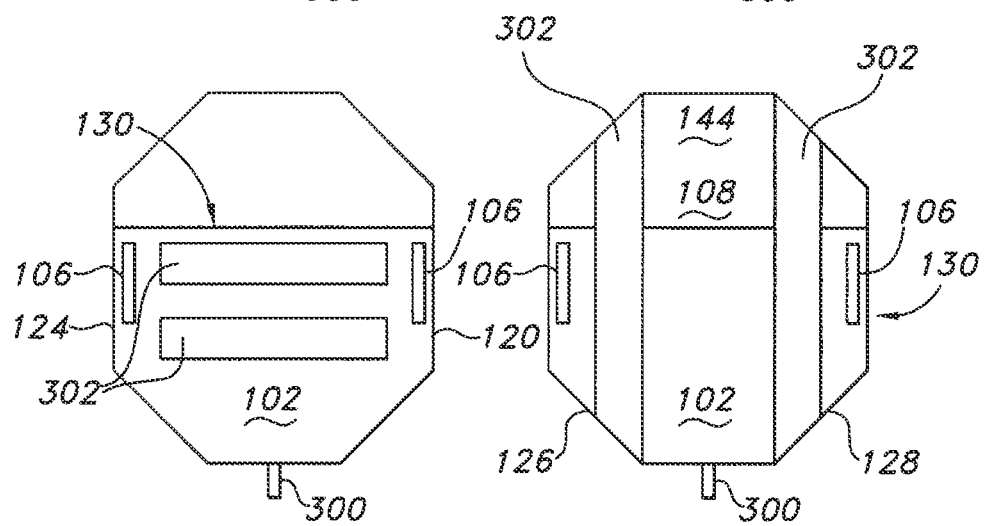
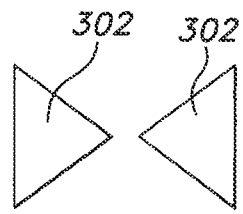
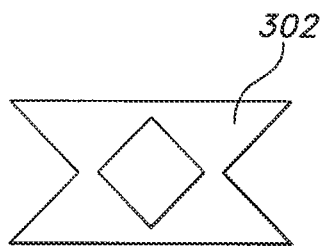

FLEXIBLE MULTI-PANEL STERILIZATION ASSEMBLY

This application is a continuation of U.S. Ser. No. 12/850,697 entitled "Flexible Multi-Panel Sterilization Assembly" by Melissa R. Gaynor et al., filed Aug. 5, 2010 (now U.S. Pat. No. 8,261,963), which is hereby incorporated by reference herein for all purposes.

FIELD OF THE INVENTION

The present invention relates in general to disposable wraps used to contain content to be sterilized and store that content aseptically until use.

BACKGROUND OF THE INVENTION

A variety of products such as gowns, sheets, drapes, instruments, etc. which are required during surgery or other aseptic procedures, are used on a daily basis in the normal operation of hospitals, clinics and the like. Where such products are not pre-packaged in a sterile state, it is necessary for the hospital or clinic to sterilize them before use. Furthermore, where these products are not disposable, and are employed more than once, it is necessary that they be cleaned and otherwise prepared for subsequent use. Prior to such use, however, it is essential that such products be sterilized.

Due to the volume of materials involved, it is often necessary to sterilize and store these products for later use. Accordingly, there has been developed a procedure where such products, after cleaning, laundering and the like, are wrapped in sterilization fabric and then sterilized and stored for subsequent use. Disposable sterilization fabric is typically cut into predetermined rectangular shapes and sold as sterilization wraps.

Traditional wrapping of a sterilization tray or similar articles in a conventional disposable sterilization wrap often involves a large amount of redundant material as excess corners and overlapping plies are gathered, folded, and secured together at the top of the sterilization tray.

Conventional disposable sterilization wrap is a flat, featureless sheet of material that may occasionally contain one or more additional layers of material for strength or absorbency. This flat, featureless configuration provides no information or guidance to a person wrapping an article with the flat sheet of material on how to wrap an article.

Conventional disposable sterilization wrap is frequently made of inexpensive, relatively impermeable material such as, for example, paper and the like. The properties of these materials have generally influenced folding techniques and wrapping configurations to ensure the sterility of the wrapped tray or article.

For example, U.S. Pat. No. 5,635,134 to Bourne, et al. discloses a multi-ply sterilization wrap which is formed by joining one or more sheets of sterilization wrap (e.g., two separate sheets or one sheet folded over) together to form two similarly sized, superposed panels that allow convenient dual wrapping of an article. As another example, U.S. Patent Application Publication No. 2001/0036519 by Robert T. Bayer discloses a two ply sterilization wrap that is formed of a single sheet of sterilization wrap material which is folded to form two similarly sized, superposed panels that are bonded to each other. As yet another example, U.S. Patent Application Publication No. 2005/0163654 by Stecklein, et al. discloses a sterilization wrap material that has a first main panel and a second panel that is smaller than the main panel. The second panel is superposed and bonded to the central portion of the main panel such that it is contained entirely within the main panel to reinforce the main panel and/or provide additional absorbency.

Generally speaking, in these and other examples, large sheets of conventional disposable sterilization wrap are typically used to create large expanses of overlapping materials using one or two standard fold techniques. Large amounts of materials and multiple folds are used to create a tortuous path (e.g., at least two sharp turns in the same direction) to inhibit passage of airborne bacteria past the edges of the sterilization wrap past the folds in response to changes in air pressure in the volume enclosed by the sterilization wrap. That is, large amounts of material and multiple folds are a conventional technique used to address a "bellows effect" from handling or dropping of wrapped contents that may cause rapid volume and pressure changes that force air out of and back into the wrapped package past the edges and folds of sterilization wrap enclosing the content that has been sterilized. The principle of employing a tortuous path to maintain sterile conditions is sometimes referred to as Louis Pasteur's tortuous path principle or theory.

These conventional techniques and the resulting fold configurations require manipulating excess amount of materials during the wrapping and unwrapping process. It takes experience and a certain level of skill to wrap a tray or similar article quickly and reliably. Because of scheduling and cost pressures, medical equipment needed for some procedures may require immediate turnaround and must be processed, sterilized and available for use within hours of its use in a previous procedure. As turnaround times continue to compress, there is a corresponding increase in the need to wrap an article even more quickly while ensuring the integrity of the wrapping.

Errors during the wrapping of an article prior to sterilization or during the unwrapping of a sterilized article in the operating room have important financial and time consequences. Improperly wrapped packages are more likely to become compromised by aggressive handling or excessive amounts of routine handling. A contaminated article requiring re-sterilization can delay a critical medical procedure. A typical hospital may spend approximately fifty-thousand dollars ($50,000.00 US) annually on sterilization wrap, sterilization pouches or sterilization containers. Failure of the sterilization wrap, pouch or container, and/or errors related to wrapping or unwrapping will require re-sterilization of the contents if another sterilized substitute is not immediately available. If there is any doubt about the sterility of any item, it must be re-sterilized. Depending on the procedure, it may cost up to eight-thousand dollars ($8,000.00) to reschedule a single medical procedure. Thus, the cost of only a few negative events may add up to a significant portion of what is spent on sterilization wraps, pouches, or containers.

There are many ways items conventionally wrapped or packaged in sterilization wraps can be contaminated. For example, soil, moisture, and bacteria can be forced into the package by incorrect or excessive handling, poor storage facilities, or improper techniques. As noted above, an aerosol or bellows effect always occurs, to some extent, by the squeezing action of the hands each time the package is handled. Dropping a package onto a hard surface such as a floor can also create a bellows effect by rapidly compressing the volume of the package which then recovers some or all of its volume and/or which may allow bacteria to enter the package through ruptured seals or small breaks or tears of the material that are not easily detected. Incorrect opening of the package may compromise the sterility of the contents of the package.

Certain modes of wrap failure such as knife cuts, abrasion and punctures are well-recognized. There are other modes of failure that are as common if not more common. These include pressure cuts, snag cuts and pressure holes.

A pressure cut can appear as a knife cut, but upon closer examination, the fibers around the very edge of the cut have been "welded" or stuck together. The edge of the cut may feel hard to the touch. This type of cut usually follows the perimeter or outline of the bottom of the instrument tray. It may also occur on the top of the instrument tray, if a number of trays have been stacked upon one another. An example of a typical event that may generate a pressure cut would be lifting the front end of a 20 pound tray so that all the weight of the tray is resting on a back edge, and pulling it across the storage shelf before lifting. This is similar to cutting the wrap with scissors; the material is caught between two layers of hard solid interfaces with a shearing action applied to the material.

In a snag cut, the edges of the cut show loose fibers hanging and/or there are individual fibers spanning across the width of the cut. The edges of the cut are not rough or hard, as with the pressure cut. In larger snag cuts, the shape of the cut area resembles a triangle, with the point of the triangle being where the snag began. The snag cut will occur along the edges of the wrapped instrument tray if the tray is very loosely wrapped. Otherwise, this type of cut will occur on the other areas of the tray where the wrap is too loose and can be caught by rough surfaces or corners. This type of cut is generally due to the tray being pulled or dragged across a roughened surface, often an older, well-used sterilizer cart. This cut can also occur when a loosely wrapped area of a tray gets caught on the corners or edges of objects.

A pressure hole may appear to be a tiny opening where the fibers around the very edge of the hole have been "welded" or stuck together. This type of hole is usually found along the perimeter of the bottom of an instrument tray. It may also occur on the top of the instrument tray if a number of trays have been stacked upon it. An example of a typical event that may generate a pressure hole would be a tray being dropped (even a small distance) onto an edge of a cart or storage shelf while being transported to different areas of the hospital.

The use of large sheets of conventional disposable sterilization wrap with standard fold techniques provides large expanses of overlapping materials and multiple folds that are also generally thought to help protect against pressure cuts, snag cuts and pressure holes as well as the more commonly recognized modes of failure (i.e., knife cuts, abrasion and punctures). Accordingly, conventional solutions employ larger sheets of material, greater numbers of layers of material, combinations of large sheets of different materials, centrally located reinforcing or absorbent zones, bumpers or pads that are attached to the corners of trays, and combinations thereof—all of which require using and manipulating excessive amounts of material during the wrapping and unwrapping process, adding difficulty that slows the wrapping and unwrapping process, and creating waste.

Accordingly, there is an unmet need for an easy to use assembly, package or system that simplifies the task of wrapping or preparing an article for sterilization. There is also an unmet need for an easy to use package or system that simplifies the task of unwrapping a sterilized article. In addition to these needs, there is also a need for an arrangement, assembly or system of sterilization fabric that reduces or eliminates failures or breaches that compromises the sterility of the contents enclosed by the same. That is, a need exists for an assembly or system of sterilization wrap or fabric that reduces the occurrence of pressure cuts, pressure holes, snag cuts and the like while still reducing the amount of sterilization fabric needed for sterile processing of an instrument tray as well as reducing the complexity, difficulty and/or time required to wrap or cover the instrument tray. There is also an unmet need to reduce the amount of sterilization fabric needed for the sterile processing of an instrument tray.

BRIEF SUMMARY OF THE INVENTION

The problems described above are addressed by the present invention which encompasses a disposable flexible multi-panel sterilization assembly. The disposable flexible multi-panel sterilization assembly includes a barrier panel composed of a permeable sheet material having barrier properties, panel attachment means for securing the barrier panel into a package; and a fold protection panel. The barrier panel includes: a first surface and a second opposing surface; a first end generally defining a pre-determined fold line; a second end opposite the first end; a first edge that is generally perpendicular to the pre-determined fold line; a second edge that is generally opposite the pre-determined fold line; and a third edge that is generally perpendicular to the pre-determined fold line. Desirably, the barrier panel may have a fourth edge that is located generally opposite the pre-determined fold line such that the second edge and the fourth edge form an apex or vertex. More desirably, the barrier panel may have a fourth edge and a fifth edge to define a non-square or non-rectangular shape such that, for example, the fourth edge and a fifth edge generally converge toward the second edge such that the second end of the barrier panel is narrower than the first end of the barrier panel.

The barrier panel may have a width that is the distance from the first edge to the third edge and a length that is the distance from the first end to the second end. According to an aspect of the invention, the barrier panel has a midpoint along the length which spans or runs between the first edge and the third edge to generally delineate the barrier panel into a content receiving region extending from the pre-determined fold line to the midpoint and a content covering region extending from the midpoint to the second edge. According to an aspect of the invention, the surface area of the content receiving region may be from about 25 percent to about 49 percent of the total surface area of the barrier panel. For example, the surface area of the content receiving region may be from about 35 percent to about 45 percent of the total surface area of the barrier panel.

The multi-panel sterilization assembly includes a panel attachment means located between the pre-determined fold line and the midpoint of the barrier panel. The panel attachment means is desirably at or near the first edge or the third edge of the barrier panel. Desirably, the panel attachment means may be at or near both the first edge and the third edge of the barrier panel and may be used to attach the barrier panel to itself after the barrier panel is folded around content to be sterilized to form a package. In an aspect of the invention, the panel attachment means may be located in close proximity to the first edge and the third edge of the barrier panel and/or may extend from the first edge and the third edge of the barrier panel. The panel attachment means may be adhesive tape, double-sided adhesive tape, cleavable release tapes, layered release tapes, cohesive materials, hook and loop fastening systems, mechanical fastening systems including, but not limited to, snaps, clips, magnets, catches, slots and tabs, and combinations thereof. According to an aspect of the invention, the panel attachment means is joined to the barrier panel at a pre-determined position. This pre-determined position may near the pre-determined fold line. The panel attachment means may be configured to identify the barrier panel's content receiving region and further to join the barrier panel's first edge and third edge to each other or to a portion of the content covering region after the barrier panel has been folded at or near its midpoint such that its second end is brought near its first end.

The multi-panel sterilization assembly further includes a fold protection panel in juxtaposed communication with the barrier panel. That is, the fold protection panel desirably extends from the barrier panel. If the fold protection panel is a separate piece of material, it is desirably immediately adjacent the barrier panel in side-by-side relationship. The fold protection panel includes: a proximal end generally adjacent or adjoining the pre-determined fold line; a distal end generally opposite the proximal end; and at least a first edge and a second edge extending from the proximal end to the distal end. According to the present invention, the fold protection panel may have at least a third edge located at or along its distal end. The fold protection panel may be configured so it has barrier properties. For example, the fold protection panel may be formed of the same material as the barrier panel. As another example, the fold protection panel may be formed of the same piece of material as the barrier panel.

In an aspect of the invention, the fold protection panel desirably has a width that is the distance from the first edge to the second edge and a length that is the distance from the proximal end to the distal end, such that, after the barrier panel has been folded at or near the barrier panel's midpoint, the barrier panel's second end is brought near its first end and its first and third edges are joined to each other or to its content covering region to form a package, the fold protection panel is configured to fold at or near the pre-determined fold line to cover at least the first edge and the third edge of the folded barrier panel.

According to the present invention, the barrier panel may be composed of at least one layer of a breathable nonwoven material. Desirably, the breathable nonwoven material is a laminate composed of a layer of spunbonded filaments, a layer of meltblown fibers, and a layer of spunbonded filaments. The permeability of the barrier panel may range from 25 to about 500 cubic feet per minute (CFM) as characterized in terms of Frazier permeability. For example, the permeability of the barrier panel may range from 25 to about 400 cubic feet per minute. As yet another example, the permeability of the barrier panel may range from 25 to about 300 cubic feet per minute.

The sterilization assembly further includes at least one pull tab. The pull tab may be unitary with the barrier panel or it may be attached to the second end of the barrier panel. The pull tab may be formed of the same material as the barrier panel or may be formed of one or more different materials. The pull tab provides a feature that allows a user to unwrap a sterilized article aseptically. That is, a person unwrapping an article that is folded in the flexible multi-panel sterilization assembly may use the pull tab to avoid reaching over the sterile field generally presented from unwrapping and spreading out the sterile content-contacting surface of the barrier panel.

The sterilization assembly may further include one or more discrete reinforcement elements. These elements are desirably in the content receiving region that define an area for receiving content to be sterilized. The reinforcement element(s) may include one or more layers of materials selected from fibrous webs, impermeable films, permeable or porous films, apertured films, foams, foils and combinations thereof.

According to an aspect of the invention, the sterilization assembly may further include indicia or instructions on the sterilization assembly itself to inform the proper folding of the assembly into a package.

In an aspect of the invention, there is provided a disposable flexible multi-panel sterilization assembly that includes a barrier panel formed from a sheet of barrier material (e.g., barrier fabric) having at least one panel edge. The barrier panel is configured to be folded around content to be sterilized to form a package. Barrier panel attachment means are located on a portion of the barrier panel for securing one or more panel edges of the barrier panel in a folded configuration around content to be sterilized. The barrier panel attachment means are configured to secure the one or more panel edges in a folded configuration with substantially greater resistance to shear force than to peel force. The multi-panel sterilization assembly further includes a fold protection panel extending from the barrier panel. The fold protection panel includes a proximal end generally adjacent the barrier panel and a distal end generally opposite the proximal end such that the distal end of the fold protection panel covers the one or more panel edges of the barrier panel after the barrier panel is in the folded configuration.

The barrier panel attachment means are used to attach the barrier panel to itself after the barrier panel is folded around content to be sterilized to form a package. The barrier panel attachment means may be adhesive tape, double-sided adhesive tape, cleavable release tapes, cohesive materials, hook and loop fastening systems, mechanical fastening systems including, but not limited to, snaps, clips, magnets, catches, slots and tabs, and combinations thereof.

Yet another aspect of the invention relates to a disposable flexible multi-panel sterilization assembly that includes a barrier panel formed from a sheet of barrier material (e.g., barrier fabric) having at least one panel edge. The barrier panel is configured to be folded around content to be sterilized to form a package. Barrier panel attachment means are located on a portion of the barrier panel for securing one or more panel edges of the barrier panel in a folded configuration around content to be sterilized. The barrier panel attachment means are configured to secure the one or more panel edges in a folded configuration. The multi-panel sterilization assembly further includes a fold protection panel extending from the barrier panel. The fold protection panel includes a proximal end generally adjacent the barrier panel and a distal end generally opposite the proximal end such that the distal end of the fold protection panel covers the one or more panel edges of the barrier panel after the barrier panel is in the folded configuration and so less than ten (10) stacked plies of material are present as a result of the folding of the sterilization assembly around an article. Desirably, less than five (5) stacked plies of material are present as a result of folding of the sterilization assembly around an article such as a sterilization tray.

Another embodiment of the present invention encompasses a multi-panel sterilization assembly having a barrier panel composed of a permeable sheet material providing barrier properties. The barrier panel includes: a first surface and a second opposing surface; a first end generally defining a pre-determined fold line; a second end opposite the first end; a first edge that is generally perpendicular to the pre-determined fold line; a second edge that is generally parallel to the pre-determined fold line; a third edge that is generally perpendicular to the pre-determined fold line; a fourth edge located between the second edge and the third edge; and, a fifth edge located between the first edge and the second edge. The barrier panel has a first width that is the distance from the first edge to the third edge and second width that is the distance from the fourth edge to the fifth edge; a length that is the distance from the first end to the second end, the barrier panel having a midpoint along the length and extending between the first edge and the third edge or the fourth edge and the fifth edge to generally delineate the barrier panel into a content receiving region extending from the pre-determined fold line to the midpoint and a content covering region extending from the midpoint to the second edge.

The multi-panel sterilization assembly includes at least one pull tab at the second end of the barrier panel; a panel attachment means between the pre-determined fold line and the midpoint of the barrier panel and at or near the first edge or the third edge; the panel attachment means being joined to the barrier panel at a pre-determined position to identify the barrier panel's content receiving region and further to join the barrier panel's first edge and third edge to each other or to a portion of the content covering region after the barrier panel has been folded at or near its midpoint such that its second edge is brought near its first end.

The multi-panel sterilization assembly further includes a fold protection panel in juxtaposed communication with the barrier panel. The fold protection panel includes: a proximal end generally adjacent or adjoining the pre-determined fold line; a distal end generally opposite the proximal end; and at least a first edge and a second edge extending from the proximal end to the distal end, the fold protection panel having a width that is the distance from the first edge to the second edge and a length that is the distance from the proximal end to the distal end, such that, after the barrier panel has been folded at or near its midpoint so its second end is brought near its first end and its first and third edges are joined to each other or to its content covering region to form a package, the fold protection panel is configured to fold at or near the pre-determined fold line to cover at least the first edge and the third edge of the folded barrier panel.

These and other features and advantages of the invention will become more apparent to one skilled in the art from the following description and claims when read in light of the accompanying drawings.

BRIEF DESCRIPTION OF THE DRAWINGS

The present invention will be better understood by reading the Detailed Description of the Invention with reference to the accompanying drawing figures, in which like reference numerals denote similar structure and refer to like elements throughout, and in which:

FIGS. 5A to 5E are illustrations of an exemplary sequence of folding an exemplary prior art sterilization wrap system using a conventional square fold.

FIGS. 10A to 10D are illustrations of exemplary disposable flexible multi-panel sterilization assemblies showing exemplary reinforcing elements.

FIGS. 11A to 11B are illustrations of exemplary reinforcing elements.

DEFINITIONS

Figure 1:
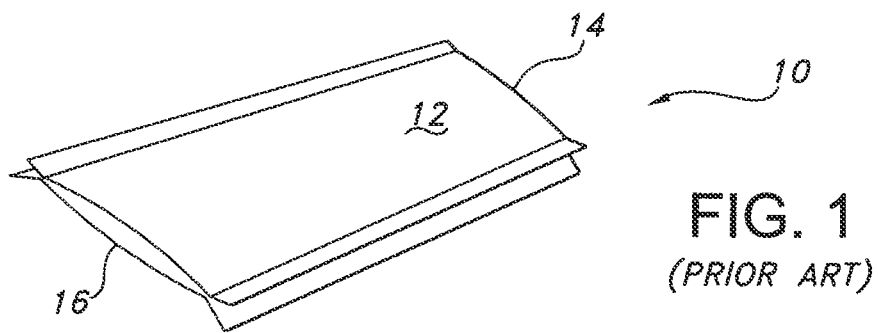
FIG. 1 is an illustration of an exemplary prior art sterilization wrap system.

As used herein, the term "disposable" refers to a product that is so inexpensive that it may economically be discarded after only a single use. Products that are "disposable" are typically intended for single use. The term "single-use" refers to a product that is intended to be used for only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse.

As used herein, the term "sterilization assembly" refers to a flexible article composed of fabric(s) and/or flexible material(s) that is wrapped around, folded around or otherwise encloses a non-sterile article or non-sterile content prior to sterilization. A sterilization assembly has multiple panels and/or sections providing specific physical properties, functional characteristics and/or structure that provide advantages for wrapping or folding, handling, strength, sterilization, storage after sterilization, and/or unwrapping or unfolding.

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing, spunbonding and bonded carded web processes.

As used herein, the term "spunbonded web" refers to a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, the term "meltblown fibers" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers. The meltblown process is well-known and is described in various patents and publications, including NRL Report 4364, "Manufacture of Super-Fine Organic Fibers" by V. A. Wendt, E. L. Boone, and C. D. Fluharty; NRL Report 5265, "An Improved device for the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al.

As used herein, "ultrasonic bonding" means a process performed, for example, by passing the fabric between a sonic horn and anvil roll as illustrated in U.S. Pat. No. 4,374,888 to Bornslaeger, the entire contents of which is incorporated herein by reference.

As used herein "point bonding" means bonding one or more layers of fabric at a plurality of discrete bond points. For example, thermal point bonding generally involves passing a fabric or web of fibers to be bonded between a heated roll assembly such as, for example, a heated calender roll and an anvil roll. The calender roll is usually patterned in some way so that the entire fabric is not bonded across its entire surface, and the anvil roll is usually smooth. As a result, various patterns for calender rolls have been developed for functional and/or aesthetic reasons. One example of a pattern has points and is the Hansen Pennings or "H&P" pattern with about a 30% bond area with about 200 bonds/square inch (31 bonds/square cm) as taught in U.S. Pat. No. 3,855,046 to Hansen and Pennings. Another example is shown in U.S. Design Pat. No. 239,566 to Vogt. Typically, the percent bonding area varies from around 5% to around 30% of the area of the fabric laminate web. Spot bonding holds the laminate layers together as well as imparts integrity to each individual layer by bonding filaments and/or fibers within each layer without destroying the breathability or hand of the fabric.

DETAILED DESCRIPTION OF INVENTION

In describing the various embodiments of the present invention, as illustrated in the figures and/or described herein, specific terminology is employed for the sake of clarity. The invention, however, is not intended to be limited to the specific terminology so selected, and it is to be understood that each specific element includes all technical equivalents that operate in a similar manner to accomplish similar functions.

Referring now to FIG. 1, there is shown an exemplary conventional disposable sterilization wrap 10 having a multiple-ply configuration which is formed by joining one or more sheets 12 of sterilization wrap together to form two similarly sized, superposed panels 14 and 16 that allow convenient dual wrapping of an article. While one sheet may be folded back on itself to provide the multiple-ply configuration, two separate sheets are more typically used.

Figure 2:
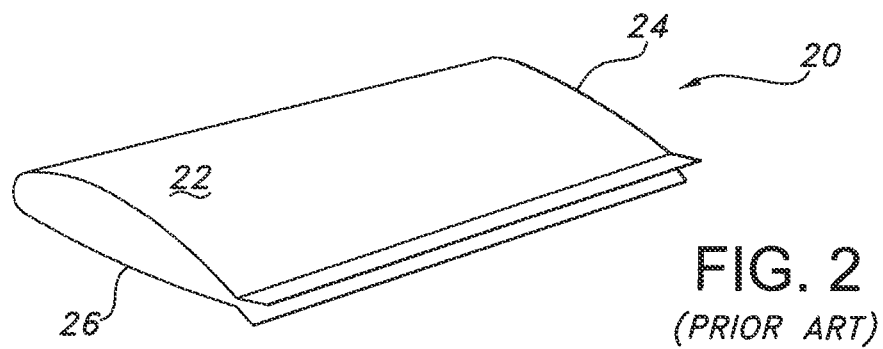
FIG. 2 is an illustration of an exemplary prior art sterilization wrap system.

FIG. 2 is an illustration of an exemplary conventional disposable sterilization wrap 20 as generally disclosed in U.S. Patent Application Publication No. 2001/0036519 by Robert T. Bayer. The conventional disposable sterilization wrap 20 is a two ply sterilization wrap formed of a single sheet 22 of sterilization wrap material which is folded to form two similarly sized, superposed panels 24 and 26 that are bonded to each other.

Figure 3:
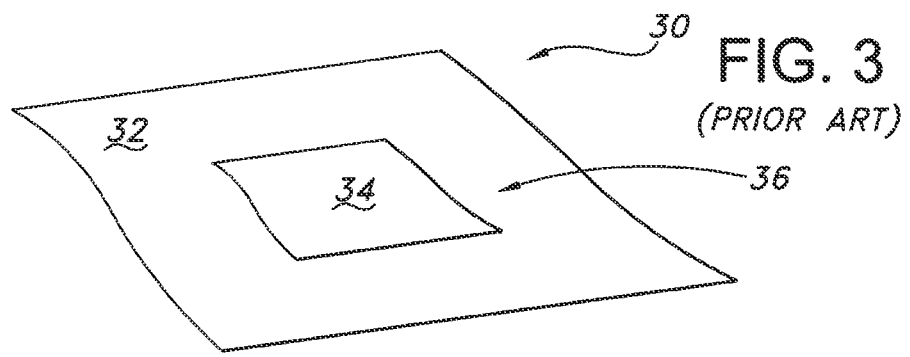
FIG. 3 is an illustration of an exemplary prior art sterilization wrap system.

FIG. 3 is an illustration of yet another example of a conventional disposable sterilization wrap 30 as generally disclosed in U.S. Patent Application Publication No. 2005/0163654 by Stecklein, et al. The conventional disposable sterilization wrap 30 has a first main panel 32 and a second panel 34 that is much smaller than the main panel 32. The second panel 34 is superposed and bonded to the central portion 36 of the main panel 32 to reinforce the main panel 32 and/or provide additional absorbency.

Generally speaking, in these and other examples, large sheets of conventional disposable sterilization wrap are typically used to create large expanses of overlapping materials using one or two standard fold techniques. These standard techniques and the resulting fold configurations require manipulating excess amount of materials during the wrapping and unwrapping process. It takes experience and a minimum level of skill to reliably wrap a tray or similar article quickly.

Figures 4A, 4B:
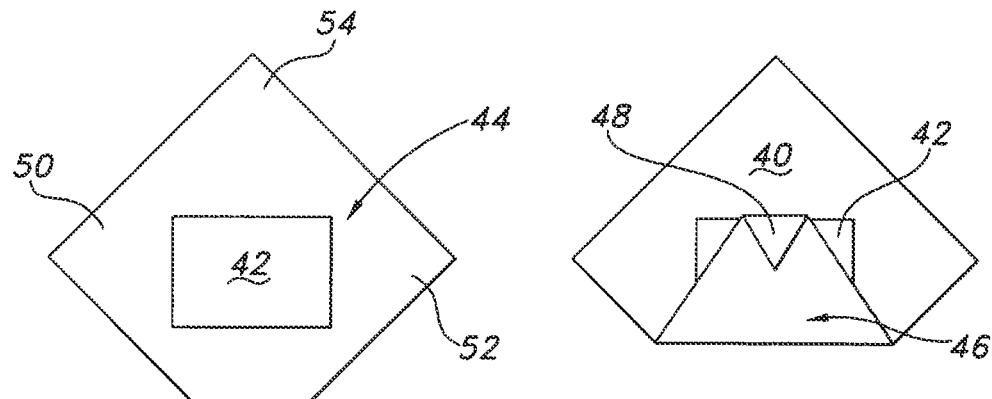
FIGS. 4A to 4E are illustrations of an exemplary sequence of folding an exemplary prior art sterilization wrap system using a conventional envelope fold.
Figures 4C, 4D:
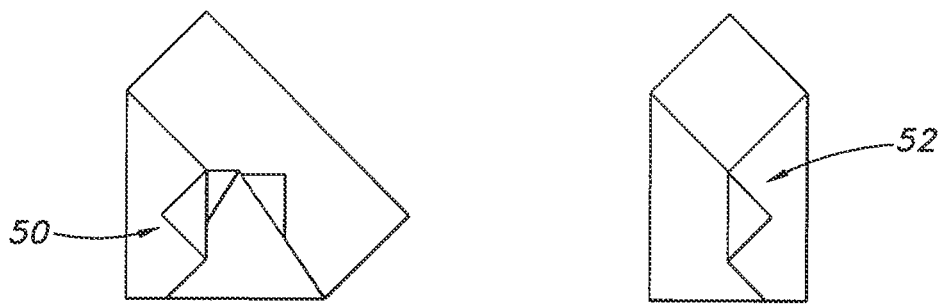
Figure 4E:
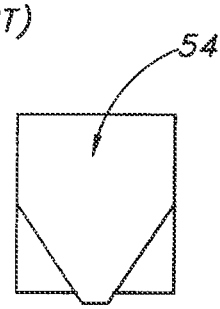

FIGS. 4A through 4E illustrate an exemplary sequence of steps in wrapping an article utilizing a conventional sterilization wrap. As illustrated in FIG. 4A, a square or generally rectangular wrap 40 is spread out flat and an article 42 to be wrapped is placed in a central region 44 of the wrap 40 in a generally diagonal relationship to the orientation of the wrap 40 in a pattern conventionally referred to as an envelope fold. Referring to FIG. 4B, a first end 46 of the wrap is folded up at the base of the article 42 and brought over the article 42. Generally speaking, the sterilization wrap must be sufficiently large in area to provide enough material to substantially cover the article in the initial fold. The first folded end 46 is back-folded to create a small tail 48. This sequence is generally repeated for the remaining second end 50 and the third end 52. Again, the sterilization wrap must be sufficiently sized in area to provide enough material for the second end 50 and the third end 52 to substantially overlap such that the entire or substantially the entire second end 50 is covered by the third end 52. The fourth end 54 is folded over and taped to form a wrapped package.

FIGS. 5A through 5E illustrate an exemplary sequence of steps in wrapping an article utilizing a conventional sterilization wrap. As illustrated in FIG. 5A, a square or generally rectangular wrap 60 is spread out flat and an article 62 to be wrapped is placed in a central region 64 of the wrap 60 in a generally parallel relationship to the orientation of the wrap 60 in a pattern conventionally referred to as a square fold. Referring to FIG. 5B, a bottom end 66 of the wrap is folded up at the base of the article 62 and brought over the article 62. Generally speaking, the sterilization wrap must be sufficiently large in area to provide enough material to substantially cover the article in the initial fold. The folded bottom end 66 is back-folded to create a small tail 68. This sequence is generally repeated for the remaining top end 70 and the left side end 72. Again, the sterilization wrap must be sufficiently sized in area to provide enough material for the top end 70 and the left side end 72 to substantially overlap such that the entire or substantially the entire bottom end 70 is covered by the left side end 72. The right side end 74 is folded over and taped 76 to form a wrapped package.

A typical sterilization tray with the dimensions of 10 inches (25.4 cm) by 20 inches (50.8 cm) by 5 inches tall (12.7 cm) typically requires a square piece of sterilization fabric having each side measuring 45 inches for wrapping and sterile processing. This large size piece is needed so that the corner of the fabric can be folded all the way across the top of the tray with some additional excess material so that the preparer of the tray feels confident that the contents are covered and that the piece of fabric will stay down and not spring back. Using a 45 inch square piece of fabric means that 2025 square inches of material (approximately 13,064 square centimeters) is being used to enclose a tray with a surface area of just 700 square inches (approximately 4,516 square centimeters). In other words, this traditional method requires almost three square inches of material to cover every square inch of a tray of surgical instruments.

Figure 6:
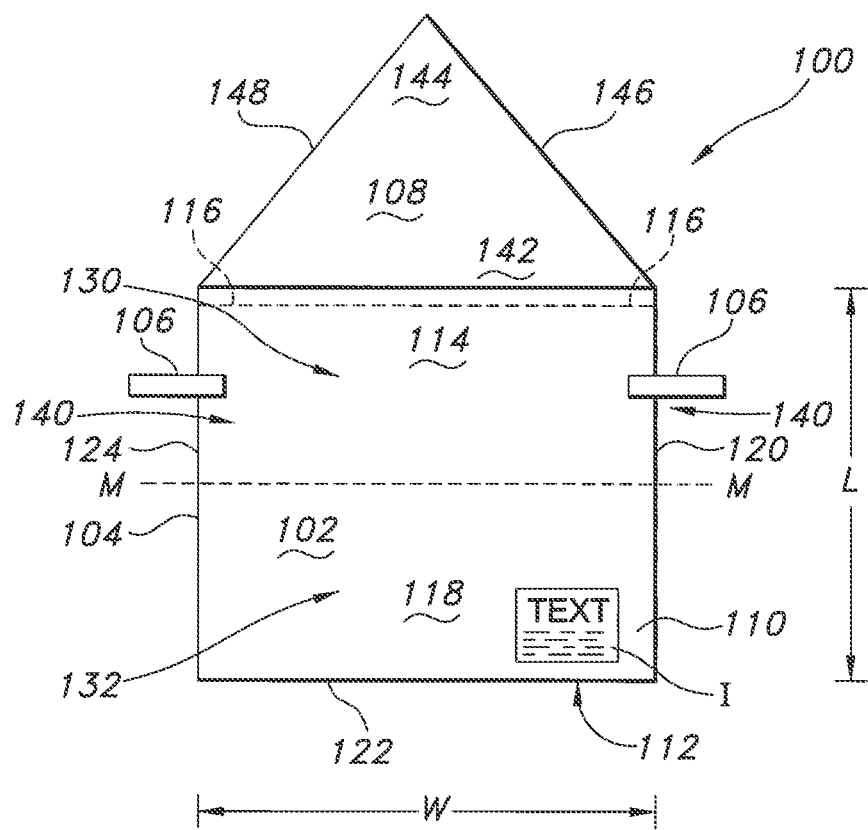
FIG. 6 is an illustration of an exemplary disposable flexible multi-panel sterilization assembly.

The present invention encompasses a disposable multi-panel sterilization assembly which addresses the problems generally described above. An exemplary multi-panel sterilization assembly 100 is illustrated in FIG. 6.

The multi-panel sterilization assembly includes a barrier panel 102 composed of a permeable sheet material 104 having barrier properties (e.g., a barrier fabric), panel attachment means 106 for securing the barrier panel 102 into a package; and a fold protection panel 108. Generally speaking, the "barrier panel" is the portion of a multi-panel sterilization assembly that is formed from a material that is sufficiently permeable to permit a sterilizing gas to pass through it to effect sterilization and has barrier properties sufficient maintain that content in an aseptic condition after sterilization. A barrier panel should also be sufficiently flexible or conformable to that it is configured to receive and subsequently enfold or enclose content to be sterilized thereby forming a package. Generally speaking, the barrier panel may be a barrier fabric. The "fold protection panel" is the portion of a multi-panel sterilization assembly that is formed from a material covers and protects at least a portion of the folded edges of the barrier panel. The fold protection panel is the last panel or part of the multi-panel sterilization assembly that is folded or wrapped around the package formed by the barrier panel around content to be sterilized and the first part of the multi-panel sterilization assembly that is unfolded or unwrapped.

The barrier panel includes: a first surface 110 and a second opposing surface 112; a first end 114 generally adjacent or adjoining a pre-determined fold line 116; a second end 118 opposite the first end 114; a first edge 120 that is generally perpendicular to the pre-determined fold line 116; a second edge 122 that is generally opposite the pre-determined fold line 116; and a third edge 124 that is generally perpendicular to the pre-determined fold line 116. The "pre-determined fold line" is a line or region generally defined by the first end 114 of the barrier panel. Generally speaking, the predetermined fold line is offset from the boundary or transition between the barrier panel and the fold protection panel towards the center or midpoint of barrier panel 102. The pre-determined fold line 116 identifies the desired location for placing the content to be sterilized at the first end 114 of the barrier panel 102. The offset serves to provide a sufficient amount of barrier panel that the content to be sterilized is fully surrounded by the barrier panel after folding is complete. The pre-determined fold line 116 may be offset from the boundary or transition by about 0.5 inch (~13 mm) to about 2 inches (~51 mm). Desirably, the pre-determined fold line is offset by about 1 inch (~25 mm). The pre-determined fold line may be in the form of a seam (or seams) such as, for example, a stitched seam, an ultrasonic bond seam, adhesive bond seam, thermo-mechanical bond seam (e.g., a bar seal seam) or combinations thereof, that results from joining layers or plies together to form the barrier panel and the fold protection panel—or the seam(s) may result from joining pieces together if the barrier and fold protection panels are discrete pieces. Alternatively and/or additionally, the predetermined fold line may be identified by printing, or by an imprint such as a thermo-mechanical bond line (e.g., bar seal bond line) or pattern or other indicia, or identified by a crease or other suitable mark. The pre-determined fold line may be an intermittent line or indicia and it may be provided directly on the barrier panel or it may be provided on one or reinforcement elements if such are present.

As noted above, an important feature of the predetermined fold line 116 is that it helps delineate where the content to be wrapped and ultimately sterilized should be placed. That is, content to be wrapped and sterilized should be placed adjacent only one side of the predetermined fold line. As discussed subsequently, other features of the present invention signal to a user which side of the pre-determined fold line is the appropriate side to place content. Yet another feature of the predetermined fold line 116 is that it helps defines a boundary, reference line or limit for the user during the wrapping of content to be sterilized. That is, during wrapping of content to be sterilized, as part of the barrier panel is brought over the content to be sterilized, that part of the barrier panel should not be extended substantially across or beyond the predetermined fold line 116. In contrast to conventional sterilization wrap systems where the content is placed at the center of the sterilization barrier, the multi-panel sterilization assembly required placement at the pre-determined fold line near the boundary or edge of the barrier panel. This is initially counterintuitive for users and is quite different from conventional sterilization wrap systems.

While the barrier panel 102 of FIG. 6 is generally shown as having a square shape, the barrier panel 102 may be rectangular or may desirably have additional edges to define a non-square or non-rectangular shape. Portions of the edges may be arcuate or may otherwise be non-linear. Alternatively and/or additionally, the first edge 120 and the third edge 124 may converge or diverge so the edges are not parallel, thereby defining a barrier panel 102 having a trapezoidal shape. It is also contemplated that other combinations of opposite edges may converge or diverge.

Figure 7A:
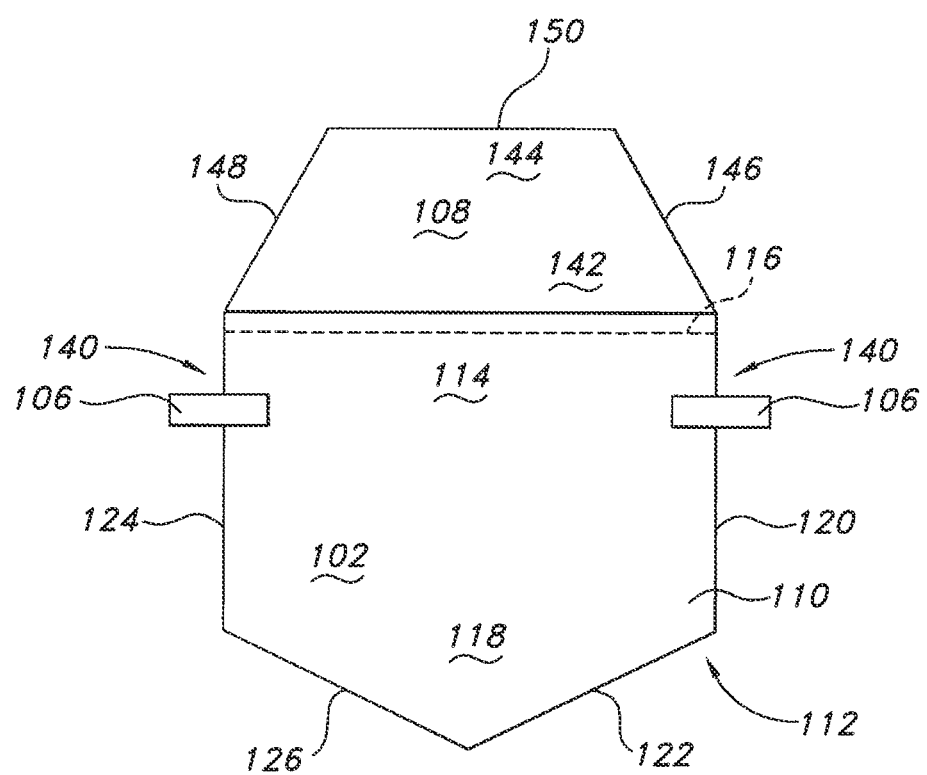
FIG. 7A is an illustration of an exemplary disposable flexible multi-panel sterilization assembly.

For example and referring to FIG. 7A, the barrier panel may have a fourth edge 126 to define a non-square or non-rectangular shape. In such an exemplary configuration, the two edges 122 and 126 are generally opposite the pre-determined fold line 116 such that the second edge 122 and the fourth edge 126 form an apex or vertex. Thus, the barrier panel 102 may have a first surface 110 and a second opposing surface 112; a first end 114 generally defining a pre-determined fold line 116; a second end 118 opposite the first end 114; a first edge 120 that is generally perpendicular to the pre-determined fold line 116; a second edge 122 that is generally opposite the pre-determined fold line 116; a third edge 124 that is generally perpendicular to the pre-determined fold line; and a fourth edge 126 located between the second edge 122 and the third edge 124.

Figure 8A:
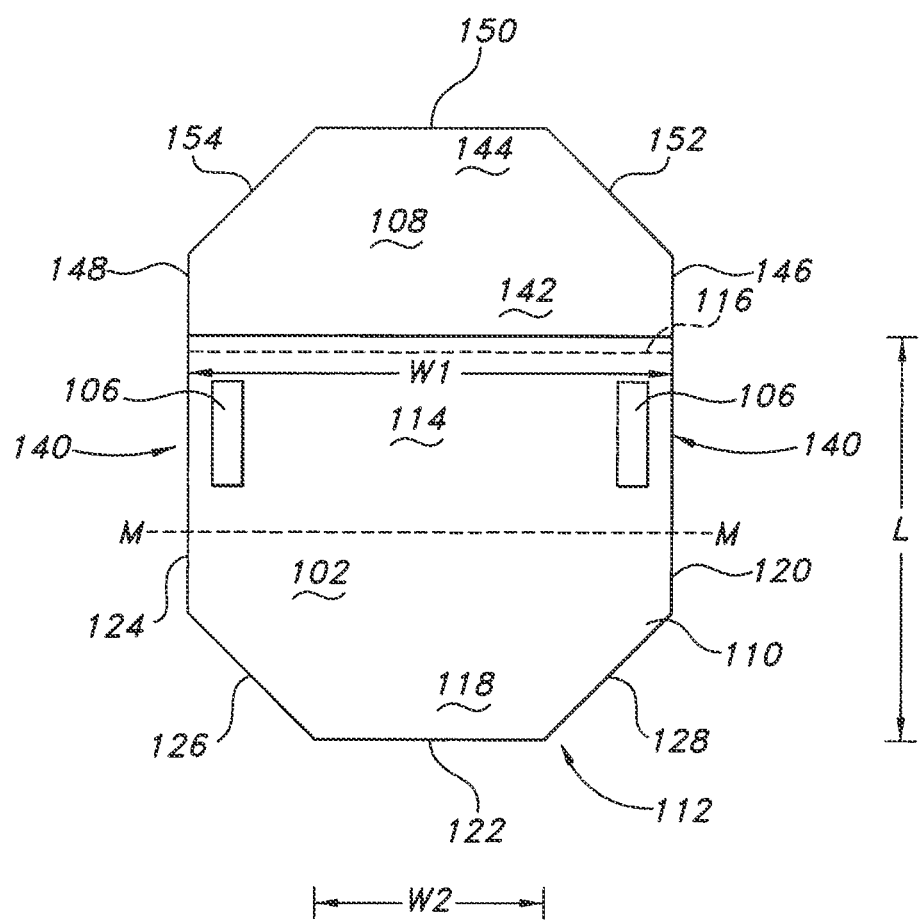
FIG. 8A is an illustration of an exemplary disposable flexible multi-panel sterilization assembly.
Figure 8B:
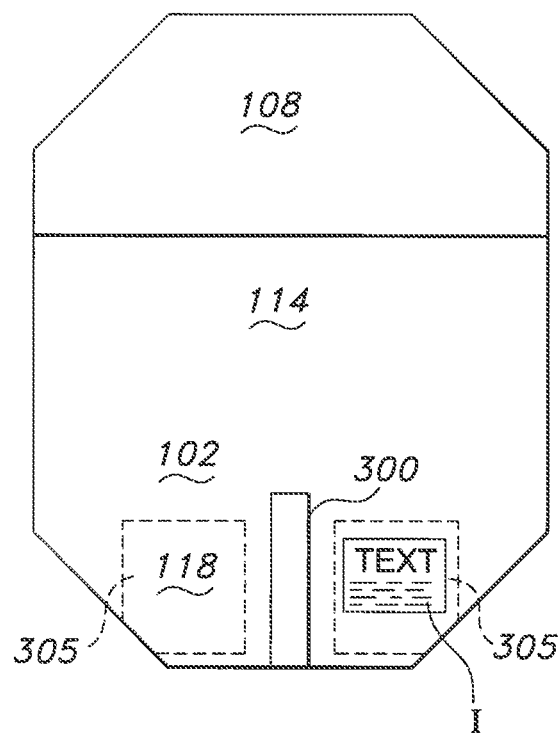
FIG. 8B is an illustration showing the opposite side of the exemplary disposable flexible multi-panel sterilization assembly of FIG. 8A.

Referring to FIGS. 8A and 8B, the barrier panel 102 may have a fourth edge 126 and a fifth edge 128 to define a non-square or non-rectangular shape such that, for example, the fourth edge 126 and a fifth edge 128 generally converge toward the second edge 226 such that the second end 118 of the barrier panel is narrower than the first end 114 of the barrier panel. Thus, the barrier panel 102 may have a first surface 110 and a second opposing surface 112; a first end 114 generally defining a pre-determined fold line 116; a second end 118 opposite the first end 114; a first edge 120 that is generally perpendicular to the pre-determined fold line; a second edge 122 that is generally parallel to the pre-determined fold line 116; a third edge 124 that is generally perpendicular to the pre-determined fold line 116; a fourth edge 126 located between the second edge 122 and the third edge 124; and, a fifth edge 128 located between the first edge 120 and the second edge 122. The barrier panel has a first width "W1" that is the distance from the first edge 120 to the third edge 124 in the first end 114 (e.g., preferably measured along the pre-determined fold line 116) and a second width "W2" that is the distance from the fourth edge 126 to the fifth edge 128 (e.g., preferably measured between the locations where the fourth edge 126 and the fifth edge 128 meet the second edge 122. The barrier panel also has a length "L" that is the distance from the first end 114 (from the pre-determined fold line 116) to the second end (e.g., at the second edge 122). The barrier panel also has a midpoint "M" along the length "L" and extending between the first edge 120 and the third edge 124 or, in some embodiments, the fourth edge 126 and the fifth edge 128 to generally delineate the barrier panel 102 into a content receiving region 130 extending from the pre-determined fold line 116 to the midpoint "M" and a content covering region 132 extending from the midpoint "M" to the second edge 122". Of course, it is contemplated that additional edges may be added or that edges may be curvilinear or may include curvilinear portions.

Referring again to FIG. 6, the barrier panel 102 may have a width "W" that is the distance from the first edge 120 to the third edge 124 and a length "L" that is the distance from the first end 114 to the second end 118. According to an aspect of the invention, the barrier panel has a midpoint "M" along the length "L" which spans or runs between the first edge 120 and the third edge 124 to generally delineate the barrier panel 102 into a content receiving region 130 extending from the pre-determined fold line 116 to the midpoint "M" and a content covering region 132 extending from the midpoint "M" to the second edge 124. Generally speaking the content receiving region is the portion of the barrier panel onto which a tray or other content to be sterilized is initially placed. Unlike conventional sterilization wrap in which a tray or content to be sterilized is placed in the central portion of the barrier material that forms the sterilization wrap, the content receiving region is between the first end and the midpoint of the barrier panel. This asymmetric placement on the barrier panel is not intuitive. The content covering region is the portion of the barrier panel that is folded over the content after the content has been placed on the content receiving region.

In an aspect of the invention, the barrier panel of the various illustrated configurations may have a width of from about 12 inches (~30 cm) to about 50 inches (~127 cm). Desirably, the barrier panel may have a width of from about 18 inches (~46 cm) to about 40 inches (~102 cm). Even more desirably, the barrier panel may have a width of from about 20 inches (~51 cm) to about 30 inches (~76 cm). The barrier panel may have a length of from about 7 inches (~18 cm) to about 50 inches (~127 cm). Desirably, the barrier panel may have a length of from about 15 inches (~39 cm) to about 40 inches (~102 cm). Even more desirably, the barrier panel may have a length of from about 25 inches (~64 cm) to about 30 inches (~76 cm).

According to an aspect of the invention, the surface area of the content receiving region 130 may be from about 25 percent to about 49 percent of the total surface area of the barrier panel 102. For example, the surface area of the content receiving region 130 may be from about 35 percent to about 45 percent of the total surface area of the barrier panel 102. This is important because the content covering portion of the barrier panel should be larger to provide additional surface area to properly cover the content.

The multi-panel sterilization assembly 100 includes a panel attachment means 106 located on the first surface 110 between the pre-determined fold line 116 and the midpoint "M" of the barrier panel. The panel attachment means 106 is desirably at or near the first edge 120 and/or or the third edge 124 of the barrier panel. Although the panel attachment means 106 is illustrated at or near both the first edge 120 and the third edge 124 of the barrier panel, the panel attachment means 106 may be at or near only one of these edges.

Figure 7B:
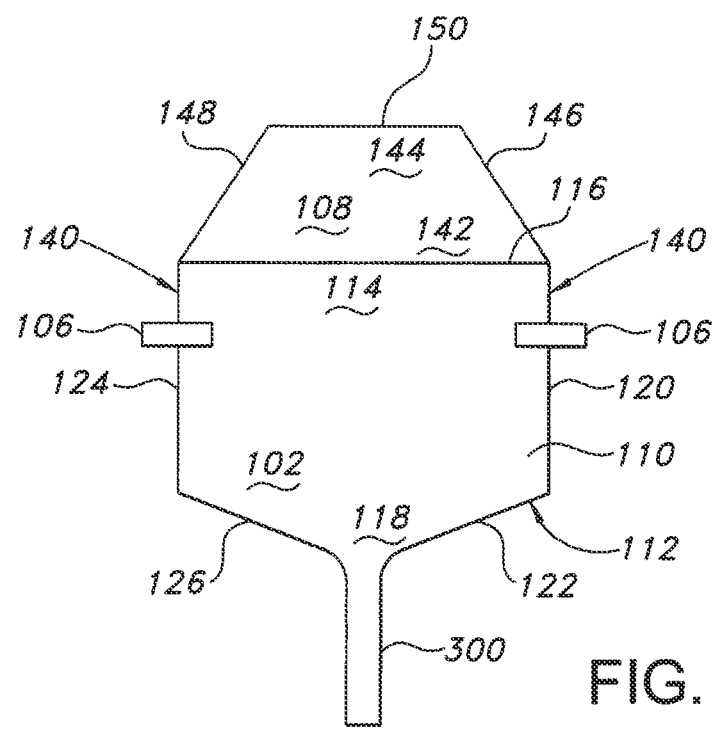
FIG. 7B is an illustration of an exemplary disposable flexible multi-panel sterilization assembly with an integral pull tab.
Figure 9A:
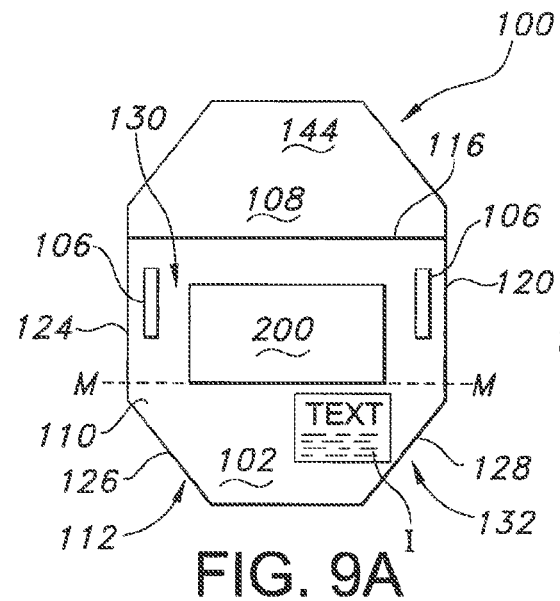
FIGS. 9A to 9E are illustrations of an exemplary sequence of folding an exemplary disposable flexible multi-panel sterilization assembly.

The panel attachment means 106 may be located at and extend from the first edge 120 and the third edge 124 of the barrier panel as generally illustrated in FIGS. 6 and 7A and 7B. Alternatively and/or additionally, the panel attachment means 106 may be located generally near the first edge and/or the third edge as illustrated in FIG. 8A and FIG. 9A. The panel attachment means may be one large element or a number of discrete elements. Exemplary panel attachment means include, but are not limited to, adhesive tape, double-sided adhesive tape, cleavable release tapes, layered release tapes, cohesive materials, hook and loop fastening systems, mechanical fastening systems including, but not limited to, snaps, clips, magnets, catches, slots and tabs, and combinations thereof. For example, the panel attachment means may be one or more lengths of adhesive tape having at least an end or portion that is stitched, ultrasonically bonded, thermomechanically bonded or adhered or adhesively bonded to the barrier panel. Desirably, the panel attachment means is a barrier panel attachment means that is located on the barrier panel and is used to join one or more edges of the barrier panel to itself. It has been found that barrier panel attachment means may be a double sided tape having the same or different levels of adhesive or tack strength of adhesive on each side. Alternatively and/or additionally, the panel attachment means may have a double sided tape structure in which the central layer sandwiched by the adhesive is a splittable or separable material such as a splittable paper, splittable laminate, splittable foam, cleavable paper, cleavable release structure, cleavable foam or other cleavable or separable laminate. Exemplary splittable or cleavable materials are disclosed at, for example, U.S. Pat. No. 5,702,555 issued to Caudal et al. on Dec. 30, 1997; U.S. Pat. No. 4,310,127 issued to Frye on Jan. 12, 1982; U.S. Pat. No. 3,675,844 issued to Sorrell on Jul. 11, 1972; and U.S. Pat. No. 2,205,956 issued to Humphner on Jun. 25, 1940; the contents of which are incorporated by reference.

According to an aspect of the invention, the panel attachment means 106 may be in the form of an adhesive fastening tab or tape closure system such as the various types frequently used on diapers, incontinent garments and similar products. An exemplary tape closure system may be found at, for example, U.S. Pat. No. 4,410,325 issued to Lare on Oct. 18, 1983; the contents of which are incorporated by reference. This system utilizes an adhesive fastening tab or tape closure system (referred to herein as a "tape") that is folded back on itself and which has a first end or portion that is attached to the article (e.g., one part of a garment). During use, the tape is unfolded to reveal an exposed adhesive surface at least at a second end or portion of the tape which is then adhered to a different part of the article (e.g., a second part of the garment) to secure the two parts of the garment in the desired configuration. Generally speaking, the first end of the tape panel attachment means 106 would be secured at or near the first edge 120 of the barrier panel and the second end of the tape panel attachment means 106 would be folded back onto the first end. An additional panel attachment means 106 may be secured at or near the third edge 124 of the barrier panel in a similar manner. During use, the tape panel attachment means 106 would be unfolded to reveal an exposed adhesive surface or surfaces at least at the second end of the panel attachment means 106. The exposed adhesive surface(s) of the panel attachment means at first edge 120 and/or third edge 124 of the barrier panel would be used to secure those portions of the barrier panel to each other and/or to other portions of the barrier panel after the barrier panel is folded about content to be sterilized. In such a configuration, an optional attachment zone 305 may be utilized. An exemplary optional attachment zone 305 is indicated by broken lines in FIG. 8B and in FIG. 9B. In embodiments that utilize adhesive or cohesive materials for the panel attachment means, the attachment zone 305 may be an applied film, a more securely bonded portion of a nonwoven fabric, a separate piece of a material, a coating or the like that provides a suitable surface for the adhesive to bond securely so folded barrier panel does not "pop" open or release when it should not do so. The attachment zone 305 may be configured to signal to a user the appropriate location or locations to secure the panel attachment means. In such configuration, the attachment zone 305 may be combined with or may incorporate indicia such as color, texture, alphanumeric characters or the like (illustrated in FIG. 8B as "T") to direct a user. More importantly, the attachment zone 305 can be configured to provide a suitable surface such that the fTorce required to release the panel attachment means 106 is carefully controlled to preserve aseptic opening, avoid tearing or shredding of the barrier fabric, provide a satisfactory level of resistance to sheer forces, and/or provide a satisfactory or controlled level of resistance to peel forces.

Another exemplary tape closure system may be found at, for example, U.S. Pat. No. 4,585,450 issued to Rosch et al. on Apr. 29, 1986; the contents of which are incorporated by reference. This system utilizes an adhesive fastening tab or tape closure system (referred to herein as a "tape") that includes a secondary tape element and a primary tape element. The tape has a first end or portion that is attached to the article (e.g., one portion of a garment). The second end or portion contains the secondary tape element and primary tape element. During use, an adhesive surface of the primary tape element is exposed. The adhesive surface of the primary tape element is then adhered to a different part of the article (e.g., a second part of the garment) to secure the two parts of the garment in the desired configuration. An adhesive bond between the primary tape element and the secondary tape element has less strength than the adhesive bond between the primary tape element and the second part of the garment or article such that the bond between the primary tape element and secondary tape element may be reliably separated, repeatedly if necessary.

Generally speaking, the first end or a first side of a panel attachment means 106 would be secured at or near the first edge 120 of the barrier panel and the second end or the second side of the tape panel attachment means 106 would be folded back onto the first end or otherwise covered by a release element. An additional panel attachment means 106 may be secured at or near the third edge 124 of the barrier panel in a similar manner. During use, the primary tape element of the panel attachment means 106 would be unfolded or uncovered to reveal an exposed adhesive surface(s) at least at the second end or second side of the panel attachment means 106. The exposed adhesive surface(s) of the primary tape element of would be used to join the first edge 120 and/or third edge 124 of the barrier panel to each other or to other portions of the barrier panel after the barrier panel is folded about content to be sterilized. In such a configuration, the adhesive bond between the primary tape element and the secondary tape element has less strength than the adhesive bond between the primary tape element and the portion of the barrier panel to which it is adhered such that the bond between the primary tape element and secondary tape element may be reliably separated, repeatedly if necessary. In some respects, the primary tape element may function as an attachment zone. That is, after the primary tape element is adhered to the barrier panel to secure the barrier panel in a folded configuration, the primary tape element may provide a suitable surface such that the force required to overcome the adhesive bond between the primary tape element and the secondary tape element is carefully controlled to preserve aseptic opening, avoid tearing or shredding of the barrier fabric, provide a satisfactory level of resistance to sheer forces, and/or provide a satisfactory or controlled level of resistance to peel forces. In another aspect, the attachment zone 305 as describe previously or in the form of the primary tape element may be used to allow a worker to re-open the wrapped barrier panel prior to inspect contents prior to sterilization and then re-attach the panel attachment means without having to destroy the multi-panel sterilization assembly.

As another example, the panel attachment means may be a length of fabric such as nonwoven fabric having an end or portion that is stitched, ultrasonically bonded, thermo-mechanically bonded or adhered or adhesively bonded to the barrier panel and having a hook fastener from a hook and loop fastening system joined to the other end. It is contemplated that the barrier fabric itself may function as the loop component of a hook and loop fastening system such as hook and loop fastenings systems available as VELCRO® brand fastener products from Velcro Industries B.V. Other exemplary hook systems may be used such as the hook system described in U.S. Pat. No. 5,315,740 issued to Nestegard which relates to hooks having small dimensions so they engage low cost loop materials such as nonwoven webs.

It is contemplated that various elements or components of the panel attachment means, may be integrally formed, such as by molding, co-extrusion or the like, along with any associated substrate layer. For example, the individual hook elements may be integrally formed simultaneously with a hook base-layer by coextruding the base layer and hook elements from substantially the same polymer material.

According to an aspect of the invention, the panel attachment means 106 is joined to the first surface 110 of the barrier panel 102 at a pre-determined position 140 to identify or distinguish the content receiving region 130 of the barrier panel 102 from the content covering region 132 as generally illustrated in FIGS. 6 and 9A. The location of the panel attachment means 106 at the pre-determined position 140 also signals to a user an optimum zone or region within the content receiving region 130 to place content. This may be highlighted by indicia on the assembly and/or instructions (illustrated in FIGS. 6, 8B, 9A and 9B as "I") on the assembly or which accompany the assembly and which may be posted in the workplace or displayed at a wrapping station.

Referring to FIGS. 8A and 9A, the panel attachment means 106 is desirably a double sided tape having a length that is greater than its width. For example, the panel attachment means may be a double sided tape having a length that more than two times great than its width. As another example, the panel attachment means may be a double sided tape having a length that is four times great than its width to eight times greater than its width. Alternatively and/or additionally, the configuration of the panel attachment means may be a series of tape squares arranged along or near the first edge 120 and the third edge 124. The portion of the panel attachment means 106 closest to the pre-determined fold line 116 is desirably less than about 3 inches from the pre-determined fold line 116. More desirably, the portion of the panel attachment means 106 closest to the pre-determined fold line 116 is desirably less than about 2 inches from the pre-determined fold line 116. For example, the portion of the panel attachment means 106 closest to the pre-determined fold line 116 may be about 1 inch to about ½ inch from the pre-determined fold line 116.

Referring again to FIG. 6, the fold protection panel 108 of the multi-panel sterilization assembly 100 is in juxtaposed communication with the barrier panel 102. That is, the fold protection panel 108 is in side-by-side relationship with or adjoins the barrier panel 102. Generally speaking, the fold protection panel 108 may be any suitable material but desirably is formed of a permeable sheet material. According to the invention, the fold protection panel includes a proximal end 142 generally adjacent the pre-determined fold line 116; a distal end 144 generally opposite the proximal end 142; and at least a first edge 146 and a second edge 148 extending from the proximal end 142 to the distal end 144. According to the present invention, the fold protection panel may have additional edges. For example and with reference to FIG. 7A, the fold protection panel may include at least a third edge 150 located at or along its distal end 144. As yet another example and referring now to FIG. 8A, the fold protection panel may include at least a third edge 150 located at or along its distal end 144 and a fourth edge 152 and a fifth edge 154.

Generally speaking, the fold protection panel may be a lightweight material such as a lightweight laminate of spunbond nonwoven material or a lightweight laminate of spunbond nonwoven material and meltblown nonwoven material. As such, the fold protection panel does not need to provide a higher level of barrier properties like the material that forms the barrier panel. The fold protection panel may be configured so it has barrier properties. For example, the fold protection panel may be formed of the same material as the barrier panel. It is contemplated that the fold protection panel may be a single layer of spunbond nonwoven material.

In an aspect of the invention, the fold protection panel desirably has a width that is the distance from the first edge to the second edge and a length that is the distance from the proximal end to the distal end. The fold protection panel may have a width of from about 12 inches (~30 cm) to about 50 inches (~127 cm). Desirably, the fold protection panel may have a width of from about 18 inches (~46 cm) to about 40 inches (~102 cm). Even more desirably, the fold protection panel may have a width of from about 20 inches (~51 cm) to about 30 inches (~76 cm). The fold protection panel may have a length of from about 6 inches (~15 cm) to about 30 inches (~76 cm). Desirably, the fold protection panel may have a length of from about 8 inches (~20 cm) to about 20 inches (~51 cm). Even more desirably, the fold protection panel may have a length of from about 12 inches (~30 cm) to about 15 inches (~38 cm).

During use, panel attachment means 106 are used to join the barrier panel's first edge 120 and third edge 124 to a portion of the content covering region 132 after the barrier panel 102 has been folded at or near its midpoint "M" such that its second end 118 is brought near its first end 114. It is contemplated that in some embodiments, the panel attachment means 106 may be used to join the barrier panel's first edge 120 and third edge 124 to each other.

According to an aspect of the invention, it is important that the adhesive force or the engagement force at which the panel attachment means join the respective edges of the barrier panel to the content covering region of the barrier panel or to the edges themselves should be sufficient to secure the barrier panel around the content thereby forming a package that is robust and able to withstand normal handling before as well as after sterilization.

In exemplary arrangements, especially where there are sufficiently high levels of engagement shear force provided by the panel attachment means, the fastening engagement may provide a peel force value of not less than a minimum of about 5 grams-force (gmf) (about 0.012 lbs-force) between the panel attachment means and the other portion of the barrier panel that it secures together. In further arrangements, the fastening engagement may provide a peel force value of between about 6 gmf and about 50 gmf to provide improved advantages. In desired configurations, the fastening engagement may provide a peel force value about between about 10 gmf and about 30 gmf between the panel attachment means and the other portion of the barrier panel that it secures together. More desirably, the peel force value may be between about 15 gmf and about 20 gmf. Generally speaking, the peel force should not be more than about 100 gmf, and desirably is not more than about 75 gmf to further provide improved benefits. When the peel force is greater than these values, there is difficulty opening/unwrapping the package containing sterilized contents in an aseptic manner.

The engagement force between the panel attachment means and the other portion of the barrier panel that it secures together may additionally provide a shear force value that is desirably greater than about 5,000 gmf for a panel attachment means having dimensions of about 4 by 1 inches (~102 by ~25 mm). Generally speaking, the resistance to shear force should not be less than about 750 gmf per square inch of the area of engagement between the panel attachment means and the other portion of the barrier panel that it secures together. Desirably, the shear force is not less than about 1,000 gmf/square inch, and more desirably, is not less than about 2,000 gmf/square inch. Even more desirably, the shear force is not less than about 2,500 gmf/square inch. In further aspects, the shear force can be up to about 4,400 gmf/square inch, or more. Alternatively, the shear force is not more than about 3,900 gmf/square inch, and optionally is not more than about 3,500 gmf/square inch to provide improved performance.

The peel force value can be determined utilizing the procedure set forth below in the Examples section. Alternatively, the peel force value can be determined in accordance with standard procedure ASTM D-5170, approved Sep. 15, 1991 and published November 1991.

The shear force value can be determined utilizing the procedure set forth below in the Examples section. Alternatively, the shear force value can be determined in accordance with standard procedure ASTM D-5170, approved Sep. 15, 1991 and published November 1991. The test specimen is composed of the panel attachment means and the portion of the barrier panel to which it secures. The test specimen length and width typically correspond to the length and width employed to conduct the subsequently described testing for peel force value. During testing, the test specimen length is aligned perpendicular to the direction in which a shear force is typically applied to the panel attachment means (e.g., double sided tape fastener) during the ordinary use of the article with which the fastener is employed. The specimen "width" is perpendicular to the specimen length. That is, shear force is typically applied across the width of the specimen (i.e., perpendicular to the length) for a specimen having a length that is greater than its width—which is the configuration illustrated in FIGS. 8A and 9A.

It should be readily appreciated that the adhesive force or the engagement force at which the panel attachment means join the respective edges of the barrier panel to the content covering region of the barrier panel or to the edges themselves should be less than the peel strength of the bond that is used to join the panel attachment means to the underlying barrier panel during construction of the assembly. For example, the peel strength of the bond (e.g., adhesive, mechanical, thermo-mechanical, ultrasonic, etc.) that is used to join the panel attachment means to the underlying barrier panel during construction should be much greater than about 400 gmf for a panel attachment means having a dimension of about 4 inches by 1 inch (about 10 cm by 2.5 cm). Desirably, the peel strength of the bond that is used to join the panel attachment means to the underlying barrier panel during construction should be greater than about 400 gmf per square inch of the area of engagement between the panel attachment means and the barrier. For example, the bond strength may be more than 1000 gmf/square inch, and may be more than 4,000 gmf/square inch.

Referring now to FIGS. 9A through 9E (and with additional reference to FIG. 8A), there is illustrated an example of a multi-panel sterilization assembly in an exemplary sequence of folding. FIG. 9A illustrates a multi-panel sterilization assembly 100 composed of barrier panel 102 which cooperates with the fold protection panel 108 and the panel attachment means 106 on the first surface 110 so the barrier panel 102 can be folded around the content 200 to form a package (such as the package 202 generally illustrated in FIG. 9E). The barrier panel 102 is the portion of the flexible multi-panel sterilization assembly 100 that contacts and covers the content 202. The content 200 is placed in the content receiving 130 which is generally defined by the panel attachment means 106 on the first surface 110 of the barrier panel 102.

Figure 9B:
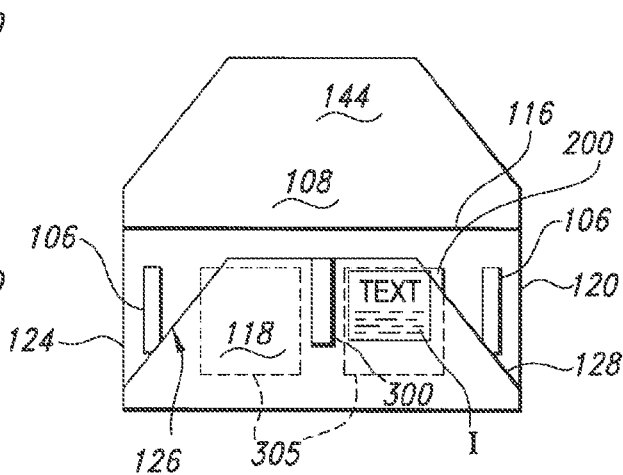

As generally illustrated in FIG. 9B, the second end 118 of the barrier panel 102 is folded up at the midpoint "M" and brought to the first end 114 so the content covering region 132 of the barrier panel 102 extends over the content 200. As shown in FIG. 9B, the width of the barrier panel at the second end 118 is less than the width of the barrier panel at the first end 114. This is important when the panel attachment means 106 are located directly on the barrier panel as shown in FIGS. 8A and 9A (rather than extending outward from the edges as illustrated in FIGS. 7A and 7B) because it provides a configuration of the fourth edge 126 and the fifth edge 128 that allows access to the panel attachment means 106 after the second end 118 is brought up to the first end 114.

Figure 7C:
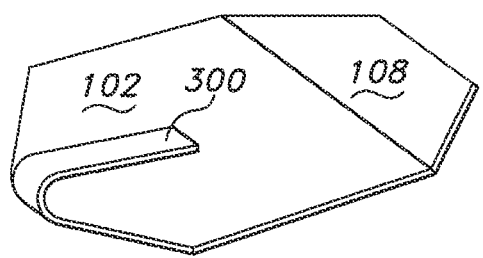
FIG. 7C is an illustration highlighting a detail of the exemplary disposable flexible multi-panel sterilization assembly of FIG. 7B.

In some embodiments of the present invention, a pull tab or tail 300 is extends from the second end 118 so that the pull tab or tail 300 is positioned to be accessible during the initial steps of unfolding or unwrapping a wrapped package. The pull tab or tail 300 desirably extends from or is joined to the second end 118 of the barrier panel on the second opposing surface 112 of the barrier panel 102. Referring briefly to FIG. 7B, there is shown a configuration in which the pull tab or tail 300 is unitary or integral with the barrier panel. FIG. 7C illustrates that pull tab or tail 300 on the second opposing surface 112 of the barrier panel 102. The distal end (i.e., the loose end) of the pull tab or tail 300 is desirably secured to the barrier panel with a light adhesive or an adhesive tab or sticker such that the pull tab or tail 300 does not flop around during wrapping and is in an appropriate position during unwrapping.

Figure 9C:
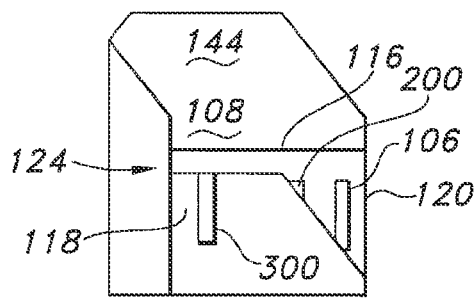

Referring now to FIG. 9C, that illustration shows that the third edge 124 of the barrier panel 102 is folded over the second end 118 (after the second end 118 is brought up to the first end 114). While not necessarily shown to scale, the third edge 124 of the barrier panel 102 after folding does not extend very far toward the middle of the assembly.

Figure 9D:
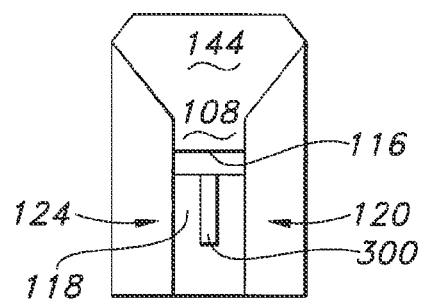

FIG. 9D illustrates that the first edge 120 of the barrier panel 102 is folded over the second end 118. While not necessarily shown to scale, the first edge 120 of the barrier panel 102 upon folding does not extend very far toward the middle of the assembly. Accordingly, it is evident that the third edge 124 and the first edge 120 generally do not overlap.

Unlike conventional sterilization wrap in which the edges are intentionally overlapped as generally illustrated in FIGS. 4 and 5, the edges 120 and 124 of the barrier panel are separated by a distance. This difference highlights the importance of the panel attachment means 106 to hold the folded edges 120 and 124 of the barrier panel 102 in place about the content. Moreover, having these edges generally exposed highlights the importance of the fold protection panel 108.

Figure 9E:
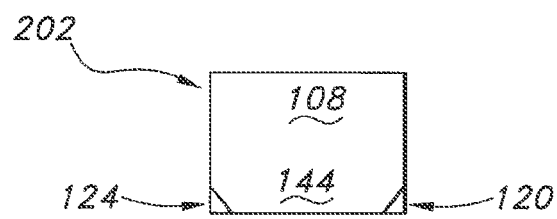

Referring now to FIG. 9E, the fold protection panel 108 is folded at the pre-determined fold line 116 bringing its distal end 144 over the second end 118 of the barrier panel. In some embodiments, a portion of the material adjacent the first edge 120 and the third edge 124 may be visible. With this configuration, the actual edges 120 and 124 of the barrier panel 102 are fully covered so the edges themselves are less susceptible to being accidently pulled open or breached during normal handling of the package. The fold protection panel is typically secured utilizing conventional tape that is used with sterilization wrap. Desirably, the fold protection panel covers the edges of the barrier protection panel after it is folded around the content to be sterilized to form a package. The fold protection panel covers these edges to prevent a worker inadvertently opening the folded barrier protection panel. In addition, the fold protection panel shields the edges from snags, pulls or other phenomenon that could impart a peel force to these edges that would cause the panel attachment means to detach. That is, the configuration of the multi-panel sterilization assembly utilizes the fold protection panel to protect exposed edges of the barrier panel after the barrier panel has been folded around content to be sterilized to form a package.

According to the present invention, the barrier panel may be composed of at least one layer of a breathable nonwoven material. Desirably, the breathable nonwoven material is a laminate composed of a layer of spunbonded filaments, a layer of meltblown fibers, and a layer of spunbonded filaments—also called spunbonded-meltblown-spunbonded material. The method of making these layers is known and described in commonly assigned U.S. Pat. No. 4,041,203 to Brock et al which is incorporated herein in its entirety by reference. The material of Brock et al is a three layer laminate of spunbonded-meltblown-spunbonded layers which is also commonly referred to by the acronym "SMS". The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to it fine fiber structure which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5-50% of the surface area of the laminate. Desirably, the bonds may occupy about 10-30% of the surface area of the laminate. Other combinations and variations of these materials are contemplated. As a non-limiting example, the inner layer may contain two meltblown layers such that the material may be called "SMMS".

When the barrier panel is composed of or incorporates SMS material(s), the basis weight of the SMS material(s) may be from 1 ounce per square yard or "osy" which is approximately (33 grams per square meter or "gsm") to about 3 osy (100 gsm). For example, the basis weight of the SMS material(s) may be from 1.2 osy (40 gsm) to about 2 osy (67 gsm). As another example, the basis weight of the SMS material(s) may be from 1.4 osy (47 gsm) to about 1.8 osy (60 gsm). The basis weight may be determined in accordance with ASTM D3776-07. Multiple plies or layers of SMS material may be used to provide basis weights ranging from about 2 osy (67 gsm) to about 5 osy (167 gsm).

The permeability of the barrier panel may range from 25 to about 500 cubic feet per minute (CFM) as characterized in terms of Frazier permeability. For example, the permeability of the barrier panel may range from 50 to about 400 cubic feet per minute. As yet another example, the permeability of the barrier panel may range from 100 to about 300 cubic feet per minute. The Frazier permeability, which expresses the permeability of a material in terms of cubic feet per minute of air through a square foot of area of a surface of the material at a pressure drop of 0.5 inch of water (or 125 Pa), was determined utilizing a Frazier Air Permeability Tester available from the Frazier Precision Instrument Company and measured in accordance with Federal Test Method 5450, Standard No. 191A. When the barrier panel is composed of or incorporates SMS material(s) have basis weights ranging from about 1 osy (33 gsm) to about 2.6 osy (87 gsm), the permeability of the barrier panel may range from about 20 cubic feet per minute to about 75 cubic feet per minute when determined generally in accordance with ISO 9237:1995 (measured with an automated air permeability machine using a 38 $cm^2$ head at a test pressure of 125 Pa,—exemplary air permeability machine is TEXTEST FX 3300 available from TEXTEST AG, Switzerland). If multiple plies or layers of SMS material are used to provide basis weights ranging from about 2 osy (67 gsm) to about 5 osy (167 gsm), the permeability of the barrier panel may range from about 10 cubic feet per minute to about 30 cubic feet per minute when determined generally in accordance with ISO 9237:1995.

As noted above, the flexible multi-panel sterilization assembly 100 may include at least one pull tab 300 extending from the second end 118 of the barrier panel 102. The pull tab 300 may be formed of the same material as the barrier panel or may be formed of one or more different materials. The pull tab is a feature that can be grasped by a person unfolding a sterilized package formed of a folded flexible multi-panel sterilization assembly containing sterilized content without compromising the sterile field formed by the unfolded content-contacting portions of the barrier panel. The pull tab 300 may be attached to the barrier panel or it may be integral or unitary with the barrier panel. In an aspect of the invention, the barrier panel at or adjacent the edges near the pull tab 300 may be bonded together utilizing a seam such as, for example, a stitched seam, an ultrasonic bond seam, adhesive bond seam, thermo-mechanical bond seam (e.g., a bar seal seam) or combinations thereof to provide sufficient stiffness, rigidity or support to that portion of the barrier panel so that folding or creasing of the barrier panel is reduced or eliminated when force is applied to the pull tab 300 during unwrapping. This is important to preserve the sterility of the contents during unwrapping. For example, the second edge 122 and the fourth edge 126 illustrated in FIG. 7B may be partially or substantially bonded to provide such a configuration. As another example, the second edge 122 illustrated in FIG. 8A may be partially or substantially bonded to provide the desired configuration. As yet another example, the second edge 122 and/or the fourth edge 126 and fifth edge 128 illustrated in FIG. 8A may be partially or substantially bonded to provide the desired configuration.

In an embodiment of the invention, the sterilization assembly may further include one or more discrete reinforcement elements in the content receiving region. In addition to reinforcing the barrier panel, the reinforcement element may define an area for receiving content to be sterilized. The reinforcement elements may include one or more layers of materials selected from fibrous webs, impermeable films, permeable or porous films, apertured films, foams and combinations thereof. For example, fibrous webs may include those that are woven and nonwoven. Woven webs may include natural or synthetic materials or blends of the same. As examples, natural materials could be weaves of cotton yarn, and synthetic materials could be weaves of polypropylene, polyester, or nylon yarn and the like. Nonwoven webs may include, for example, spunbond, meltblown, carded webs, wet formed or airlaid webs, or laminates of the same (e.g., spunbond/meltblown/spunbond). Such nonwoven webs may also include natural or synthetic materials or blends of the same. The reinforcement elements include one or more layers of material selected from permeable or impermeable films or laminates of the same. Permeable films may be apertured or be microporous. Apertured films may be obtained through mechanical aperturing, vacuum aperturing, or other commercially available techniques. Microporous films and other similar films may be produced as generally described at, for example, U.S. Pat. No. 5,695,868; U.S. Pat. No. 5,698,481; U.S. Pat. No. 5,855,999; and U.S. Pat. No. 6,277,479; the contents of which are incorporated herein by reference. Impermeable films can be monolayer or coextruded and can be comprised of film materials including, for example, polyethylenes, polypropylenes, copolymers thereof, vinyls, metal foils, and the like. It should also be noted said films may also be laminated with fibrous webs, described above.

Reinforcement elements are discrete zones of the barrier panel of containing additional material or treatments to reduce the likelihood that the barrier panel will be compromised by pressure cuts, pressure holes, tears or the like in the locations where the content is likely to concentrate forces against the material(s) of the barrier panel. It is envisioned that relative to the material(s) of the barrier panel, the reinforcement elements can be less permeable or even impermeable to hot air, steam, or other sterilization gas, while still allowing for proper sterilization and removal of sterilant gas. It has been found that acceptable sterilization and removal of sterilant gas will take place if the permeability of the sterilization package web is greater than about 25 cubic feet per minute (cfm) as characterized in terms of Frazier permeability. As such, a reinforcement element material that is impermeable or less permeable than the sterilization package material is acceptable, as long as the overall sterilization package is adequately permeable (i.e., greater than about 25 cfm). If an impermeable or less permeable reinforcement element material is desirable, the permeability of the overall sterilization package can be varied by changing the area covered by the reinforcement element. It is desirable that the sterilization package web maintain an overall permeability of at least about 25 cfm.

The reinforcement elements may also be configured to identify the content receiving region 130 of the barrier panel 102. Alternatively and/or additionally the reinforcement elements may be configured to cooperate with the panel attachment means to identify the content receiving region 130 of the barrier panel 102. For example, the reinforcement elements may be in the form of discrete shapes placed within the content receiving region. FIGS. 10A through 10D are illustrations of exemplary flexible multi-panel sterilization assemblies 100 composed of a barrier panel 102, panel attachment means 106 and a fold protection panel 108 and which further include reinforcement elements 302.

FIG. 10A illustrates a flexible multi-panel sterilization assembly 100 in which four reinforcement elements 302 are positioned at spaced apart locations in the content receiving region 130 of the barrier panel 102 generally at the locations that correspond to the corners of a sterilization tray or similar content. FIG. 10B illustrates a flexible multi-panel sterilization assembly 100 in which two reinforcement elements 302 are positioned at spaced apart locations on the barrier panel 102 extending from the pre-determined fold line 116 to a fourth edge 126 and a fifth edge 128 of the barrier panel 102 generally opposite the pre-determined fold line 116. The two reinforcement elements 302 are positioned in the content receiving region 130 generally at the locations that correspond to the corners of a sterilization tray or similar content. FIG. 10C illustrates a flexible multi-panel sterilization assembly 100 in which two reinforcement elements 302 are positioned at spaced apart locations on the barrier panel 102 generally parallel to the pre-determined fold line 116 between the two panel attachment means 106 at or adjacent a first edge 120 and a third edge 124. The two reinforcement elements 302 are positioned in the content receiving region 130 generally at the locations that correspond to the corners of a sterilization tray or similar content. FIG. 10D illustrates a flexible multi-panel sterilization assembly 100 in which two reinforcement elements 302 are positioned at spaced apart locations on the barrier panel 102 and the fold protection panel 108. The two reinforcement elements 302 extend in generally parallel configuration from a distal end 144 of the fold protection panel 108 to a fourth edge 126 and a fifth edge 128 of the barrier panel 102. The two reinforcement elements 302 are positioned in the content receiving region 130 generally at the locations that correspond to the corners of a sterilization tray or similar content. It should be noted that a pull tab or tail 300 is illustrated in FIGS. 10A to 10D as extending out from underneath the barrier panel. This representation is merely intended to illustrate that a pull tab or tail 300 may be included and not particularly how it is preferably configured.

Of course, the reinforcement elements may have a wide variety of shapes, sizes and other configurations. FIGS. 11A and 11B are illustrations of exemplary reinforcement elements 302. FIG. 11A illustrates reinforcement elements 302 having generally triangular configurations. FIG. 11B illustrates an exemplary reinforcement element 302 composed of several overlapping triangular elements. Alternatively and/or additionally, the reinforcement element 302 illustrated in FIG. 11B may be formed by a single piece of material. Other shapes and configurations are contemplated such, for example, "H" patterns, "X" patterns, or the like.

Figure 12:
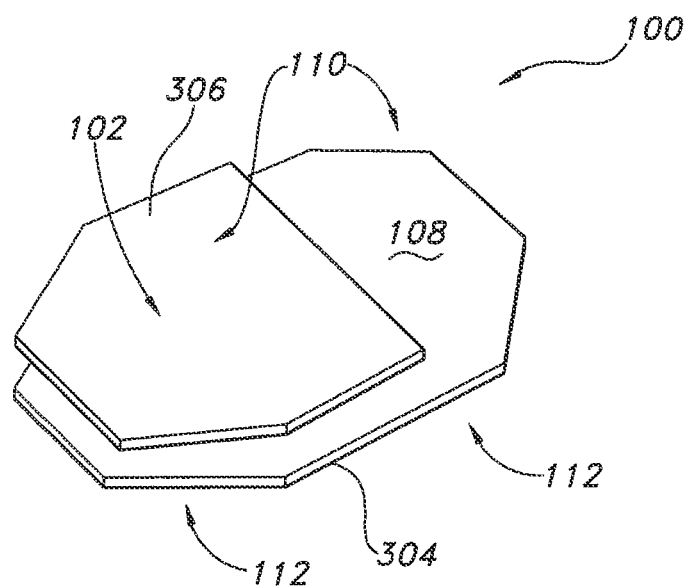
FIG. 12 is an illustration of an exploded or broken apart perspective view of exemplary features of an exemplary disposable flexible multi-panel sterilization assembly.

In an aspect of the invention, the construction of the disposable flexible multi-panel sterilization assembly may be based on a two primary pieces of material. Referring now to FIG. 12, there is shown an illustration of an exemplary disposable flexible multi-panel sterilization assembly 100 in exploded or broken apart view revealing a first layer 304 of a material and a second layer 306 of material. In this configuration, the first layer 304 of material and the second layer 306 of material overlap to define the barrier panel 102. Generally speaking, these layers may be joined by adhesives, ultrasonic bonding, thermo-mechanical bonding or the like. The layers are desirably joined at or adjacent at least two of the edges and along the pre-determined fold line. For example, the layers may be joined along the first edge 120 and the third edge 124. The bonding may be a complete seam or the edge may be partially bonded along only one or a few portions of the edge. Alternatively and/or additionally, the bonding may be intermittent or discontinuous along all or a portion of the respective edge. Of course, other edges may also be bonded or the layers may be bonded together across all or portions of their entire surface area. The region where there is no overlap of the first layer 304 of material and second layer 306 of material forms the fold protection panel 108. Generally speaking, the first layer 304 of material and the second layer 306 of material may be the same material or they may be different materials. For example, the first layer 304 of material may be single layer or multiple layers of spunbond nonwoven material, a lightweight nonwoven laminate material, or a material that lacks the level of barrier properties (or other characteristics) that may be desired for the barrier panel. The second layer 306 of material desirably has a higher level of barrier properties than the first layer 304 of material. For example, the second layer 306 of material may be a laminate of nonwoven fabrics such as "SMS" material. The second layer 306 of material may have a different color and/or pattern than the first layer 304 of material. For example, the first layer 304 of material may have a first color (e.g., a blue color), a dark color, or a specific color on a color scale and the second layer 306 of material may have no color (e.g., white), a second color (e.g., a light color), or a specific color on a color scale that contrasts with the first color.

As generally shown in FIG. 12, the first surface 110 of the disposable flexible multi-panel sterilization assembly 100 may be formed of the second layer 306 of material and the first layer 304 of material and the second opposing surface 112 may be formed of the first layer 304 of material. It is contemplated that the first surface 110 of the disposable flexible multi-panel sterilization assembly 100 may be formed of the first layer 304 of material and the second opposing surface 112 may be formed of the first layer 304 of material and the second layer 306 of material. It is also contemplated that other combinations of layers may be used such that two layers of material generally corresponding in size to the first layer of material 304 may sandwich or enclose an intermediate layer of material corresponding in size to the second layer of material 306 such that the first surface 110 and the second opposing surface 112 are generally the same such that one surface does not reveal two discrete layers of material (i.e., does not show both the first layer 304 of material and the second layer 306 of material).

It is contemplated that the color differentiation or contrast between the first layer 304 of material and the second layer 306 of material may be useful to function as an indicator that barrier properties of the barrier panel may be compromised.

Figure 13:
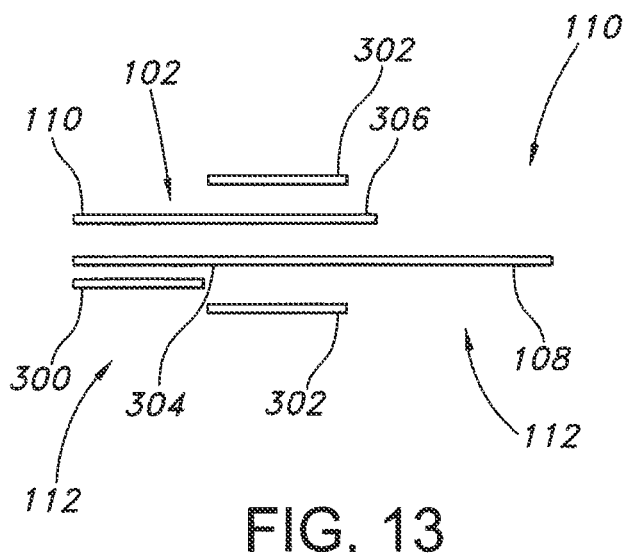
FIG. 13 is an illustration of an exploded or broken apart cross-section view of exemplary features of an exemplary disposable flexible multi-panel sterilization assembly.

Referring now to FIG. 13, there is shown an illustration of an exemplary disposable flexible multi-panel sterilization assembly 100 in exploded or broken apart cross-sectional view revealing a first layer 304 of a material and a second layer 306 of material. In this configuration, the first layer 304 of material and the second layer 306 of material overlap to define the barrier panel 102. The region where there is no overlap of the first layer 304 of material and second layer 306 of material forms the fold protection panel 108. The cross-sectional view illustrates reinforcement elements 302. The reinforcement elements 302 may be present on the first surface 110 to desirably identify the content receiving region 130 of the barrier panel 102 between the panel attachment means 106. Alternatively and/or additionally, the reinforcement elements 302 may be located on the second opposing surface 112 of the barrier panel.

Sterilization wrap has many modes of failure involving tears, cuts, punctures, holes or other breaches. Any failures may have serious consequences. The more common modes of failure are conventionally believed to involve tears, holes or cuts initiating from the sterilization tray or other content that is wrapped by or otherwise enclosed by conventional sterilization wrap fabric. In other words, tears, cuts or holds were believed to begin at the interface between the sterilization tray or other content and the sterilization wrap fabric itself and propagate from the inside of the sterilization wrap fabric penetrating outwardly through the material ultimately creating a breach. Accordingly, much effort has been expended to develop corner guards and other types of protection that is placed between the sterilization tray or other content and the sterilization wrap.

In an aspect of the present invention, it has been discovered that pressure holes and pressure cuts of the type in which the fibers adjacent the hole or cut appear to have been fused or "welded" together most commonly propagate from the outside of a package (i.e., content enclosed by sterilization wrap fabric) rather than propagating the sterilization tray or other content that is wrapped by or otherwise enclosed by conventional sterilization wrap fabric. Accordingly, the applicants have discovered that locating the reinforcement elements 302 on the second opposing surface 112 of the barrier panel provides an unexpected advantage because the second opposing surface 112 of the barrier panel 102 is the portion of the disposable flexible multi-panel sterilization assembly 100 that does not contact the content (e.g., sterilization tray) and which typically forms the outside of a wrapped package. Reinforcement elements 302 located on the second opposing surface 112 provide more efficient protection against pressure holes and pressure cuts because the inventors have discovered that pressure holds and pressure cuts tend to propagate from the outside of a wrapped package. While the inventors should not be held to any particular theory of operation, it has been discovered that pressure cuts and pressure holes are more frequently caused when content enclosed by sterilization wrap contacts an irregular surface with sufficient force during a single contact event or during multiple contact events such that the irregular surface concentrates the force to generate energy that causes failure.

Such contact events are frequently encountered when an individual wrapped sterilization tray or stacks of wrapped sterilization trays (particularly at overloaded weights) are transported by cart or other similar device and the cart or similar device stops abruptly (e.g., due to impact), encounters bumps or abrupt shocks. Other sources of contact events occur when wrapped trays are dropped (especially on the edge of a cart); when wrapped trays are dragged or pushed across a smooth surface; when a wrapped tray contacts a hard surfaces; and/or when excessive pressure is applied to a wrapped tray. For example, lifting the front end of a 20 pound tray so that all the weight of the tray is resting on the back end, and pulling it across the storage shelf before lifting may produce pressure cuts. As another example, dropping a wrapped tray (even a small distance) onto an edge of a cart or storage shelf while being transported to different areas of the hospital may produce pressure holes.

Generally speaking, the utilization of reinforcement elements reduces pressure hole formation for each of the barrier materials tested. Quantitatively, pressure hole formation is reduced between ~30% and 46%, depending upon what barrier material is tested and the basis weights of the barrier material and the reinforcement elements (corner guards).

When using reinforcement elements in conjunction with a relatively low basis weight barrier material (e.g., about 1 osy), low basis weight reinforcement elements (e.g., from about 0.1 to about 1 osy) result in substantial reduction in pressure hole formation in the barrier material. Further increasing reinforcement element basis weight (e.g., to a basis weight of from about 1 to about 2 osy) results in additional, but more modest, reduction in pressure hole formation in the barrier material. Further increasing the reinforcement element basis weight (e.g., to a basis weight of greater than about 2 osy) appears to provide little, if any, additional improvement in reducing pressure hole formation in the barrier material.

While the inventors should not be held to a particular theory of operation, a relatively "weak" barrier material (e.g., relatively low basis weight) which is not protected by a reinforcing element on the exterior of the barrier material (i.e., the outermost surface of the barrier material) will eventually fail at the same rate regardless of how "strong" (e.g., relatively high basis weight) the reinforcement elements are that might be used on an interior surface (i.e., the interior surface contacting the content to be sterilized or the sterilized content) of the barrier material.

When using reinforcement elements in conjunction with a moderate basis weight barrier material (e.g., basis weight about 1.8 osy), the use of low basis weight reinforcement elements (e.g., basis weights from about 0.1 to about 1 osy) on the interior surface of the barrier material (i.e., the interior surface contacting the content to be sterilized or the sterilized content) results in substantial reduction in pressure hole formation in the barrier material. A similar "plateau", where further increasing the basis weight of the reinforcement element on the interior surface no longer provides additional benefit to the barrier material is believed to exist.

Use of a relatively light weight reinforcement element (~1 osy) reduces pressure hole formation in all basis weights of barrier materials (barrier materials ranging from 1 osy to 2 osy). As the basis weight of the barrier material is increased, basis weight of the barrier material itself becomes the most predominant factor for reinforcement and reduced pressure hole formation. But light weight reinforcement elements still reduce pressure hole formation in the heaviest barrier materials tested (~2 osy), as compared to when reinforcement elements are not used. Extrapolation would suggest that a barrier material of 3 osy or greater would not benefit from a 1 osy reinforcement element.

Generally speaking, the results of this testing show that Percent Failure decreases as the basis weight of the barrier material is increased. However, when reinforcing elements are positioned between the sterilization tray and the barrier material, an increase in the basis weight of the combined components (i.e., the barrier material basis weight is constant and reinforcing element basis weight increases) results in a decrease in Percent Failure that levels off at a much higher rate of failure than for a barrier material having a corresponding basis weight.

Surprisingly, when reinforcing elements are positioned on the outside of the barrier material such that the reinforcing elements come between the barrier material and the surface of a shelf (at least at the corners of the sterilization tray), an increase in the basis weight of the combined components (i.e., the barrier material basis weight is constant and reinforcing element basis weight increases) results in a decrease in failure rates that compares favorably to a barrier material having a corresponding basis weight.

This is interpreted as providing a sterilization assembly in which the basis weight of the barrier panel may be reduced or at least held to a low level while generating a profile of resistance to pressure cuts and pressure holes that was previously provided only by increasing the basis weight of the entire sterilization wrap material.

EXAMPLES

Aspects of the disposable flexible multi-panel sterilization assembly were evaluated in the following examples.

Peel Test Procedure:

The resistance to peel force provided by the panel attachment means of the disposable flexible multi-panel sterilization assembly was evaluated utilizing the following peel test procedure:

1.2 This test is intended to determine the "Z" direction peel strength (bond strength) required to separate two barrier panels that have been overlapped and joined together utilizing panel attachment means.

1.3.1 If the panel attachment means are double-sided tape or a hook & loop-type fastening system or the like configured as shown in FIG. 8A and FIG. 9A, two approximately 254 by 152.4 mm (10 by 6 inch) barrier panel specimens are overlaid to sandwich a 101.6 by 25.4 mm (4 by 1 inch) specimen of a panel attachment means that is positioned at the center (i.e., away from the edges) of the overlaid barrier panels. During the engagement of the panel attachment means, a roller is rolled over the test specimen through three cycles in the direction of the "length" of the sample. The roller device weighs 4.5 pounds and includes a rubber coating around the roller. A suitable roller is part number HR-100 available from Chemsultants International, a business having a location in Mentor, Ohio. Adjacent ends of the overlaid barrier panels (i.e., the two ends on the same side edge of the overlaid barrier panel) are then respectively clamped into the two opposing grips of a tensile testing machine. Each end of the grip should be a distance of at least about 13 to 19 mm (0.5 to 0.75 inches) away from the panel attachment means joining the two overlaid barrier panels. The average load needed to completely separate the barrier panels as the grips move away from each other is determined. This is the bond strength of the specimen. Results are expressed in units of grams-force; higher numbers indicate a stronger, better bonded fabric.

1.3.2 If the panel attachment means is a fastener extending outward from or near a side of the barrier panel as shown in FIGS. 6, 7A and 7B, the distal end or portion measuring 101.6 by 25.4 mm (4 by 1 inch) of a fastener specimen (i.e., the end or portion that is unconnected to the barrier panel as shown in FIGS. 6, 7A and 7B) is joined to a barrier panel specimen. The proximal end or portion of the fastener (i.e., the end or portion that is pre-connected with the barrier panel as shown in FIGS. 6, 7A and 7B) is not joined. During the engagement of the panel attachment means, a roller is rolled over the test specimen through three cycles in the direction of the "length" of the sample. The roller device weighs 4.5 pounds and includes a rubber coating around the roller. A suitable roller is part number HR-100 available from Chemsultants International, a business having a location in Mentor, Ohio. The distal end/portion of the fastener specimen is manually separated from the barrier panel specimen for a distance of about 13 to 19 mm (0.5 to 0.75 inches) along the length of the specimen. The manually separated portion of the barrier panel specimen is then clamped into a grip of a tensile testing machine and the manually separated portion of the fastener specimen is then clamped into the other grip of a tensile testing machine. The average load needed to completely separate the component layers of the fastener from the barrier panel as the grips move away from each other is determined. This is the bond strength of the specimen. Results are expressed in units of grams-force; higher numbers indicate a stronger, better bonded fabric.

1.4 Definitions 1.4.1 average load: Average of the peaks collected in the specified peel region; i.e., between 25 and 178 millimeters.

1.4.2 delamination: The separation of the layers of material due to a failure of the attachment mechanism. Attachment strength is the tensile force required to separate barrier panels joined by panel attachment means under specified conditions.

1.4.3 Z-direction: Orientation perpendicular or normal to the plane of the material (i.e., the barrier panel).

1.5 This method references MTS TestWorks® for Windows software.

2.1 Verify the appropriate load cell is in the tensile tester. For load cell conditioning (warm up), refer to the manufacturer's specifications.

2.2 Ensure the appropriate grips are installed in the tensile tester. Ensure the grips and grip faces are free of build-up and the grip faces are free from dents or other damage.

2.3 Ensure the air pressure to operate the grips is not set beyond the manufacturer's maximum loading specifications.

2.4 Turn on the computer and then follow the software menu selection.

2.5 Follow the instructions for calibrating the load cell for the tensile tester being used.

2.6 Verify the tensile tester parameters meet the following specifications:

| | |
|---|---|
| Crosshead Speed | 305 ± 10 mm/minute (12 ± 0.4 inch) |
| Gage Length | 25.4 ± 1 mm (1 ± 0.04 inch) |
| Load Units | Grams-force |
| Full-Scale Load | 10-pound load cell |
| Test Result | Average load |
| Start Measurement | 25.4 ± 1 mm (1 ± 0.04 inch) |
| End Measurement | 177.8 ± 1 mm (7 ± 0.04 inch) |
| Endpoint | 21.6 cm (8.5 inches) |

3.1 Cut a 4 inch by 1 inch specimen of the panel attachments and proceed according to Step 1.3.1 or Step 1.3.2. Specimens should be handled minimally and be free of folds, wrinkles, or creases.

4.1 Place the specimens in the grips according to Step 1.3.1 or 1.3.2.

4.1.1 Mount the free end of one specimen into one grip and the free end of the other specimen into the other grip such that the bonded junctures of the specimens are centered and there is no slack. Do not clamp the specimens at an angle.

4.2 Start the crosshead.

4.3 Run the test until the specimens have completely separated (i.e., delaminated). Do not push the return button or otherwise stop the test until the specimen has been completely pulled apart.

4.4 Record the average load in grams-force.

4.5 Remove the specimens.

4.6 Repeat for the remaining specimens.

5.1 Report the average load to the nearest 0.1 gram-force for each individual test of specimens.

5.2 Calculate the average for all the specimens and report this as the sample value.

6.1 Tensile Tester

Constant-Rate-of-Extension (CRE) tensile tester with a computer-based data acquisition and frame control system 6.2 Load Cell Choose the appropriate type for the tensile tester being used. Use a load cell in which the majority of the peak load results fall between 10 and 90% of the capacity of the load cell. Obtain 6.1-6.2 from Instron Corporation, Canton, Mass. 02021, OR MTS Systems Corporation, Eden Prairie, Minn. 55344-2290.

6.3 Load Cell Adapter 15.9 mm upper—if needed.

6.4 Universal Joint 6.4.1 Optional: Sintech small load cellswivel

1/4-28 UNC male stud one side, 1/4-28UNC female thread opposite side, rated for 75 lbs.

6.4.2 Optional: Sintech universal load cellswivel

1/4-28 UNC male stud one side, 12.7 mm (0.50 inch) female socket other side, rated for 300 lbs 6.4.3 Optional: Synergy load cell adapterswivel 15.88 mm (0.625 inch) male socket to 12.7 mm (0.50 inch) female socket, rated for 300 lbs.

6.6 Computer Data Acquisition and Control System for Tensile Tester

Example: MTS TestWorks® for Windows, or equivalent.

6.7 Test Macro

For use with MTS TestWorks® forWindows software version 4.0 OR Instron Bluehill software;

6.8 Grips and Faces

Pneumatic 6.8.1 Top and Bottom Grips

Side-action, manual air switch; example: Instron Corporation part number 2712-003, or equivalent AND 6.8.1.1 Grip Faces 25.4 by 76.2 millimeter (1 by 3 inch) faces, rubberized, top and bottom; example: Instron Corporation part number 2702-035, or equivalent OR 6.8.2.1 Standard Capacity Grips and Faces Top and bottom—use standard capacity grips and faces combination designed for a maximum load of 5000 grams. If the results approach this limit, observe the material being tested. If slippage is noticed, use the Instron grips and faces that have a 90.7-kg maximum load rating.

7.2 Laboratory conditions: Maintain a controlled testing environment of 23±2° C. and 50±5% relative humidity.

Shear Test Procedure:

The resistance to shear force provided by the panel attachment means of the disposable flexible multi-panel sterilization assembly was evaluated utilizing a test procedure substantially identical to the Peel Test Procedure set forth above, but with the following differences:

(i) A 50-pound load cell was used instead of a 10-pound load cell.

(ii) In Step 1.3.1, the samples are oriented parallel to the plane of travel of the grips and the opposite ends of the overlaid barrier panels (i.e., the two ends on the opposite side edges of the overlaid barrier panel) are clamped into each grip of a tensile testing machine;

(iii) In Step 1.3.2, the distal end/portion of the fastener specimen is manually separated from the barrier panel specimen for a distance of about 13 to 19 mm (0.5 to 0.75 inches) along the length of the specimen. The samples are oriented parallel to the plane of travel of the grips. The manually separated portion of the barrier panel specimen is then clamped into a grip of a tensile testing machine and the manually separated portion of the fastener specimen is then clamped into the other grip of a tensile testing machine.

(iv) The Peak Load needed to completely separate the specimens as the grips moved away from each other was measured instead of the Average Load.

Example 1

Time and Motion Study

Test Subject Selection and Testing Sequence

A random population of 57 individuals with no or minimum healthcare experience were selected for this study. These individuals were randomly assigned to one of the two wraps for testing of the training and wrapping/unwrapping. The pre-requisite for their selection was limited to not having any prior experience in a hospital's central sterilization department. The reason for this pre-requisite is that people with central sterilization experience may have already been exposed to the use of surgical wraps and therefore would not be acceptable for testing related to training.

With regards to the testing sequence the first test was for the time/ease of training. Once an individual was trained and considered proficient at the use of one of the two surgical wraps that person became eligible for testing of the wrapping/unwrapping.

Training Test—Time Required to Learn Wrap Procedure

This training test was directed to the learning curve and time requirements for a subject to be trained and to become proficient in wrapping and unwrapping one type of sterilization wrap.

The test to gauge time requirements for training an individual in wrapping began with a proficient trainer providing an overview demonstration of the wrap and the various types of equipment involved. He or she then provided a detailed, step-by-step demo of how the wrap was used in practice to the test subject and answered any questions. The next step involved one last demonstration of wrapping and unwrapping a tray straight through before handing off the session to the test subject. The test subject continued attempting to successfully wrap and unwrap a tray with supervision and feedback. For every mistake made, as outlined by the trainer, the test subject started the process over again from the beginning. Trainers provided guidance and coaching until a test subject could successfully wrap a surgical tray five times sequentially without any errors, missed steps, and/or feedback from his or her trainer. This point marked the end of the test. Once a subject could demonstrate his or her ability and proficiency to successfully wrap trays, they were deemed a "proficient" test subject.

As mentioned above each test subject was trained on one type of wrap to eliminate any advantage he or she may have gained from previous experience of using the other type of wrap. This also maintained independence between the two sample sets. Finally, a particular wrap was not used for more than three attempts during training. KimGuard® One-Step® wraps were flipped for a change in orientation after every attempt and Multi-panel sterilization assemblies had release liners reapplied after every attempt.

Wrap and Unwrap Time

In order to test the wrap time, a pool of proficient subjects in wrapping trays with both the multi-panel sterilization assembly and KimGuard® One-Step® wrap was selected. As previously mentioned these subjects were identified during the training testing.

During wrap and unwrap time testing, the subjects were required to continuously wrap and unwrap a single size surgical tray with the following approximate dimensions: length=20 inches, width=10.5 inches and height=3.5 inches (the most common tray size used in hospitals). Wraps were discarded after each use (wrap and unwrap) to prevent testers from taking advantage of placement marks that could be created in the wrap after it was used. This ensured independence between the tests. For timing purposes the start of the wrapping process was when the wrap was fully opened on top of the wrapping table, and the tester was holding the surgical tray in his or her hands. The end of the wrapping process was when the tray was fully wrapped and taped, and the tester stepped back from the wrapping table. On the other hand, the start of the unwrapping process was when the tester first touched the wrap to unwrap the tray, and the end when the tray was fully exposed on top of the open wrap and the tester stepped back from the wrapping table.

If during the wrapping or unwrapping process the subject did not follow the standard processes, the sample was not considered valid and the test repeated.

Statistical Analysis Methodology

In designing the statistical analysis for each one of the two tests, it was assumed the time it takes to wrap and unwrap and train personnel for both wraps were independent and normally distributed. The approach taken to analyze each of the two tests was to define a 95% confidence interval on the difference between the means of labor time requirements for each wrap. The confidence interval indicated if there was a statistical difference between the two mean times for each one of the two test, and if there was one, it determined what that difference was.

For each of the two tests, the mean time it takes to wrap/unwrap or train personnel using the KimGuard@ One-Step® wrap was denoted $\mu_1$ and the mean time it takes using the multi-panel sterilization assembly was denoted as $\mu_2$. The variances were denoted $\sigma_1^2$ and $\sigma_2^2$ respectively. For this study, both the means and variances were unknown.

For each one of the two tests, random and independent time and motion studies of sample size $n_1$ and $n_2$ were taken for the KimGuard® One-Step® wrap and multi-panel sterilization assembly respectively. Sample mean times were denoted as $xbar_1$ and $xbar_2$, and sample variances as $s_1^2$ and $s_2^2$. To construct a 95% confidence interval on $\mu_1-\mu_2$ a pooled estimator was first calculated as follows:

$$S_p^2 = [(n_1-1)s_1^2 + (n_2-1)s_2^2]/(n_1+n_2-2)$$

Then, a 95%, $100(1-\alpha)$, two-sided confidence interval on $\mu_1-\mu_2$ was determined utilizing the t statistic and distribution with degrees of freedom of $n_1+n_2-2$, and the following theorem:

$$xbar_1 - xbar_2 - t_{\alpha/2, n_1+n_2-2} \times s_p \times [(1/n_1)+(1/n_2)]^{0.5} \leq \mu_1 - \mu_2 \leq xbar_1 - xbar_2 - t_{\alpha/2, n_1+n_2-2} \times s_p \times [(1/n_1)+(1/n_2)]^{0.5}$$

The range, difference between means, obtained from this analysis statistically validated the differences between the labor time requirements for each one of the two tests stated above.

Sample Size Determination

Sample sizes for the two tests during the time and motion testing was determined based on analyzing initial estimates of specified error between population and sample means, standard deviations of the independent sets of samples, and initial confidence interval requirements. From this initial analysis, appropriate sample sizes were determined utilizing the following statistical theorem:

$$n = [(Z_{\alpha/2}\sigma)/e]^2$$

n=appropriate sample size z=test statistic under the null hypothesis that can be approximated by a normal distribution α=required confidence level, e.g. 95%

σ=estimated standard deviation of sample sets e=specified error: |xbar−μ|

The α and e values control the level of precision required for the estimated mean labor time required by each wrap in each of the two tests. A 95% confidence level (α) and a ±10% error (e), were the minimum acceptable values for the sample size precision controls used in all of the tests.

Wrapping and Unwrapping Standard Procedures
KimGuard® One-Step® Wrapping Standard Procedures
This procedure is generally illustrated in FIGS. 4A to 4E.
Step 1—Lay Wrapper on Table
Step 2—Position Instrument Tray
Step 3—Fold Bottom Over to Completely Cover Tray
Step 4—Check to Make Sure Corners are Covered
Step 5—Fold Handle Back
Step 6—Hold Handle in Place with Elbow
Step 7—Gather One Side
Step 8—Fold Side
Step 9—Fold Side Handle Back
Step 10—Hold Handle with Elbow and Gather Opposite Side
Step 11—Fold Side
Step 12—Fold Opposite Side Handle Back
Step 13—Hold Handles with Elbows and Grab Top
Step 14—Gather Top to Create Final Flap
Step 15—Bring Final Flap Over Package
Step 16—Spread Sides of Top so Whole Package is Covered
Step 17—Tuck to Create Opening Handle
Step 18—Secure with Tape Step 1 (first piece of tape across tucked final flap)
Step 19—Secure with Tape Step 2 (second piece of tape across tucked final flap)
Step 20—Secure with Tape Step 3 across entire width of package to seal each side
Done
KimGuard® One-Step® Unwrapping Standard Procedures
Step 1—Break Long Tape on Each Side Step 1 &2 (i.e., break tape applied in Wrapping Step 20 at each side of package)
Step 2—Break Tape Step 3 (i.e., break tape applied in Wrapping Step 18 across tucked final flap)
Step 3—Break Tape Step 4 (i.e., break tape applied in Wrapping Step 19 across tucked final flap)
Step 4—Grab Opening Handle (i.e., handle created in Wrapping Step 17)
Step 5—Pull Handle Towards You
Step 6—Unfold Top Layer Away From You
Step 7—Grab Side Handle and Pull to the Side (i.e., handle created in Wrapping Step 12)
Step 8—Grab Other Side Handle and Pull to Side (i.e., handle created in Wrapping Step 9)
Step 9—Grab Final Fold Handle (i.e., handle created in Wrapping Step 5)
Step 10—Pull to Open Final Fold
Done
Multi-Panel Sterilization Assembly Wrapping Standard Procedures
This procedure is generally illustrated in FIGS. 9A to 9E.
Step 1—Lay Multi-Panel Sterilization Assembly on Table
Step 2—Position Instrument Tray
Step 3—Fold Bottom Over to Completely Cover Tray
Step 4—Remove Release Liner from one Side Exposing Adhesive on Pre-Attached Tape (i.e., Panel Attachment Means)
Step 5—Gather One Side
Step 6—Fold Side & Secure Pre-Attached Tape (i.e., Panel Attachment Means)
Step 7—Remove Release Liner from Other Side Exposing Adhesive on Pre-Attached Tape (i.e., Panel Attachment Means)
Step 8—Gather Opposite Side
Step 9—Fold Side & Secure Pre-Attached Tape (i.e., Panel Attachment Means)
Step 10—Gather Final Flap at Top (i.e., Fold Protection Panel)
Step 11—Bring Final Flap Over Package
Step 12—Fold Edge Under Final Flap
Step 13—Secure with Tape Step 1 (first piece of tape across tucked final flap)
Step 14—Secure with Tape Step 2 (second piece of tape across tucked final flap)
Done
Multi-Panel Sterilization Assembly Unwrapping Standard Procedures
Step 1—Break Tape Step 1 (i.e., break tape applied in Wrapping Step 13 across tucked final flap)
Step 2—Break Tape Step 2 (i.e., break tape applied in Wrapping Step 14 across tucked final flap)
Step 3—Unfold Top Layer (i.e., Fold Protection Panel) Away From You
Step 4—Grab Sides Using Two Hands
Step 5—Peel Tape (i.e., Panel Attachment Means) to Unfold Sides
Step 6—Grab Opening Handle (i.e., Pull Tab) at Label
Step 7—Lift Label Up
Step 8—Pull Towards You
Done Test Results
Wrap and Unwrap Time The following data summarizes the statistical results of testing for wrapping and unwrapping time with the KimGuard® One-Step® wrap and multi-panel sterilization assembly.

TABLE 1A

Wrapping Time

| | KimGuard ® One-Step ® Wrapping Procedure | Multi-Panel Sterilization Assembly Wrapping Procedure |
|---|---|---|
| Sample Size Collected | 82 | 95 |
| Sample Mean | 1 min 43 sec | 32 sec |
| Sample Standard Deviation | 36 sec | 7 sec |
| Specified Error | 10.3 sec (10%) | 3.2 sec (10%) |
| Minimum Sample Size Required | 80 | 31 |

The statistical difference between the mean wrapping times for the KimGuard® One-Step® wrap and the multi-panel sterilization assembly was determined from the data summarized above. With a 95% confidence level, the actual difference between the labor time requirements for the two wraps falls in the following range: $1.06 \text{ minutes} \leq \mu_1 - \mu_2 \leq 1.3$ minutes. Because this range does not include zero, it can be inferred that wrapping labor requirements for the KimGuard® One-Step® wrap are statistically greater than those for the multi-panel sterilization assembly.

TABLE 1B

Unwrapping Time

| | KimGuard ® One-Step ® Unwrapping Procedure | Multi-Panel Sterilization Assembly Unwrapping Procedure |
|---|---|---|
| Sample Size Collected | 82 | 95 |
| Sample Mean | 15.8 sec | 5.6 sec |

TABLE 1B-continued

| | Unwrapping Time | |
|---|---|---|
| | KimGuard ® One-Step ® Unwrapping Procedure | Multi-Panel Sterilization Assembly Unwrapping Procedure |
| Sample Standard Deviation | 3.0 sec | 1.5 sec |
| Specified Error | 1.6 sec (10%) | 0.6 sec (10%) |
| Minimum Sample Size Required | 15 | 29 |

Statistical Results

The statistical difference between the mean unwrapping times for the KimGuard® One-Step® wrap and multi-panel sterilization assembly was determined from the data set collected above. With a 95% confidence level, the actual difference between the labor time requirements for the two wraps falls in the following range: 9.5 seconds$\leq \mu_1 - \mu_2 \leq$10.9 seconds. Because this range does not include zero, it can be inferred that unwrapping labor requirements for the KimGuard® One-Step® wrap are statistically greater than those for the multi-panel sterilization assembly.

Training Test—Time Required to Learn Wrap Procedure

The following data summarizes the statistical results of testing for training time with the KimGuard® One-Step® wrap and multi-panel sterilization assembly.

TABLE 1C

| | Training Time | |
|---|---|---|
| | KimGuard ® One-Step ® Unwrapping Procedure | Multi-Panel Sterilization Assembly Unwrapping Procedure |
| Sample Size Collected | 21 | 36 |
| Sample Mean | 42.4 min | 20.8 min |
| Sample Standard Deviation | 8.4 min | 6.1 min |
| Specified Error | 4.3 min (10%) | 2.1 min (10%) |
| Minimum Sample Size Required | 16 | 33 |

Statistical Results

The statistical difference between the mean training times for the KimGuard® One-Step® wrap and multi-panel sterilization assembly was determined from the data set collected above. With a 95% confidence level, the actual difference between the training labor time requirements for the two wraps falls in the following range: 17.7 minutes$\leq \mu_1 - \mu_2 \leq$25.5 minutes. Because this range does not include zero, it can be inferred that training labor requirements for the KimGuard® One-Step® wrap are statistically greater than those for the multi-panel sterilization assembly.

CONCLUSIONS

Wrap and Unwrap Time
Wrapping

With an average wrapping time of 1 minute 43 seconds for the KimGuard® One-Step® wrap and an average wrapping time of 32 seconds for the Multi-panel sterilization assembly, test results establish an average 68% reduction in time when comparing the two wraps. This observed reduction in time is a result of various factors. Wrapping surgical trays using the multi-panel sterilization assembly provides a more simple and intuitive technique for its user compared to its counterpart. There are fewer, less complex steps as well as fewer touches required to wrap a tray. The multi-panel sterilization assembly features reference lines (i.e., pre-determined fold lines) for initial accurate placement of trays, pre-attached release liner adhesives and less material to handle. Furthermore, sealing a wrapped tray with tape using the multi-panel sterilization assembly takes on average 6.2 seconds compared to the 18.2 seconds required on average for the KimGuard® One-Step® wrap. This is due to not having to seal the top of the tray (across the multi-panel sterilization assembly) with tape.

If the final taping process is excluded from the wrapping process (See Wrapping Steps 18, 19 and 20 for the KimGuard® One-Step® wrap and Wrapping Steps 13 and 14 for the Smart-Fold package) the average wrapping time is 1 minute 25 seconds for the KimGuard® One-Step® wrap and 26 seconds for the multi-panel sterilization assembly. That represents an average 69% reduction in wrapping time.

Unwrapping

The KimGuard® One-Step® wrap, on average, takes 15.8 seconds to unwrap in comparison to the multi-panel sterilization assembly, which takes 5.6 seconds. This drop in unwrapping time represents an average 64% reduction in time. This reduction is the result of less sealing tape required to be broken for the multi-panel sterilization assembly (i.e. two breaking points rather than four from KimGuard® One-Step® wrap) and a less complex procedure that allows simultaneous movements without directly coming into contact with the surgical tray.

Training—Time Required to Learn Wrap Procedure

Training end users on the proper standard operating procedures to wrap and unwrap trays requires, on average, 42.4 minutes for the KimGuard® One-Step® wrap and 20.8 minutes for the Multi-panel sterilization assembly. The reason for this 51% decrease in time similarly reflects the points outlined in the wrapping and unwrapping hypothesis discussed above. The more intuitive, less complex, fewer steps, and ergonomic configuration effectively allowed users to more quickly learn and demonstrate proficiency in proper wrapping and unwrapping techniques for the multi-panel sterilization assembly compared to the KimGuard® One-Step® wrap.

Example 2

An exemplary disposable flexible multi-panel sterilization assembly 100 was constructed to have five sides or edges. This geometry is generally as illustrated in FIG. 6. A second edge 122 of the barrier panel 102 of the multi-panel sterilization assembly is approximately 36 inches in length. A first edge 120 and a third edge 124 of the barrier panel 102 are perpendicular to the second edge 122 and are each approximately 35 inches long. A first edge 146 and a second edge 148 of the fold protection panel 108 are each approximately 19 inches long and come together at an obtuse angle (not necessarily as depicted in FIG. 6). The first edge 146 and second edge 148 of the fold protection panel 108 are directly across from the 36 inch long edge bottom edge 122 of the barrier panel 102. This design covers a typical sterilization tray having about 700 square inches of surface area for sterile processing when the sterilization tray is placed in the content receiving region 130 and the bottom edge 122 is folded up and over to cover the top of the tray.

The panel attachment means 106 which may be in the form of two pre-attached tape tabs are used to pull the first edge 120 and third edge 124 of the barrier panel 102 over the top of the tray and then tape the edges down onto the back of the sheet already folded over the top of the tray. The use of these tabs enables the design to use a much shorter length while confidently taping down the side folds when preparing the tray for sterilization. Furthermore, the use of these tabs will facilitate the wrapping process making it both easier and faster to prepare a tray for sterile processing. After folding over and taping down the sides of the wrap, the top of the wrap is then folded over the top of the tray and the preparer of the tray can then tuck the top corner of the wrap back under and the out with a z-fold creating a pull point on the wrap for aseptic opening in the operating room.

The surface area of this design is just 1260 square inches meaning that just 1.8 square inches of barrier panel is needed to cover each square inch of tray surface. In addition to a shaped design reducing material needed to wrap an instrument tray, the design provide two layers of sterilization fabric (i.e., barrier panel) only where it is necessary to cover each square inch of the surface area of an instrument tray. Two layers are generally the configuration needed to provide a sufficient microbial barrier. Therefore, the additional surface area of material used to wrap a sterilization tray need not serve as a microbial barrier. As a result, it can simply be a single layer of material—that is, a fold protection panel.

Example 3

Conventional wrapping systems sequentially utilize single ply sterilization wrap or utilizing a two-ply sterilization wrap (e.g., KimGuard® One-Step® sterilization wrap) to fold around a standard tray. It is generally thought that excess material that overlaps and provides multiple folds, plies or layers at the top or upper region of the wrapped package is needed to maintain a sterile barrier.

This example illustrates the reduction in the number of plies, layers or folds of material on the top or upper region of a standard tray when wrapped utilizing the multi-panel sterilization assembly. Compared to a standard tray that is wrapped using a conventional wrapping system, the multi-panel sterilization assembly provides far fewer plies, layers or folds on the top or upper region while maintaining the tortuous path requirements generally thought necessary to provide a sterile barrier. This example also describes a method of sectioning a wrapped package containing a standard article (i.e., a sterilization tray having approximate dimensions of length=20 inches (~510 mm), width=10.5 inches (~270 mm) and height=3.5 inches (~88 mm) that allows for differences in the wrapped configurations to be measured.

Conventional sterilization wrapping uses two (2) similarly sized superposed sheets to wrap articles, via either the envelope fold method (See FIGS. 4A to 4E) or the square fold method (See FIGS. 5A to 5E). Such superposed sheets are sheet plies 14 and 16 of FIG. 1. Suitable barrier materials are single ply sterilization wraps and Table 2 lists examples and their characteristic basis weights in terms of ounces per square yard and Frazier permeability in terms of CFM at a pressure differential of 125 Pa as determined from 3 inch diameter specimens in accordance with ISO 9237:1995 (measured with an automated air permeability machine using a 38 cm$^2$ head at a test pressure of 125 Pa,—exemplary air permeability machine is TEXTEST FX 3300 available from TEXTEST AG, Switzerland). These sterilization wraps are currently sold by Kimberly-Clark Corporation (Dallas, Tex.).

TABLE 2

| Single Ply Sterilization Wraps | Basis Weight | Frazier permeability Average* | Standard Deviations, +/− |
|---|---|---|---|
| KC100 | 1.05 osy (~35 gsm) | 37.84 | 1.0469 |
| KC200 | 1.20 osy (~40 gsm) | 66.44 | 3.13234 |
| KC300 | 1.40 osy (~47 gsm) | 52.68 | 5.552537 |
| KC400 | 1.85 osy (~62 gsm) | 37.13 | 1.120565 |
| KC500 | 2.05 osy (~68 gsm) | 30.91 | 0.792254 |
| KC600 | 2.57 osy (~86 gsm) | 25.99 | 1.395588 |

*Average values are based on 10 specimens for each sample.

Figure 19:
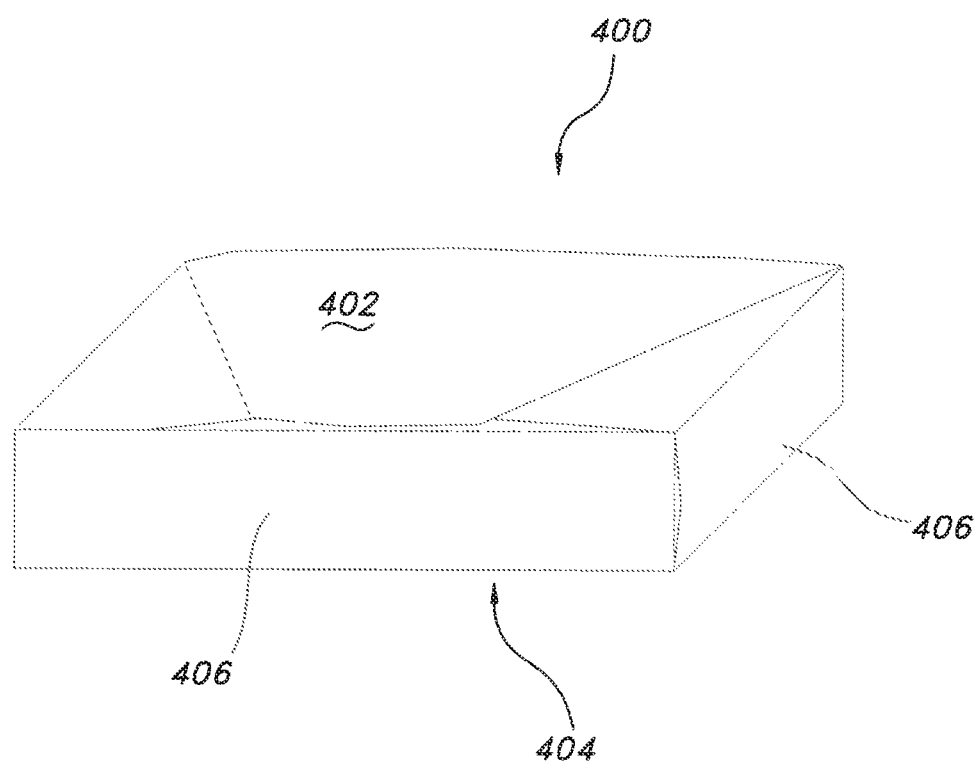
FIG. 19 is an illustration that identifies regions of a package formed by wrapping an article wrapped with conventional sterilization wrap.

These conventional wraps create large expanses of overlapping materials that restrict air flow permeability (Permeability) in addition to the inherent restriction of the unfolded sterilization wraps themselves. The overlapping folds corresponding add weight through accumulated stacked plies/layers in excess of that necessary to ensure adequate barrier protection and establishment of the desired tortuous path. These overlaps tend to concentrate in specific regions dictated by the folding patterns used to wrap articles. In wrapping box-like articles, e.g. surgical trays, the wrapping mimics the box-like shape and presents distinct Top, Bottom, and Side Strip regions as definable specific regions. FIG. 19 illustrates the Top region 402, the Bottom region 404, and Side Strip region 406.

Figure 25:
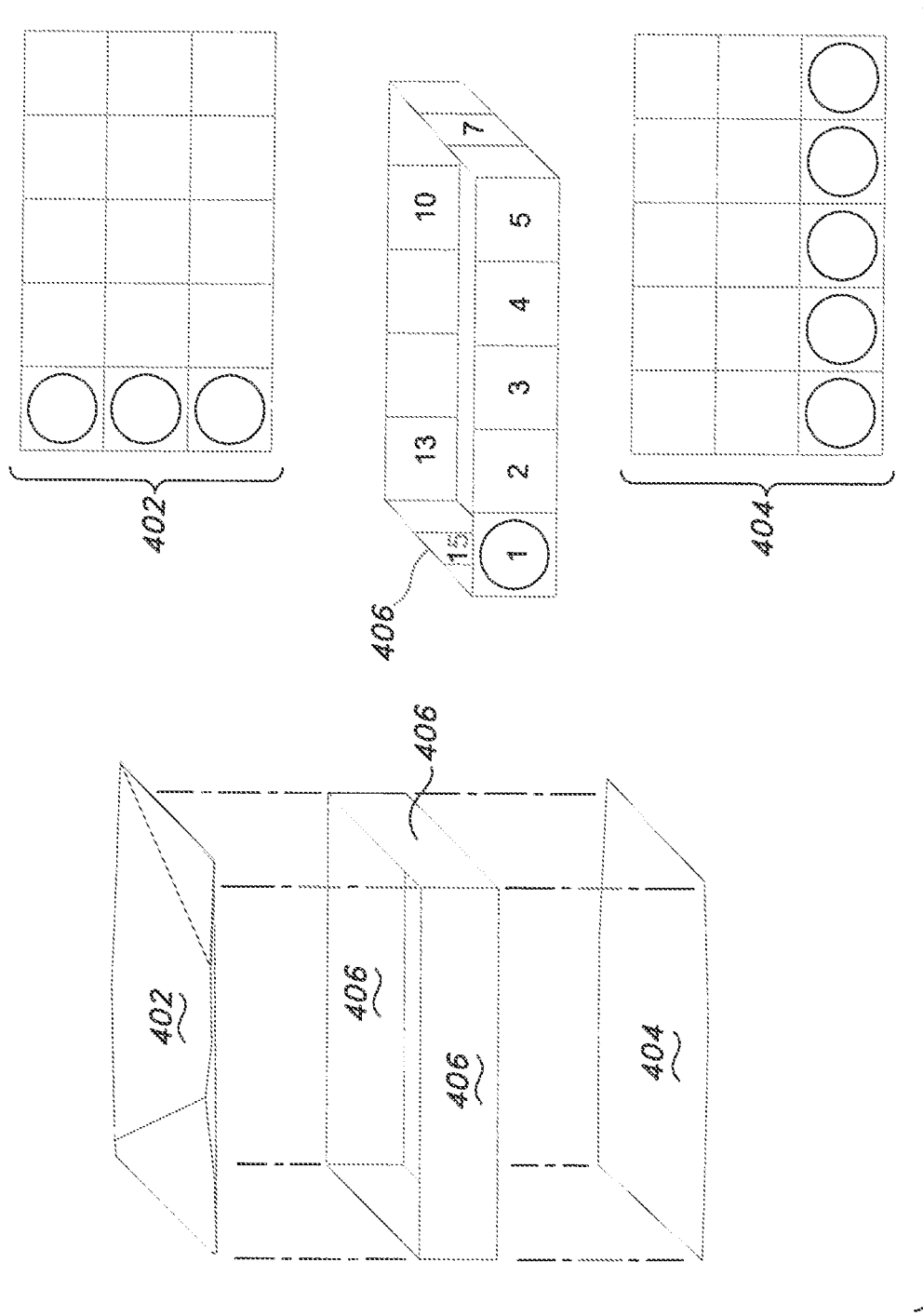
FIG. 25 is an illustration showing separated regions of a wrapped article according to FIG. 20 or 23, their respective sectioned arrays, and location of specimens within the arrays.

When the invention uses barrier panels composed of two (2) layers or plies, which is the number of layers or plies commonly used conventional wrap systems, the present invention when configured around the tray consistently reduces in the Top region 402 (i) the number of stacked plies, (ii) the amount of material, and (iii) the resistance to air flow (and hence sterilant gas such as, for example, steam or ethylene oxide) as compared to conventional sterilization wrap systems. These reductions are demonstrated by sectioning the wrappings from around wrapped trays into separated Top, Bottom and Side Strip regions and sampling these regions for subsequent measurements as indicated in FIG. 25 to obtain profile representations of air flow permeability, weight and the maximum number of stacked plies. From such representations, the advantages of the invention in reducing the number or amount of folds and the amount of material needed to wrap an article, even with the inclusion of any reinforcement elements, are connected to quantifiable measurements that include Frazier Permeability (Permeability, CFM), weight per 3-inch diameter specimen area (Wgt, gms), and a count of the maximum number of stacked plies in the 3-inch diameter specimen area (Plies). These measurements made in Top, Bottom and Side Strip regions are subsequently presented via FIGS. 26-42 and Tables 5-19 for the multi-panel sterilization assembly of the present invention and for conventional sterilization wrap systems that use the envelope folding method. Two sheets, layers or plies of barrier material are utilized for the conventional sterilization wrap and corresponding constructions are used in the barrier panels of the present invention to provide a more direct comparison.

Conventional sterilization wrap is folded about a conventional sterilization tray utilizing the envelope fold method rather than the square fold pattern in making the comparison to the multi-panel sterilization assembly through quantitative measurement for two reasons: (i) the envelope fold pattern is much more prevalent in use; and (ii) the square fold pattern creates overlaps in material that are explainable and quantifiable without the need of measurements in order to compare to the invention (the envelope fold pattern creates more complex overlaps). As is subsequently shown and discussed, the Top region of the wrapping around an article is the region where distinctions among the wrapping systems are greatest. The Bottom region has the least distinctions, and those of the Side Strip regions are less clear. Because articles are typically constructed to emit and vent sterilant gases through the Top and Bottom regions, and since the Side Strip regions tend to be solid supporting walls, the distinctions among wrapping systems in the Top region are of particular relevance. Moreover, the Top region is where the edges of conventional sterilization wrap are gathered/folded together to provide potential openings or pathways through the barrier material that are conventionally believed to be overcome by employing excess, overlapping wrap material.

Before addressing the amount/number of overlapping plies or layers of material for the multi-panel sterilization assembly of the present invention and for conventional wrapping systems utilizing the envelope fold method, the following discussion will address the amount/number of overlapping plies or layers of material for conventional wrapping systems utilizing the square fold method. Referring generally to FIGS. 5A-E, the minimum amount/number of overlapping plies or layers of material resulting from wrapping a conventional sterilization tray or other box-like article using the square fold method is determined as the minimum number of stacked plies in the Top region of the wrapped article. For each conventional sheet of sterilization wrap used in the square fold method:

- one (1) ply results from a first fold of the bottom end 66 over an article (62),
- at least one (1) ply results from folding the top end 70 over the article, and
- at least three (3) plies result from folding the left side end 72, which has ply contributions from the bottom and top end folds, over the article.

Thus, each separate sheet of sterilization wrap folded around a box-like article using the square fold method contributes at least five (5) stacked plies in the Top region 402 (see FIG. 19). This minimum count of stacked plies excludes any back-folding of the bottom, top and left side ends 66, 70, 72, as conventionally done and also excludes any contributions from folding over the right side end 74 that completes the wrapping. This minimum of five (5) stacked plies per separate sheet of sterilization wrap is doubled to ten (10) plies when two (2) sheets of sterilization wrap are used—either sequentially or simultaneously. For a given construction of a sheet of sterilization wrap, the minimum weight and the air permeability through the stacked plies can be determined from the properties of the sheet of sterilization wrap (e.g., those for basis weight and Frazier permeability) given in Tables 2 and 3, and from the number of stacked plies or layers.

As is subsequently shown, this minimum ten (10) stacked plies/layers in the Top region for wrapping with two (2) sheet of sterilization wrap using the square fold method exceeds those of the invention having a barrier panel composed of two (2) layers or plies and a fold protection panel composed of one (1) or even two (2) layers or plies. The square fold wrapping method or pattern provides a number of stacked plies in the Bottom region that are the same as those for the envelope fold wrapping method or pattern, and which are also similar to the number provided in the Bottom region 404 (see FIG. 19) by the multi-panel sterilization assembly. With respect to the Side Strip region 406 (see FIG. 19), the overlap of conventional sterilization wrap material in a square fold wrapped article is expected to yield similar ply stacking as an envelope fold wrapped article and an article wrapped using the multi-panel sterilization assembly given the nature of all these folding systems to fold for aseptic unfolding after sterilization from the Top region.

Figure 14:
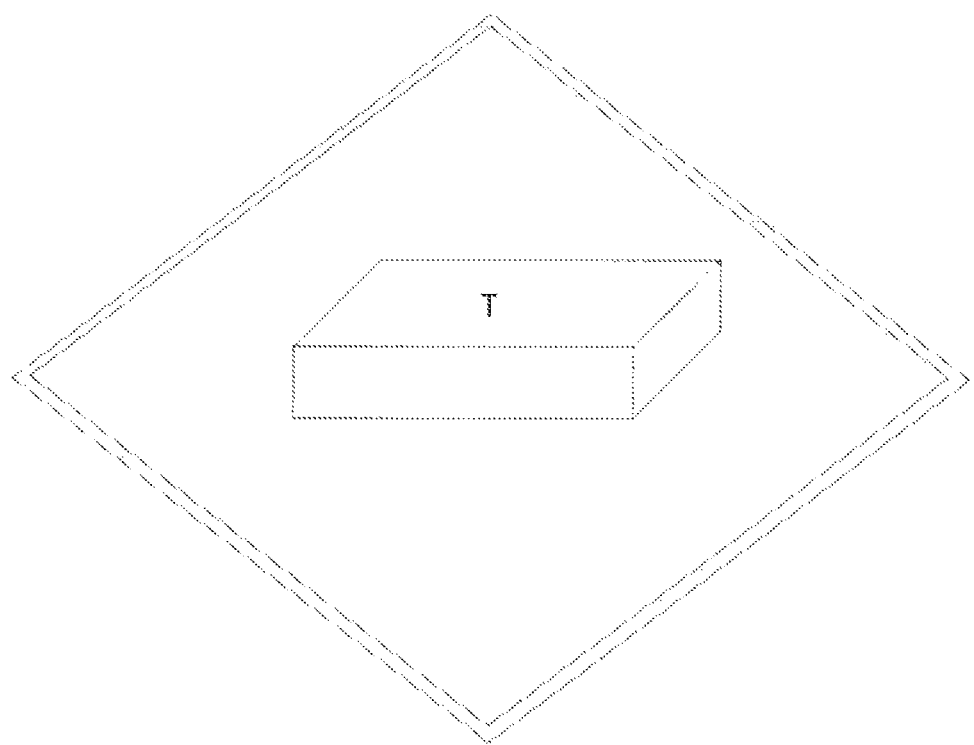
FIG. 14 is an illustration of an article positioned on conventional sterilization wrap in preparation for simultaneously wrapping both panels using a conventional envelope fold.
Figure 16:
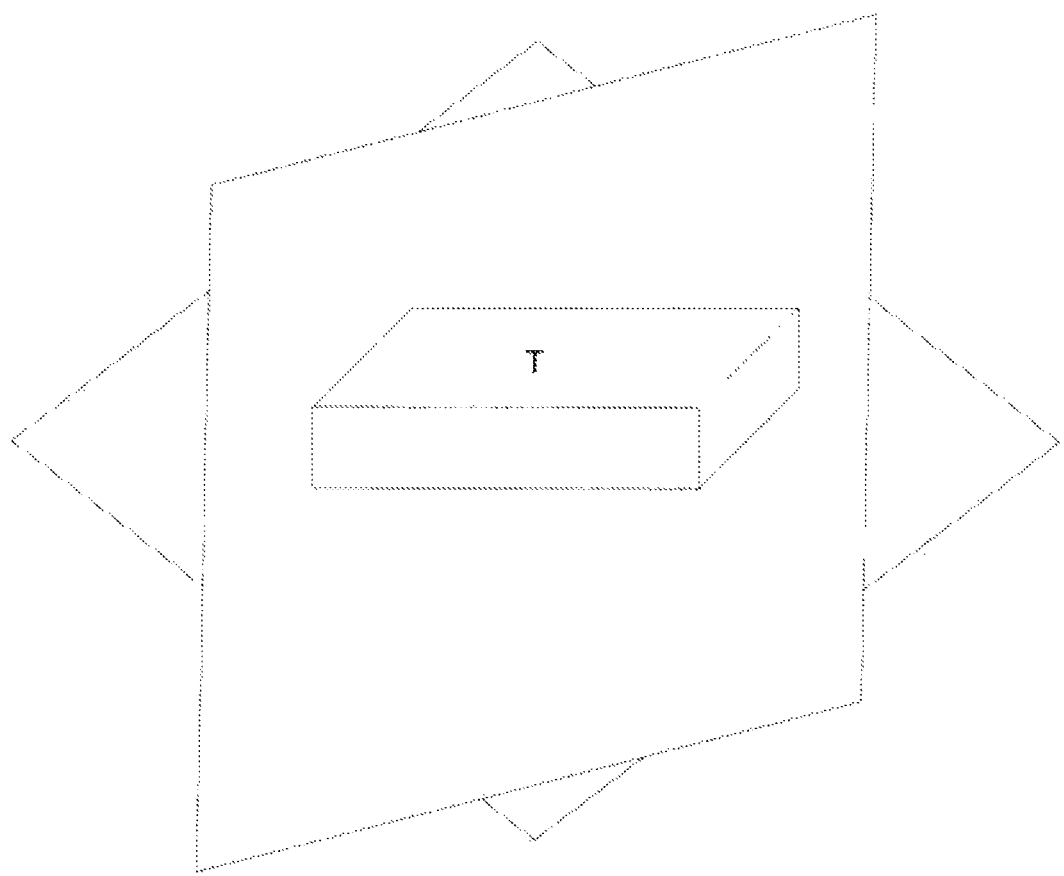
FIG. 16 is an illustration an article positioned on two superposed but non-aligned sheets of conventional sterilization wrap in preparation for wrapping each panel sequentially using a conventional envelope fold.
Figure 21:
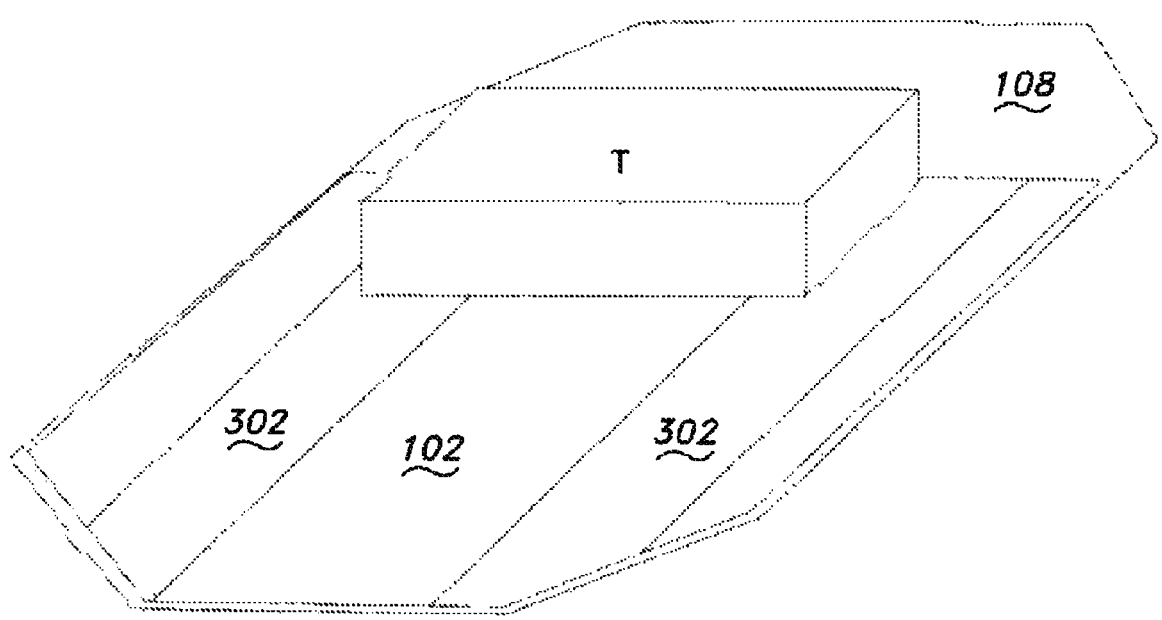
FIG. 21 is an illustration is an article positioned on an exemplary multi-panel sterilization assembly.
Figure 22:
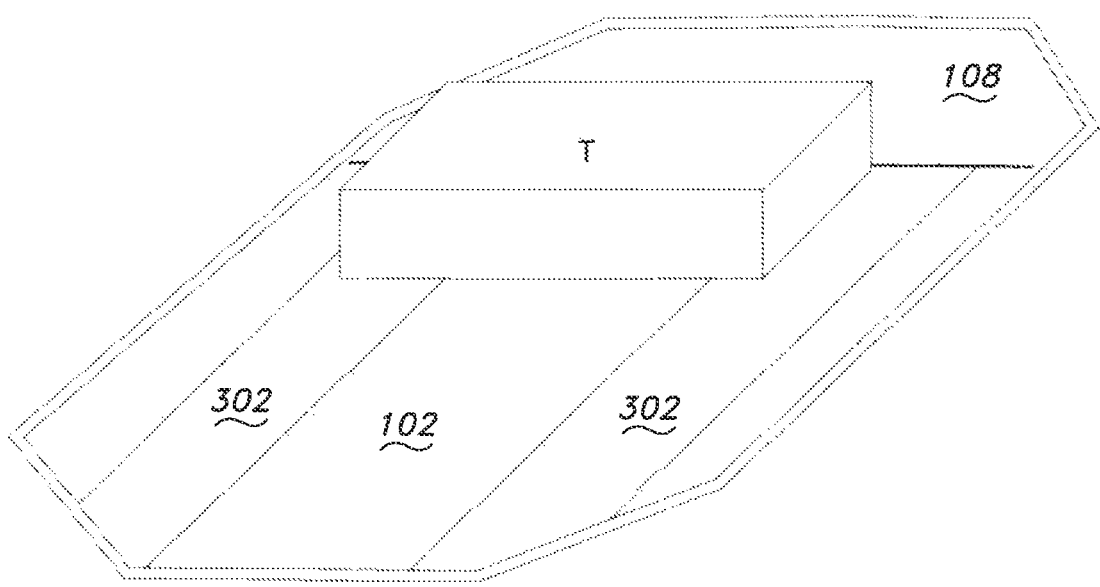
FIG. 22 is an illustration is an article positioned on another exemplary multi-panel sterilization assembly.

The embodiments of the multi-panel sterilization assembly of the present invention previously discussed for FIG. 8A, FIGS. 9A-E, and FIG. 13 are used to represent the quantification of the wrapping per the invention and specific representative embodiments are illustrated in FIG. 21 with the fold protection panel 108 having one (1) ply and FIG. 22 with the fold protection panel 108 having two (2) plies. This example compares these embodiments with conventional sterilization wrap systems that utilize the envelope fold pattern or technique and which are illustrated in FIG. 14 and FIG. 16. Thus, in order to provide a direct comparison, the conventional sterilization wrap systems and the multi-panel sterilization assembly use two (2) layers, plies or sheets of material. Representative constructions of superposed sterilization wrap that involving stacking two (2) plies of Sterilization Wrap of the type listed in Table 2 yield Permeability values given in the following Table 3:

TABLE 3

| Barrier Panel Construction | Frazier permeability | |
| --- | --- | --- |
| (Stacking of 2 plies of Sterilization Wrap) | Average* | Standard Deviations, +/− |
| KC100 & KC200 | 31.37 | 1.725815 |
| KC200 & KC200 | 29.77 | 1.879746 |
| KC400 & KC400 | 18.57 | 1.301324 |
| KC600 & KC400 | 16.6 | 0.957642 |
| KC600 & KC400 | 12.89 | 0.35103 |

*Average values are based on at least 10 specimens for each sample.

Sample wrappings for quantification proposes were made using the multi-panel sterilization assembly of the invention as shown in FIGS. 21 and 22 and according to the conventional envelope fold systems as shown in FIGS. 14 and 16. These samples are identified in Table 4 for labeling in related tables and figures of graphs of Permeability, Weight, and Plies with respect to Position (e.g., Top, Bottom and Side Strip) and are subsequently described with respect to FIGS. 14-18 and 21, 22, and 24. All samples of Table 4 wrapped around surgical trays with approximate dimensions of 20 inches long× 10.75 inches wide×3.5 inches (~510 mm×~270 mm×~88 mm).

TABLE 4

Samples for Quantification Measurements

| Sample | Wrapping System per: | Barrier Panel Construction (per Table 3) | Plies in Fold Protection Panel | Reinforcement elements |
| --- | --- | --- | --- | --- |
| Hi Wgt New1 | Invention | KC600 & KC400 | 1 | Yes |
| Lo Wgt New1 | Invention | KC100 & KC200 | 1 | Yes |
| Hi Wgt New2 | Invention | KC600 & KC400 | 2 | Yes |
| Lo Wgt New2 | Invention | KC100 & KC200 | 2 | Yes |
| Hi Wgt ONE-STEP | envelope fold | KC600 & KC400 | 0 | No |
| Lo Wgt ONE-STEP | envelope fold | KC100 & KC200 | 0 | No |

TABLE 4-continued

Samples for Quantification Measurements

| Sample | Wrapping System per: | Barrier Panel Construction (per Table 3) | Plies in Fold Protection Panel | Reinforcement elements |
|---|---|---|---|---|
| Hi Wgt Seq | envelope fold | KC600 & KC400 | 0 | No |
| Lo Wgt Seq | envelope fold | KC100 & KC200 | 0 | No |

"Hi Wgt" signifies superposed layers of KC600 and KC400. "Lo Wgt" signifies superposed layers of KC100 and KC 200.

Figure 24:
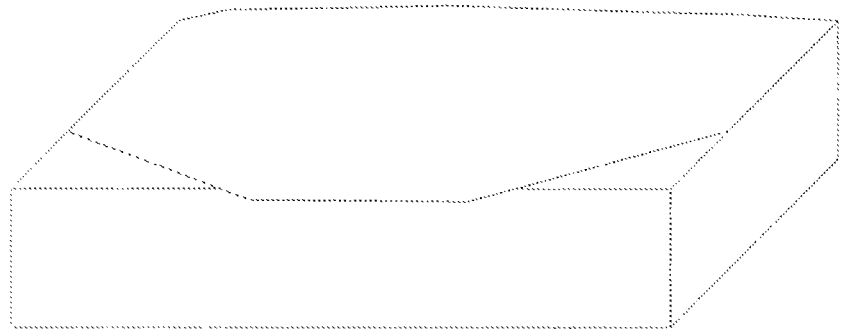
FIG. 24 is an illustration the article of FIG. 21 or FIG. 22 that identifies regions of a package formed by wrapping an article using an exemplary multi-panel sterilization assembly.

Hi Wgt New1 and Lo Wgt New1 samples are representations of the two (2) layer barrier panel and single layer fold protection panel construction illustrated in FIG. 21. Indicated in FIG. 21 are 2 reinforcing elements positioned according to FIG. 10B and a pull tab. The wrapping of these samples around respective surgical trays followed the sequence shown in FIG. 9A-9E and a completed wrapping is illustrated in FIG. 24.

Hi Wgt New2 and Lo Wgt New2 samples are representations of the two (2) layer barrier panel and two (2) ply or layer fold protection panel construction illustrated in FIG. 22. Indicated in FIG. 22 are two (2) separate reinforcing elements positioned according to FIG. 10B and a pull tab. Wrapping of these samples was the same as for the Hi and Lo Wgt New1 samples and a completed wrapping is illustrated in FIG. 24.

Figure 15:
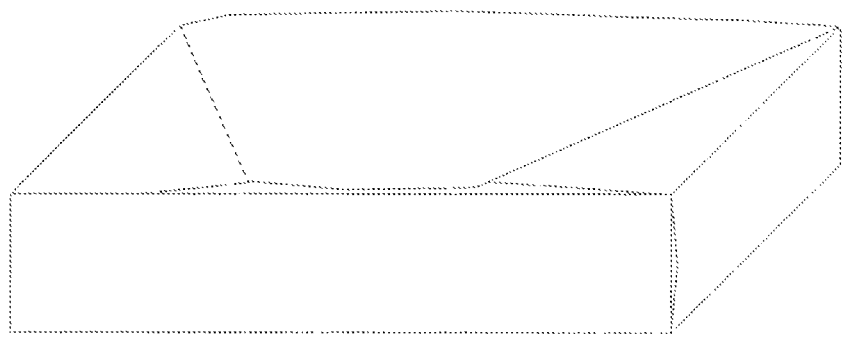
FIG. 15 is an illustration of an article wrapped with conventional sterilization wrap using a conventional envelope fold.

Hi Wgt ONE-STEP and Lo Wgt ONE-STEP samples are representations of the two (2) layer construction illustrated in FIG. 14 where the edges of the superposed sheets of conventional sterilization wrap align; another suitable construction for these ONE-STEP samples is shown in FIG. 1 where the superposed aligned sheets of sterilization wrap are joined together. No reinforcing elements or pull tab are present. The wrapping of these samples around respective surgical trays followed the sequence shown in FIGS. 4A-4E and a completed wrapping is illustrated in FIG. 15. The letters "OS" may be used as an abbreviation for ONE-STEP with respect to these samples.

Figure 17:
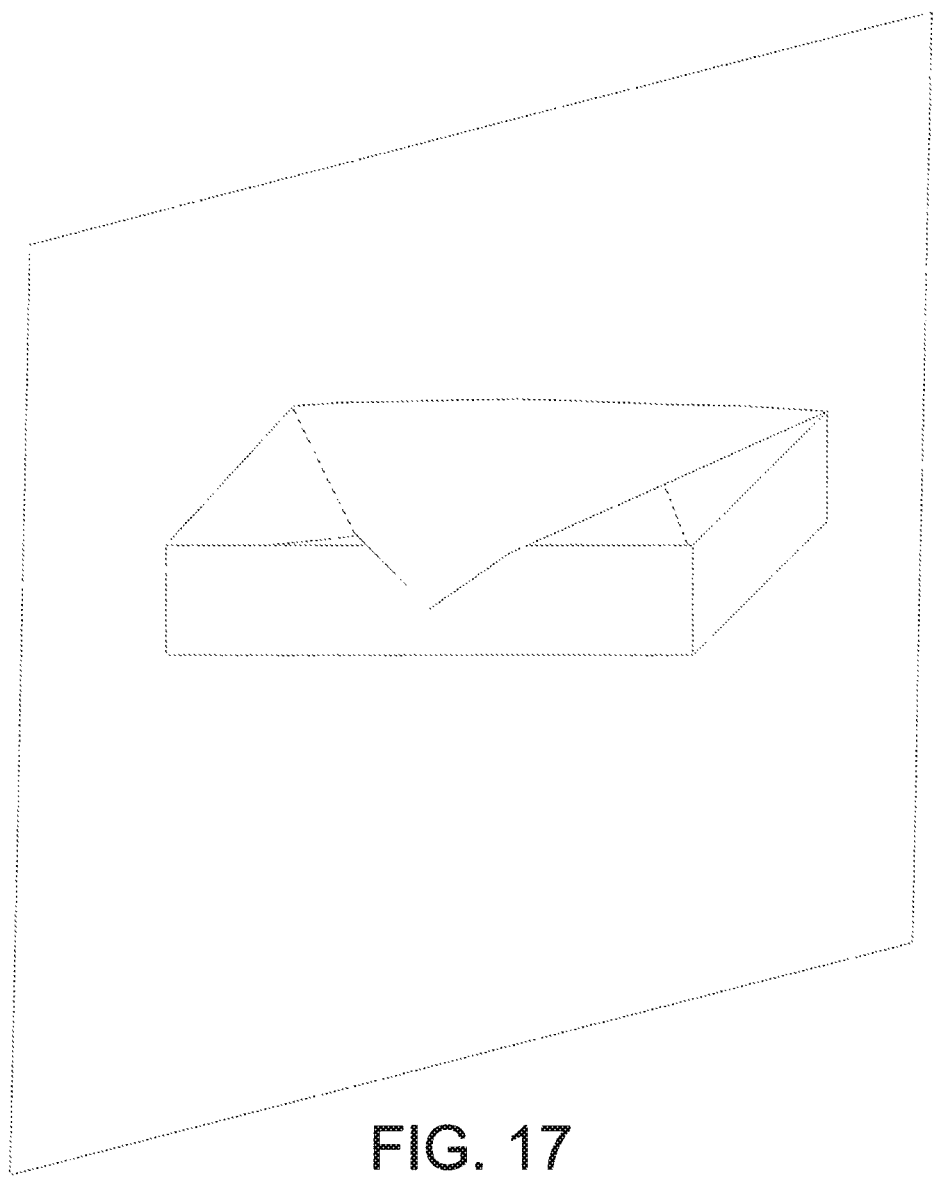
FIG. 17 is an illustration of the article of FIG. 16 wrapped with one sheet of conventional sterilization wrap and positioned on the remaining sheet of conventional sterilization wrap in preparation for subsequent wrapping.
Figure 18:
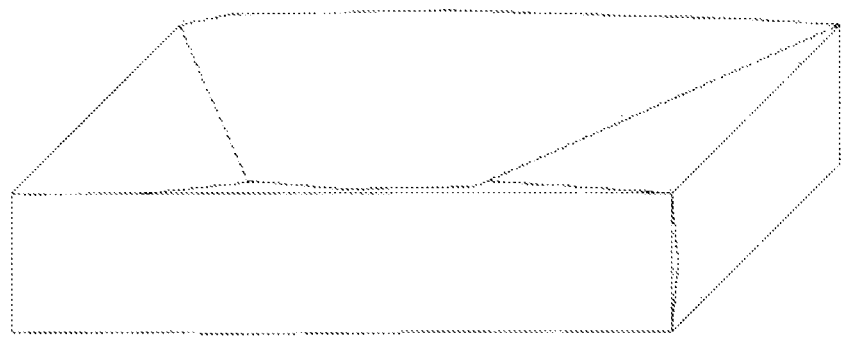
FIG. 18 is an illustration of the completion of the second wrapping of the article of FIG. 16 with the remaining sheet of conventional sterilization wrap of FIG. 17.

Hi Wgt Seq and Lo Wgt Seq samples are representations of the two (2) layer construction illustrated in FIG. 16 where the separate sheets of conventional sterilization wrap are not aligned but are offset with respect to each other by approximately 45 degrees. No reinforcing elements or pull tab are present. To wrap a surgical tray, each sheet of sterilization wrap sequentially folds around the tray according to the sequence shown in FIGS. 4A-4E. FIG. 17 illustrates the wrapping of the first sheet of sterilization wrap with the second sheet of sterilization wrap yet to be wrapped around the surgical tray. FIG. 18 illustrates the completed wrapping of both barrier panels.

The completed wrappings for all samples, inclusive of the Hi Wgt and Lo Wgt New1 and New2 samples, form the specific fold over regions of materials indicated by the labeling in FIG. 19 as Top 402, Bottom 404, Side Strip 406.

FIG. 14 illustrates a standard sterilization tray "T" (approximate length=20 inches (~510 mm), width=10.5 inches (~270 mm) and height=3.5 inches (~88 mm)) and a sheet of bonded two-ply sterilization wrap (e.g., KimGuard® One-Step® sterilization wrap) prior to wrapping. FIG. 15 illustrates the sterilization tray after it has been wrapped in accordance with the procedure illustrated in FIGS. 4A to 4E.

FIG. 16 illustrates a standard sterilization tray "T" (approximate length=20 inches (~510 mm), width=10.5 inches (~270 mm) and height=3.5 inches (~88 mm)) and two sheets of single ply sterilization wrap prior to wrapping. FIG. 17 illustrates the sterilization tray after it has been wrapped in the first sheet of single ply sterilization wrap accordance with the procedure illustrated in FIGS. 4A to 4E. FIG. 18 illustrates the sterilization tray after it has been sequentially wrapped in the second sheet of single ply sterilization wrap accordance with the procedure illustrated in FIGS. 4A to 4E.

FIG. 19 generally illustrates a standard sterilization tray "T" (approximate length=20 inches (~510 mm), width=10.5 inches (~270 mm) and height=3.5 inches (~88 mm)) that has been wrapped sequentially utilizing single ply sterilization wrap or wrapped utilizing a bonded two-ply sterilization wrap (e.g., KimGuard® One-Step® sterilization wrap), both in accordance with the procedure illustrated in FIGS. 4A to 4E, to form a package 400 having a top 402, a bottom 404 and sides 406.

Figure 20:
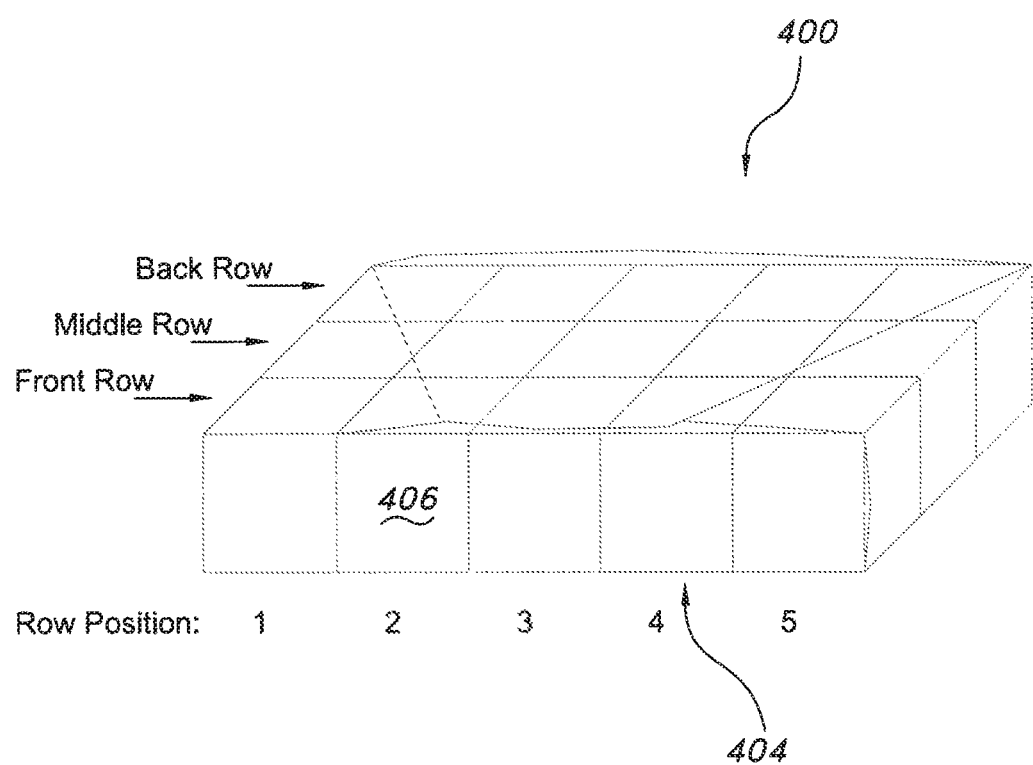
FIG. 20 is an illustration showing the regions of FIG. 19 sectioned or divided into respective arrays.

FIG. 20 illustrates how the wrapped tray is divided into sections. The tray is divided into five length rows (each length row being approximately 3.5 to 4 inches long) along its 20 inch length. The tray is also divided into three width rows (each width row being approximately 3.5 inches wide) and one height row that is approximately 3.5 inches high. There is a 3×5 array for the top 402 of the wrapped tray and a separate 3×5 array for the bottom 404 of the wrapped tray. The front and back of the wrapped tray are divided into separate 1×5 arrays, and each side is divided into separate 1×3 arrays.

The length rows are assigned a position number from 1 to 5 starting with position 1 at the left side of the tray and running to position 5 at the right side of the tray. The width rows are assigned a position location (i.e., Front, Middle, and Back).

Figure 23:
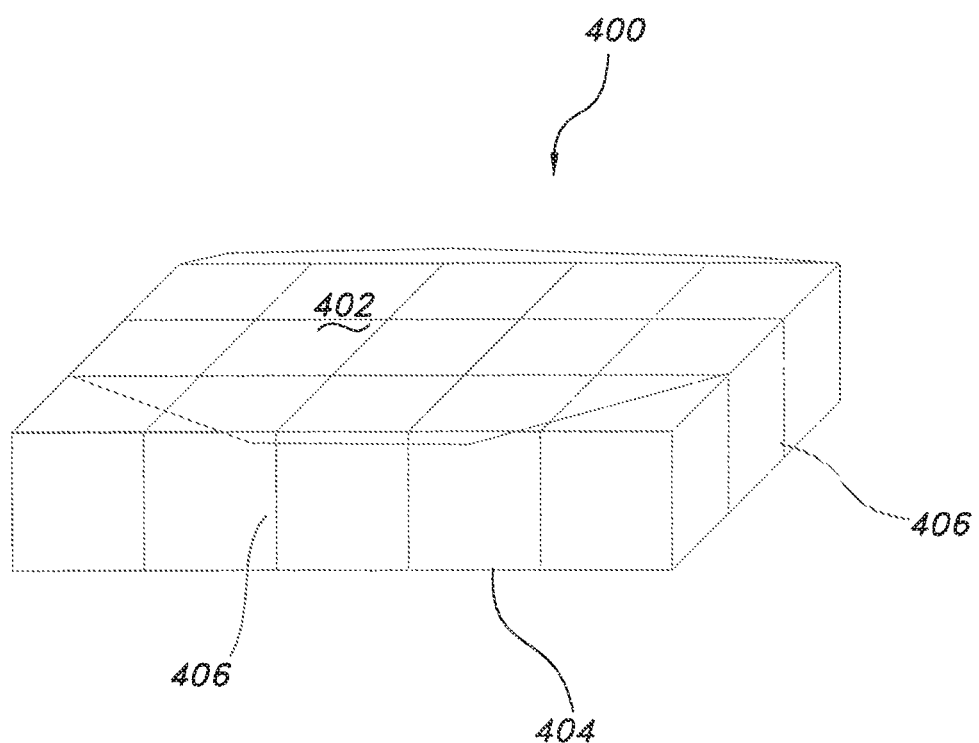
FIG. 23 is an illustration showing the regions of FIG. 24 into sectioned or divided into respective arrays.

FIG. 21 illustrates a standard sterilization tray "T" (approximate length=20 inches (~510 mm), width=10.5 inches (~270 mm) and height=3.5 inches (~88 mm)) and a multi-panel sterilization assembly of the present invention generally in accordance with FIG. 8A prior to wrapping. It should be noted that the barrier panel 102 has two plies of material and the fold protection panel 108 has a single ply of material. FIG. 22 illustrates a standard sterilization tray "T" (approximate length=20 inches (~510 mm), width=10.5 inches (~270 mm) and height=3.5 inches (~88 mm)) and another configuration of the multi-panel sterilization assembly of the present invention generally in accordance with FIG. 8A prior to wrapping. It should be noted that the barrier panel 102 has two plies of material and the fold protection panel 108 also includes two plies of material. FIG. 24 illustrates the sterilization tray after it has been wrapped in accordance with the procedure illustrated in FIGS. 9A to 9E. FIG. 23 illustrates the wrapped sterilization tray divided into sections. As illustrated previously in FIG. 20, there is a 3×5 array for the top 402 of the wrapped tray and a separate 3×5 array for the bottom 404 of the wrapped tray. The front and back of the wrapped tray are divided into separate 1×5 arrays, and each side is divided into separate 1×3 arrays.

The Top 402, the Bottom 404, and the Side 406 regions are shown separated in FIG. 25. Such separation can be achieved by severing the regions apart using scissors or a sharp knife, but an exemplary method cuts the regions apart with a cautery, such as the electrically powered Thermal Cautery Unit, Model 150, made by Geiger Medical Technologies (Monarch Beach, Calif.). Use of such an electrically powered cautery fuses the edges of the severed material together so that each region 402, 404, and 406 forms a unitary construction that simplifies cutting out specimens for subsequent measurements without the need to bind the severed edges with tape or other adhesive. From each separated region, specimens were cut that correspond to respective positions in the arrays using a 3-inch circular die.

The following Tables 5 to 19 give measurements made for specimens that are 3-inch (7.62 cm) in diameter and are taken from the Top, Bottom and Side Strip regions after sectioning. These measurements are presented as:

averaged values of individual measurements for Permeability, weight and ply count for two or three samples in each row position, except as indicated by "*". For example for the Hi Wgt ONE-STEP sample in Table 9, the Front 1 value of 4.7 (CFM) is the average of 3 specimens from 3 respective separate Top samples. Typical standard deviations for these averaged values were less than 15% of the averaged value. Sample labels in Tables 5, 6, 8, 9, 12, and 13 that are followed by an "*" symbol designate individual measurements from a single sample rather than an average of measurements from two or three samples.

Figure 26:
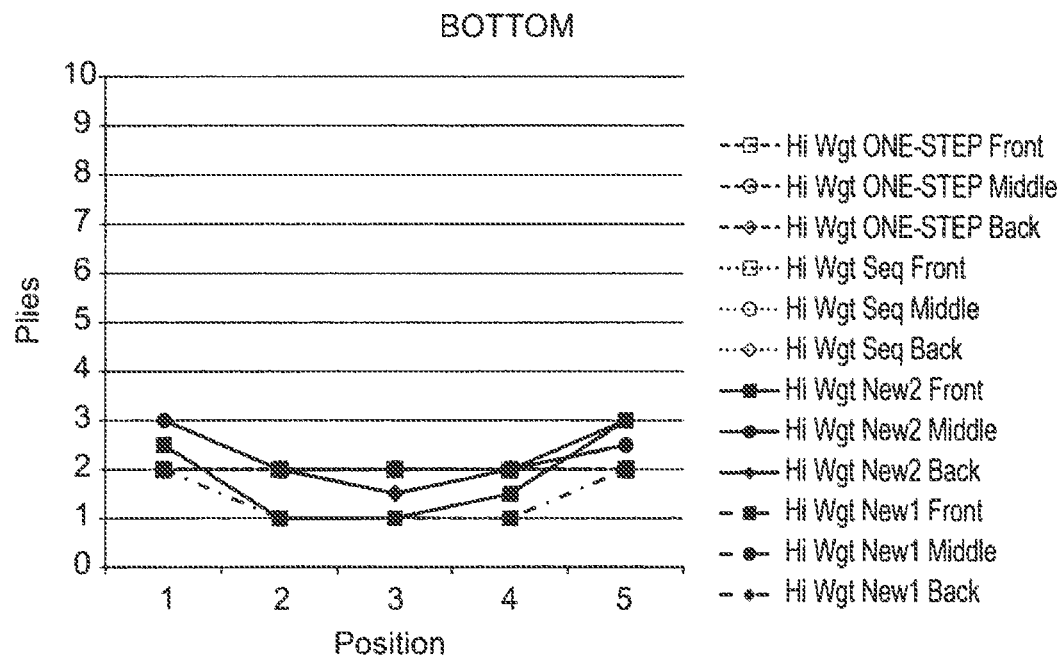
FIG. 26 is an illustration of a graph of data and information from Table 5.

"Avg" sample values, e.g. Avg Hi Wgt ONE-STEP, Avg Hi Wgt New1, and are the averages among the respective Front, Middle and Back row averaged values; for example in Table 9 the Avg Hi Wgt ONE-STEP Position 1 value of 5.1 (CFM) is the average of the Front's 4.7, the Middle's 5.4 and the Back's 5.2 averaged values. For the Top and Bottom regions such reporting does not alter the relative directional change with respect to adjacent positions established by the average values reported in each row. This retention of direction changes is shown by comparing FIG. 26 to FIG. 27 and FIG. 28 to FIG. 29. FIG. 26 graphs the averaged values for each row (Front, Middle, back) for each sample for the Bottom region of a sectioned wrapping and FIG. 27 graphs the same data but expressed as the "Avg" sample values; FIG. 28 similarly graphs the averaged values for each row (Front, Middle, back) for each sample for the Top region of a sectioned wrapping and FIG. 29 graphs the same data expressed as the "Avg" sample values. Reporting the data as "Avg' sample values visually clarifies the distinctions of the invention from the other wrapping systems.

TABLE 5

Maximum Plies in Bottom region of wrappings

| Position: | | 1 | 2 | 3 | 4 | 5 |
|---|---|---|---|---|---|---|
| Avg Hi Wgt ONE-STEP | | 2 | 2 | 2 | 2 | 2 |
| Avg Hi Wgt Seq | | 2 | 2 | 2 | 2 | 2 |
| Hi Wgt New2 | Front | 2.5 | 1 | 1 | 1.5 | 3 |
| Hi Wgt New2 | Middle | 3 | 2 | 2 | 2 | 2.5 |
| Hi Wgt New2 | Back | 3 | 2 | 1.5 | 2 | 3 |
| Avg Hi Wgt New2 | | 2.8 | 1.7 | 1.5 | 1.8 | 2.8 |
| Hi Wgt New1* | Front | 2 | 1 | 1 | 1 | 2 |
| Hi Wgt New1* | Middle | 2 | 1 | 1 | 1 | 2 |
| Hi Wgt New1* | Back | 2 | 1 | 1 | 1 | 2 |
| Avg Hi Wgt New1 | | 2 | 1 | 1 | 1 | 2 |

TABLE 6

Maximum Plies in Top region of wrappings

| Position: | | 1 | 2 | 3 | 4 | 5 |
|---|---|---|---|---|---|---|
| Hi Wgt ONE-STEP | Front | 12.3 | 12.3 | 20.7 | 15.3 | 14.7 |
| Hi Wgt ONE-STEP | Middle | 12 | 15.7 | 26.3 | 20.7 | 13.3 |
| Hi Wgt ONE-STEP | Back | 11 | 12.7 | 15.7 | 13.3 | 11.3 |
| Avg Hi Wgt ONE-STEP | | 11.8 | 13.6 | 20.9 | 16.4 | 13.1 |
| Hi Wgt Seq | Front | 14.7 | 13.7 | 23.7 | 15.7 | 16 |

TABLE 6-continued

Maximum Plies in Top region of wrappings

| Position: | | 1 | 2 | 3 | 4 | 5 |
|---|---|---|---|---|---|---|
| Hi Wgt Seq | Middle | 12.7 | 16 | 23 | 19.7 | 14 |
| Hi Wgt Seq | Back | 12 | 12.7 | 17.3 | 14 | 12 |
| Avg Hi Wgt Seq | | 13.1 | 14.1 | 21.3 | 16.4 | 14 |
| Hi Wgt New2 | Front | 11 | 8 | 5 | 4.5 | 15 |
| Hi Wgt New2 | Middle | 11 | 9 | 5 | 6 | 12 |
| Hi Wgt New2 | Back | 9 | 10 | 5.5 | 6 | 8.5 |
| Avg Hi Wgt New2 | | 10.3 | 9 | 5.2 | 5.5 | 11.8 |
| Hi Wgt New1* | Front | 9 | 3 | 4 | 4 | 9 |
| Hi Wgt New1* | Middle | 7 | 6 | 4 | 4 | 9 |
| Hi Wgt New1* | Back | 7 | 7 | 4 | 6 | 11 |
| Avg Hi Wgt New1 | | 7.7 | 5.3 | 4 | 4.7 | 9.7 |

TABLE 7

Maximum Plies in Top and Bottom regions of wrappings

| Position: | | 1 | 2 | 3 | 4 | 5 |
|---|---|---|---|---|---|---|
| Lo Wgt ONE-STEP | Front | 15.3 | 21 | 22.7 | 19.7 | 15.7 |
| Lo Wgt ONE-STEP | Middle | 14.7 | 19 | 25.3 | 17.3 | 16.3 |
| Lo Wgt ONE-STEP | Back | 14.7 | 14.3 | 21.7 | 15 | 12.7 |
| Avg Lo Wgt ONE-STEP | | 14.9 | 18.1 | 23.2 | 17.3 | 14.9 |
| Lo Wgt Seq | Front | 18.3 | 19.7 | 27 | 24 | 16.7 |
| Lo Wgt Seq | Middle | 21 | 28.3 | 33.7 | 21 | 11.7 |
| Lo Wgt Seq | Back | 18.3 | 18 | 23.3 | 13 | 14.7 |
| Avg Lo Wgt Seq | | 19.2 | 22 | 28 | 19.3 | 14.3 |
| Lo Wgt New2 | Front | 18 | 13 | 7 | 6 | 16.5 |
| Lo Wgt New2 | Middle | 13.5 | 13 | 6 | 7 | 15 |
| Lo Wgt New2 | Back | 12 | 8.5 | 7 | 9.5 | 13.5 |
| Avg Lo Wgt New2 | | 14.5 | 11.5 | 6.7 | 7.5 | 15 |
| Lo Wgt New1 | Front | 10 | 4 | 4 | 4 | 9 |
| Lo Wgt New1 | Middle | 9 | 7.5 | 5 | 8 | 9.5 |
| Lo Wgt New1 | Back | 10 | 9 | 6 | 7 | 11.5 |
| Avg Lo Wgt New1 | | 9.7 | 6.8 | 5 | 6.3 | 10 |
| BOTTOM | | | | | | |
| Lo Wgt New1 | Front | 3 | 2 | 2 | 2 | 3 |
| Lo Wgt New1 | Middle | 3 | 2 | 2 | 2 | 3 |
| Lo Wgt New1 | Back | 3 | 2 | 2 | 2 | 3 |
| Avg Lo Wgt New1 | | 3 | 2 | 2 | 2 | 3 |
| Lo Wgt New2 | Front | 3 | 2 | 2 | 2 | 2.5 |
| Lo Wgt New2 | Middle | 3 | 2 | 2 | 2 | 3 |
| Lo Wgt New2 | Back | 3 | 2 | 2 | 2 | 3 |
| Avg Lo Wgt New2 | | 3 | 2 | 2 | 2 | 2.8 |
| Avg Lo Wgt OS & Seq | | 2 | 2 | 2 | 2 | 2 |

TABLE 8

Permeability, CFM in BOTTOM region

| Position | | 1 | 2 | 3 | 4 | 5 |
|---|---|---|---|---|---|---|
| Hi Wgt ONE-STEP | Front | 15.8 | 15.8 | 15.7 | 16.1 | 15.4 |
| Hi Wgt ONE-STEP | Middle | 16.4 | 15.8 | 15.7 | 15.6 | 16.1 |
| Hi Wgt ONE-STEP | Back | 15.8 | 16.2 | 15.6 | 15.9 | 16.1 |
| Avg Hi Wgt ONE-STEP | | 16 | 15.9 | 15.7 | 15.9 | 15.9 |
| Hi Wgt Seq | Front | 17.4 | 16.8 | 17.7 | 17.3 | 17.7 |
| Hi Wgt Seq | Middle | 17 | 17.3 | 17.5 | 17.9 | 17.1 |
| Hi Wgt Seq | Back | 16.9 | 17.7 | 17.7 | 17.6 | 16.3 |
| Avg Hi Wgt Seq | | 17.1 | 17.3 | 17.7 | 17.6 | 17.0 |
| Hi Wgt New2 | Front | 13.9 | 14.8 | 15.0 | 15.65 | 15.3 |
| Hi Wgt New2 | Middle | 13.8 | 15.3 | 14.8 | 15.7 | 16 |
| Hi Wgt New2 | Back | 13.7 | 14.9 | 14.7 | 15.6 | 14.7 |
| Avg Hi Wgt New2 | | 13.8 | 15.0 | 14.8 | 15.7 | 15.3 |
| Hi Wgt New1* | Front | 15.4 | 14.7 | 15.1 | 16 | 14 |
| Hi Wgt New1* | Middle | 14.2 | 15.5 | 14.9 | 15.4 | 14.5 |
| Hi Wgt New1* | Back | 15.1 | 14.7 | 14.8 | 16.2 | 14 |
| Avg Hi Wgt New1 | | 14.9 | 15.0 | 14.9 | 15.9 | 14.2 |

TABLE 9

Permeability, CFM in TOP region

| Sample | Position: | 1 | 2 | 3 | 4 | 5 |
|---|---|---|---|---|---|---|
| Hi Wgt ONE-STEP | Front | 4.7 | 4.9 | 6.2 | 4.9 | 4.2 |
| Hi Wgt ONE-STEP | Middle | 5.4 | 5.3 | 5.0 | 5.1 | 5.8 |
| Hi Wgt ONE-STEP | Back | 5.2 | 5.3 | 5.3 | 5.2 | 9.3 |
| Avg Hi Wgt ONE-STEP | | 5.1 | 5.2 | 5.5 | 5.1 | 6.4 |
| Hi Wgt Seq | Front | 4.7 | 5.3 | 5.3 | 4.6 | 4.4 |
| Hi Wgt Seq | Middle | 5.0 | 4.7 | 4.7 | 5.0 | 5.5 |
| Hi Wgt Seq | Back | 5.8 | 5.5 | 5.3 | 5.2 | 5.4 |
| Avg Hi Wgt Seq | | 5.2 | 5.2 | 5.1 | 4.9 | 5.1 |
| Hi Wgt New2 | Front | 6.8 | 8.6 | 9.9 | 17.5 | 9.2 |
| Hi Wgt New2 | Middle | 4.8 | 8.8 | 7.3 | 8.0 | 5.2 |
| Hi Wgt New2 | Back | 5 | 6.73 | 7.4 | 6.8 | 5.3 |
| Avg Hi Wgt New2 | | 5.6 | 8.0 | 8.2 | 10.8 | 6.6 |
| Hi Wgt New1* | Front | 6.9 | 10.5 | 7.4 | 12.2 | 7.6 |
| Hi Wgt New1* | Middle | 5.3 | 8.97 | 9.0 | 9.2 | 6.3 |
| Hi Wgt New1* | Back | 5.8 | 8.6 | 9.0 | 10.4 | 6.9 |
| Avg Hi Wgt New1 | | 6.0 | 9.4 | 8.5 | 10.6 | 6.9 |

TABLE 10

Permeability, CFM in BOTTOM region

| | Position | 1 | 2 | 3 | 4 | 5 |
|---|---|---|---|---|---|---|
| Lo Wgt ONE-STEP | Front | 32.1 | 32.6 | 32.5 | 32.5 | 31.6 |
| Lo Wgt ONE-STEP | Middle | 32.6 | 32.5 | 32.4 | 32.0 | 31.6 |
| Lo Wgt ONE-STEP | Back | 31.5 | 31.5 | 32.3 | 32.4 | 33.0 |
| Avg Lo Wgt ONE-STEP | | 32.1 | 32.2 | 32.4 | 32.3 | 32.1 |
| Lo Wgt Seq | Front | 31.4 | 30.6 | 30.4 | 30.3 | 29.0 |
| Lo Wgt Seq | Middle | 31.3 | 30.6 | 30.4 | 30.1 | 30.8 |
| Lo Wgt Seq | Back | 31.2 | 30.7 | 30.7 | 30.3 | 30.0 |
| Avg Lo Wgt Seq | | 31.3 | 30.6 | 30.5 | 30.2 | 29.9 |
| Lo Wgt New2 | Front | 26.6 | 27.2 | 26.3 | 25.7 | 24.2 |
| Lo Wgt New2 | Middle | 26.1 | 26.9 | 26.5 | 25.4 | 24.5 |
| Lo Wgt New2 | Back | 27.1 | 27.6 | 27.2 | 25.75 | 25 |
| Avg Lo Wgt New2 | | 26.6 | 27.2 | 26.6 | 25.6 | 24.6 |
| Lo Wgt New1 | Front | 25.6 | 26.1 | 27.4 | 26.1 | 24.5 |
| Lo Wgt New1 | Middle | 25.3 | 26.05 | 27.2 | 25.7 | 24.8 |
| Lo Wgt New1 | Back | 25.1 | 26.2 | 27.8 | 26.3 | 23.5 |
| Avg Lo Wgt New1 | | 25.3 | 26.1 | 27.4 | 26.0 | 24.2 |

TABLE 11

Permeability, CFM in TOP region

| | Position: | 1 | 2 | 3 | 4 | 5 |
|---|---|---|---|---|---|---|
| Lo Wgt ONE-STEP | Front | 6.8 | 7.1 | 6.2 | 5.7 | 6.8 |
| Lo Wgt ONE-STEP | Middle | 7.25 | 5.8 | 6.2 | 6.2 | 7.6 |
| Lo Wgt ONE-STEP | Back | 8.2 | 6.9 | 10.9 | 7.4 | 7.5 |
| Avg Lo Wgt ONE-STEP | | 7.4 | 6.6 | 7.8 | 6.4 | 7.3 |
| Lo Wgt Seq | Front | 7.0 | 6.0 | 6.1 | 5.3 | 7.1 |
| Lo Wgt Seq | Middle | 7.3 | 4.5 | 4.3 | 5.3 | 7.2 |
| Lo Wgt Seq | Back | 8.5 | 6.6 | 6.4 | 8.2 | 7.9 |
| Avg Lo Wgt Seq | | 7.6 | 5.7 | 5.6 | 6.3 | 7.4 |
| Lo Wgt New2 | Front | 6.4 | 10.4 | 10.5 | 13.1 | 7.2 |
| Lo Wgt New2 | Middle | 6.2 | 7.9 | 12.1 | 10.5 | 6.7 |
| Lo Wgt New2 | Back | 7.38 | 7.6 | 13.4 | 8.5 | 7.7 |
| Avg Lo Wgt New2 | | 6.6 | 8.6 | 12.0 | 10.7 | 7.2 |
| Lo Wgt New1 | Front | 12.8 | 17.3 | 14.8 | 18.2 | 16.5 |
| Lo Wgt New1 | Middle | 7.5 | 13.4 | 14.5 | 7.9 | 6.4 |
| Lo Wgt New1 | Back | 9.4 | 12.9 | 13.3 | 6.7 | 9.6 |
| Avg Lo Wgt New1 | | 9.9 | 14.5 | 14.2 | 10.9 | 10.8 |

TABLE 12

Wgt, gms in BOTTOM region

| | Position: | 1 | 2 | 3 | 4 | 5 |
|---|---|---|---|---|---|---|
| Hi Wgt ONE-STEP | Front | 0.68 | 0.71 | 0.70 | 0.70 | 0.69 |
| Hi Wgt ONE-STEP | Middle | 0.67 | 0.68 | 0.71 | 0.69 | 0.68 |
| Hi Wgt ONE-STEP | Back | 0.68 | 0.67 | 0.69 | 0.70 | 0.68 |
| Avg Hi Wgt ONE-STEP | | 0.67 | 0.69 | 0.70 | 0.70 | 0.68 |
| Hi Wgt Seq | Front | 0.66 | 0.68 | 0.67 | 0.69 | 0.68 |
| Hi Wgt Seq | Middle | 0.68 | 0.67 | 0.68 | 0.67 | 0.70 |
| Hi Wgt Seq | Back | 0.69 | 0.66 | 0.68 | 0.67 | 0.71 |
| Avg Hi Wgt Seq | | 0.67 | 0.67 | 0.68 | 0.67 | 0.69 |
| Hi Wgt New2 | Front | 0.92 | 0.67 | 0.73 | 0.72 | 0.73 |
| Hi Wgt New2 | Middle | 0.94 | 0.66 | 0.73 | 0.71 | 0.69 |
| Hi Wgt New2 | Back | 0.94 | 0.65 | 0.74 | 0.72 | 0.73 |
| Avg Hi Wgt New2 | | 0.93 | 0.66 | 0.73 | 0.72 | 0.72 |
| Hi Wgt New1* | Front | 0.96 | 0.69 | 0.70 | 0.71 | 0.83 |
| Hi Wgt New1* | Middle | 0.92 | 0.70 | 0.72 | 0.73 | 0.81 |
| Hi Wgt New1* | Back | 0.89 | 0.72 | 0.70 | 0.69 | 0.73 |
| Avg Hi Wgt New1 | | 0.92 | 0.70 | 0.71 | 0.71 | 0.79 |

TABLE 13

Wgt, gms in TOP region

| | Position: | 1 | 2 | 3 | 4 | 5 |
|---|---|---|---|---|---|---|
| Hi Wgt ONE-STEP | Front | 4.17 | 3.58 | 3.99 | 3.88 | 4.53 |
| Hi Wgt ONE-STEP | Middle | 3.56 | 3.68 | 5.96 | 4.10 | 3.57 |
| Hi Wgt ONE-STEP | Back | 3.24 | 3.38 | 3.92 | 3.67 | 3.20 |
| Avg Hi Wgt ONE-STEP | | 3.66 | 3.55 | 4.62 | 3.88 | 3.77 |
| Hi Wgt Seq | Front | 3.98 | 3.74 | 4.87 | 4.18 | 4.61 |
| Hi Wgt Seq | Middle | 3.50 | 3.85 | 5.54 | 4.58 | 3.59 |
| Hi Wgt Seq | Back | 3.18 | 3.25 | 3.72 | 3.41 | 3.23 |
| Avg Hi Wgt Seq | | 3.56 | 3.61 | 4.71 | 4.06 | 3.81 |
| Hi Wgt New2 | Front | 3.24 | 1.57 | 1.77 | 1.53 | 2.54 |
| Hi Wgt New2 | Middle | 3.59 | 2.28 | 1.60 | 1.54 | 3.34 |
| Hi Wgt New2 | Back | 2.98 | 2.65 | 1.71 | 1.65 | 2.98 |
| Avg Hi Wgt New2 | | 3.27 | 2.17 | 1.70 | 1.57 | 2.95 |
| Hi Wgt New1* | Front | 2.64 | 1.25 | 1.66 | 1.19 | 2.12 |
| Hi Wgt New1* | Middle | 2.94 | 1.8 | 1.45 | 1.38 | 2.66 |
| Hi Wgt New1* | Back | 2.43 | 2.33 | 1.45 | 1.57 | 2.84 |
| Avg Hi Wgt New1 | | 2.67 | 1.80 | 1.52 | 1.38 | 2.54 |

TABLE 14

Wgt, gms in Top region

| | Position: | 1 | 2 | 3 | 4 | 5 |
|---|---|---|---|---|---|---|
| Lo Wgt ONE-STEP | Front | 2.06 | 2.00 | 2.37 | 2.39 | 2.26 |
| Lo Wgt ONE-STEP | Middle | 1.85 | 2.48 | 2.99 | 2.58 | 1.87 |
| Lo Wgt ONE-STEP | Back | 1.76 | 1.94 | 1.92 | 2.21 | 1.86 |
| Avg Lo Wgt ONE-STEP | | 1.89 | 2.14 | 2.43 | 2.39 | 2.00 |
| Lo Wgt Seq | Front | 2.03 | 2.57 | 2.31 | 2.66 | 1.96 |
| Lo Wgt Seq | Middle | 1.87 | 3.18 | 3.37 | 2.47 | 1.73 |
| Lo Wgt Seq | Back | 1.65 | 1.99 | 2.22 | 1.88 | 1.69 |
| Avg Lo Wgt Seq | | 1.85 | 2.59 | 2.63 | 2.34 | 1.79 |
| Lo Wgt New2 | Front | 2.02 | 1.12 | 1.01 | 0.88 | 1.67 |
| Lo Wgt New2 | Middle | 1.92 | 1.60 | 0.90 | 1.11 | 1.86 |
| Lo Wgt New2 | Back | 1.67 | 1.66 | 0.85 | 1.23 | 1.71 |
| Avg Lo Wgt New2 | | 1.87 | 1.46 | 0.92 | 1.08 | 1.75 |
| Lo Wgt New1 | Front | 1.08 | 0.61 | 0.63 | 0.54 | 0.99 |
| Lo Wgt New1 | Middle | 1.57 | 0.96 | 0.66 | 1.10 | 1.56 |
| Lo Wgt New1 | Back | 1.31 | 1.06 | 0.72 | 1.34 | 1.34 |
| Avg Lo Wgt New1 | | 1.32 | 0.88 | 0.67 | 0.99 | 1.30 |

TABLE 15

Wgt, gms in BOTTOM region

| | Position: | 1 | 2 | 3 | 4 | 5 |
|---|---|---|---|---|---|---|
| Lo Wgt ONE-STEP | Front | 0.36 | 0.35 | 0.35 | 0.36 | 0.36 |
| Lo Wgt ONE-STEP | Middle | 0.35 | 0.35 | 0.35 | 0.35 | 0.36 |
| Lo Wgt ONE-STEP | Back | 0.35 | 0.35 | 0.36 | 0.36 | 0.36 |
| Avg Lo Wgt ONE-STEP | | 0.35 | 0.35 | 0.35 | 0.35 | 0.36 |
| Lo Wgt Seq | Front | 0.36 | 0.35 | 0.35 | 0.35 | 0.35 |
| Lo Wgt Seq | Middle | 0.36 | 0.35 | 0.35 | 0.35 | 0.35 |
| Lo Wgt Seq | Back | 0.35 | 0.35 | 0.35 | 0.35 | 0.35 |
| Avg Lo Wgt Seq | | 0.35 | 0.35 | 0.35 | 0.35 | 0.35 |
| Lo Wgt New2 | Front | 0.46 | 0.35 | 0.35 | 0.35 | 0.41 |
| Lo Wgt New2 | Middle | 0.45 | 0.36 | 0.35 | 0.36 | 0.39 |
| Lo Wgt New2 | Back | 0.42 | 0.35 | 0.35 | 0.35 | 0.41 |
| Avg Lo Wgt New2 | | 0.44 | 0.35 | 0.35 | 0.35 | 0.40 |
| Lo Wgt New1 | Front | 0.41 | 0.35 | 0.35 | 0.35 | 0.47 |
| Lo Wgt New1 | Middle | 0.42 | 0.35 | 0.35 | 0.35 | 0.46 |
| Lo Wgt New1 | Back | 0.42 | 0.35 | 0.35 | 0.35 | 0.47 |
| Avg Lo Wgt New1 | | 0.42 | 0.35 | 0.35 | 0.35 | 0.47 |

TABLE 16

Wgt, gms in SIDE STRIP region

| SIDE STRIP Wgt, gms | Position | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Avg Lo Wgt ONE-STEP | 0.3 | 0.4 | 0.3 | 0.4 | 0.3 | 0.8 | 1.3 | 0.9 | 1.4 | 1.5 | 1.6 | 2.1 | 1.9 | 1.7 | 1.1 | 0.9 |
| Avg Lo Wgt Seq | 0.3 | 0.4 | 0.4 | 0.4 | 0.3 | 1.0 | 1.2 | 1.3 | 1.4 | 1.8 | 2.3 | 1.7 | 1.3 | 1.1 | 1.5 | 1.2 |
| Avg Lo Wgt New2 | 0.4 | 0.4 | 0.4 | 0.4 | 0.5 | 2.2 | 1.6 | 1.5 | 1.5 | 1.4 | 0.9 | 1.1 | 1.6 | 2.4 | 1.9 | 1.6 |
| Avg Lo Wgt New1 | 0.5 | 0.3 | 0.3 | 0.4 | 0.5 | 1.8 | 2.4 | 1.7 | 1.1 | 0.7 | 0.7 | 0.8 | 1.2 | 1.9 | 2.0 | 1.7 |

TABLE 17

Maximum Plies in SIDE STRIP region of wrappings

| | Position | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Avg Lo Wgt ONE-STEP | 2 | 2 | 2 | 2 | 2 | 12.0 | 13.7 | 15.7 | 15.7 | 16.7 | 16.0 | 19.5 | 26.0 | 29.5 | 12.0 | 8.7 |
| Avg Lo Wgt Seq | 2 | 2 | 2 | 2 | 2 | 10.7 | 12.3 | 21.0 | 17.0 | 18.7 | 41.7 | 16.0 | 16.7 | 13.7 | 16.7 | 16.0 |
| Avg Lo Wgt New2 | 3 | 2 | 2 | 2 | 3 | 14.0 | 12.0 | 14.0 | 18.5 | 10.0 | 5.5 | 8.5 | 16.5 | 26.0 | 14.5 | 11.0 |
| Avg Lo Wgt New1 | 3 | 2 | 2.5 | 2 | 3 | 11.5 | 23.0 | 12.0 | 12.5 | 6.0 | 4.5 | 5.5 | 17.5 | 28.0 | 16.5 | 12.5 |

TABLE 18

Wgt, gms in SIDE STRIP region

| | Position | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Avg Hi Wgt ONE-STEP | 0.7 | 0.7 | 0.7 | 0.7 | 0.7 | 2.2 | 2.7 | 2.7 | 3.0 | 3.2 | 3.1 | 3.1 | 2.9 | 3.1 | 2.7 | 2 |
| Avg Hi Wgt Seq | 0.7 | 0.7 | 0.7 | 0.7 | 0.7 | 2.5 | 2.8 | 3.5 | 2.9 | 3.1 | 2.9 | 3.0 | 2.9 | 2.9 | 2.7 | 2.7 |
| Avg Hi Wgt New2 | 0.7 | 0.7 | 0.7 | 0.7 | 0.9 | 4.1 | 3.4 | 3.2 | 2.9 | 2.2 | 1.6 | 1.7 | 2.4 | 3.3 | 3.8 | 3.4 |
| Avg Hi Wgt New1 | 0.7 | 0.7 | 0.7 | 0.7 | 1.0 | 3.9 | 4.6 | 3.3 | 1.6 | 1.3 | 1.1 | 1.2 | 2.0 | 4.3 | 3.9 | 2.8 |

TABLE 19

Maximum Plies in SIDE STRIP region of wrappings

| | Position | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Avg Hi Wgt ONE-STEP | 2.0 | 2.0 | 2.0 | 2.0 | 2.0 | 11.7 | 11.3 | 11.0 | 10.7 | 9.7 | 14.0 | 10.0 | 15.3 | 7.7 | 14.0 | 12.7 |
| Avg Hi Wgt Seq | 2.0 | 2.0 | 2.7 | 2.3 | 2.0 | 11.3 | 12.7 | 24.3 | 12.0 | 12.0 | 13.0 | 13.0 | 14.0 | 15.0 | 13.7 | 14.3 |
| Avg Hi Wgt New2 | 2.5 | 2.0 | 1.5 | 2.0 | 3.0 | 18.0 | 9.0 | 9.0 | 11.5 | 10.0 | 5.0 | 9.0 | 10.0 | 16.0 | 13.5 | 11.5 |
| Avg Hi Wgt New1 | 2.0 | 2.0 | 2.0 | 2.0 | 3.0 | 11.0 | 12.0 | 11.0 | 7.0 | 6.0 | 5.0 | 5.0 | 7.0 | 15.0 | 11.0 | 12.0 |

As can be seem from these Tables, the multi-panel sterilization assembly of the present invention provides less than ten (10) stacked plies of material in the central portion of the Top region 402.

FIG. 26 shows the averaged values of the maximum number of plies (Plies) in 3-inch diameter specimens of all Hi Wgt wrappings taken from the 3×5 array from the Bottom region versus their relative row position. Some of the invention's numbers of plies exceed 2 at the 1 and 5 positions due to the presence of the reinforcement elements. The data is listed in Table 5. The absence of consistently counting two plies for the New1 and New2 samples in positions 2, 3, and 4 is attributed to the tacking together the barrier panels by adhesive that was optionally used in their construction; the consistency among the Wgt values shown in FIG. 35 and listed in Table 12 confirm the presence of two barrier panels for New1 and New2 samples.

Figure 27:
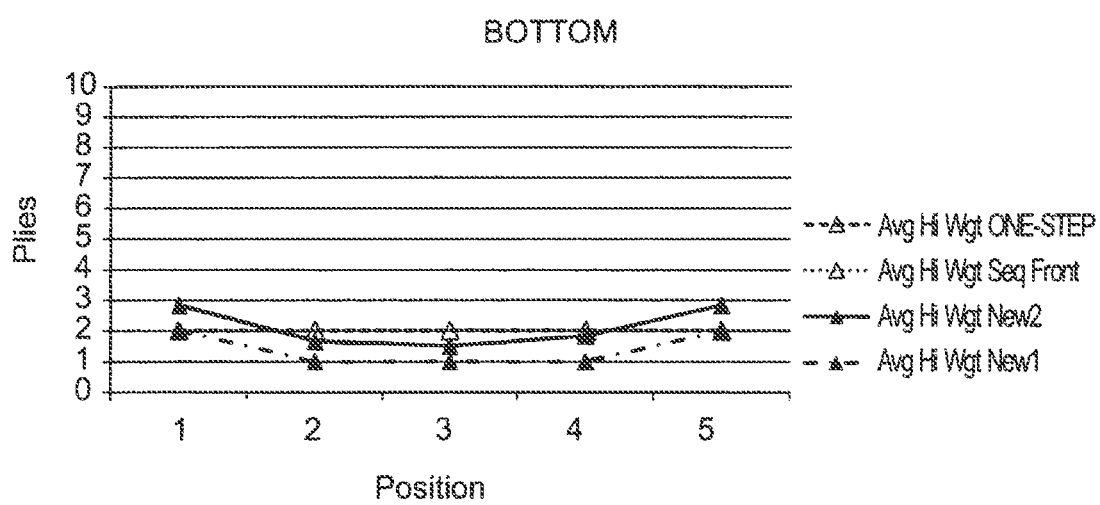
FIG. 27 is an illustration of another graph of data and information from Table 5.
Figure 28:
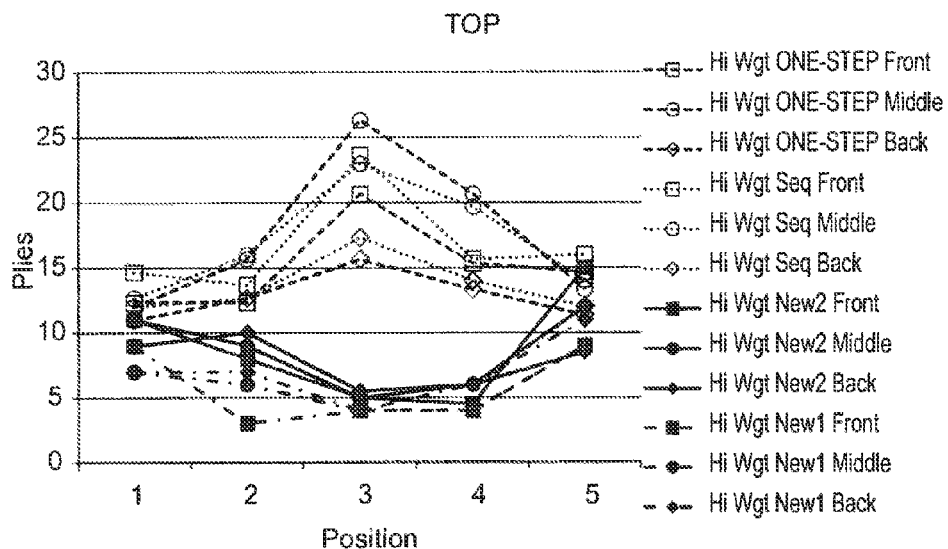
FIG. 28 is an illustration of a graph of data and information from Table 6.

FIG. 27 shows the Plies averages among the respective Front, Middle and Back row averaged values of FIG. 26 for each Hi Wgt sample. This presents the Avg data for the samples that are listed in Table 5.

FIG. 28 shows the averaged values of the Plies in 3-inch diameter specimens taken from the 3×5 array from the Top region of Hi Wgt wrappings versus their relative row position. All but the invention's Plies in the 1 and 5 positions are less than the corresponding averaged values for the envelope folded wrappings. The data is listed in Table 6.

Figure 29:
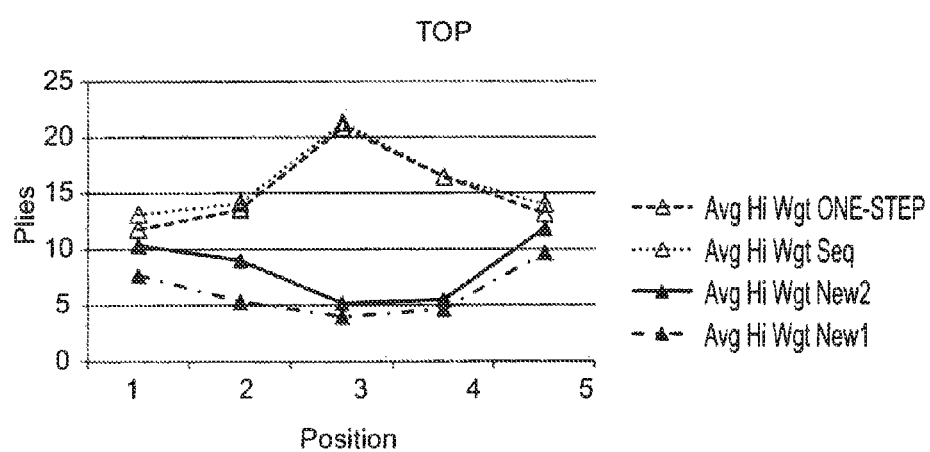
FIG. 29 is an illustration of another graph of data and information from Table 6.

FIG. 29 shows the Plies averages among the respective Front, Middle and Back row averaged values of FIG. 28 for each Hi Wgt sample. This presents the Avg data for the samples that are listed in Table 6. Comparing FIG. 29 to FIG. 28 visually shows that representing the 3×5 array's averaged values for Plies as averages among the rows relative to their position retains the validity of the distinctions of the invention from the conventional envelope fold for Hi Wgt wrappings. This Figure, like FIG. 28, clearly shows that the Plies for the invention in the center of the Top region consistently average less than 10 stacked plies while the Plies for the envelope fold are greater.

Figure 30:
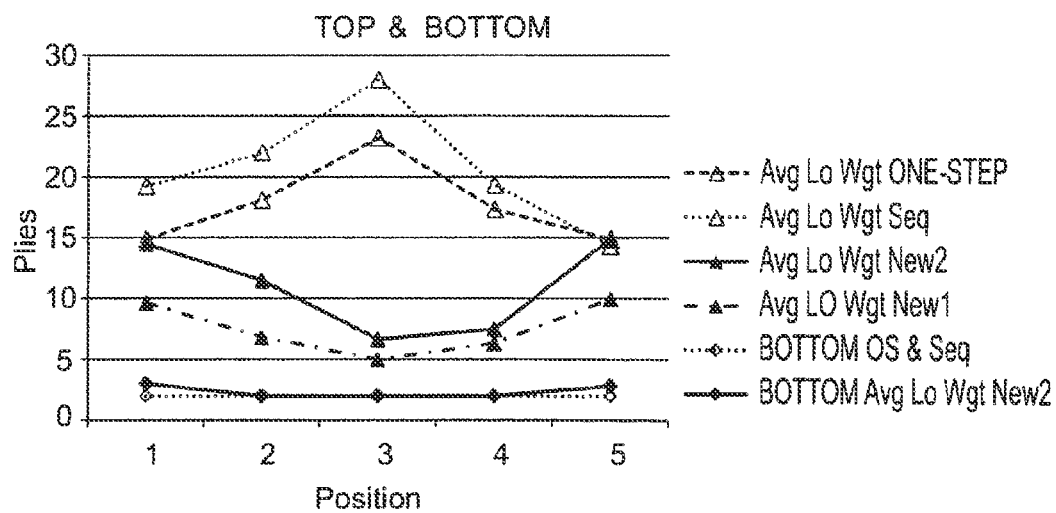
FIG. 30 is an illustration of a graph of data and information from Table 7.

FIG. 30 shows the Plies averages among the respective Front, Middle and Back row averaged values for each Lo Wgt sample for the Top and Bottom regions. This data is presented in Table 7. This Figure, like FIG. 29 for the Hi Wgt samples, clearly shows that the Plies in the center of the Top region for the invention also consistently average less than 10 stacked plies while the Plies in the Top region for the envelope fold are greater.

Figure 31:
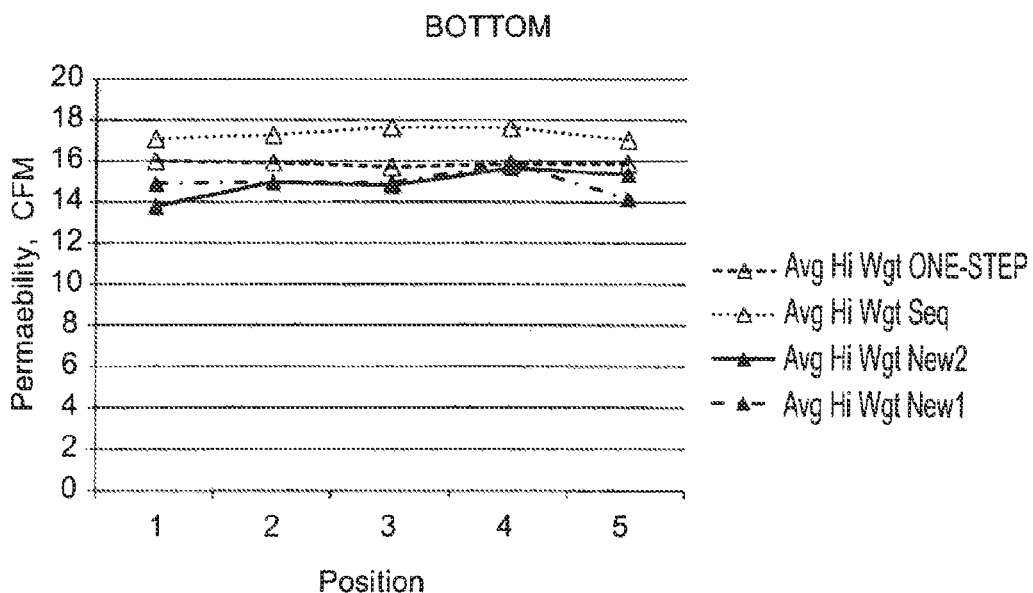
FIG. 31 is an illustration of a graph of data and information from Table 8.
Figure 33:
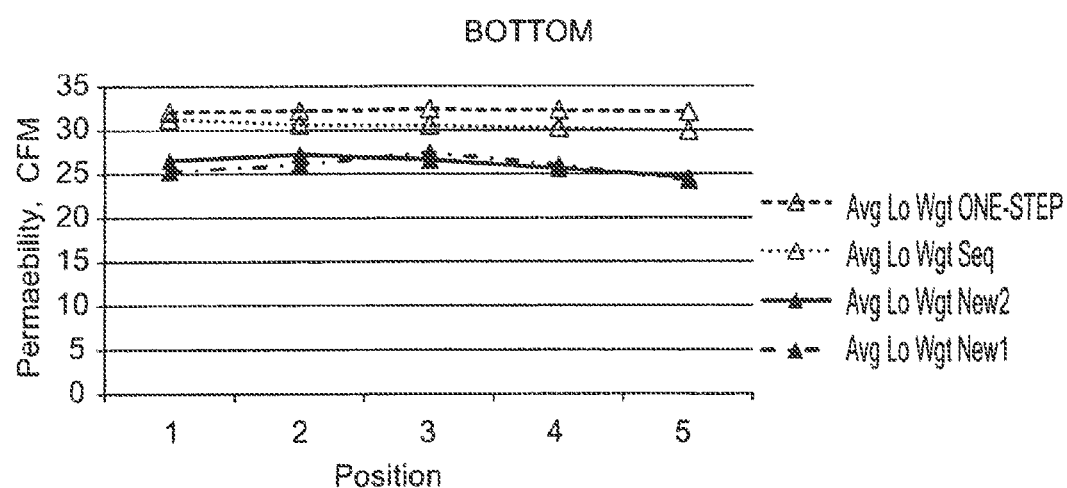
FIG. 33 is an illustration of a graph of data and information from Table 10.
Figure 35:
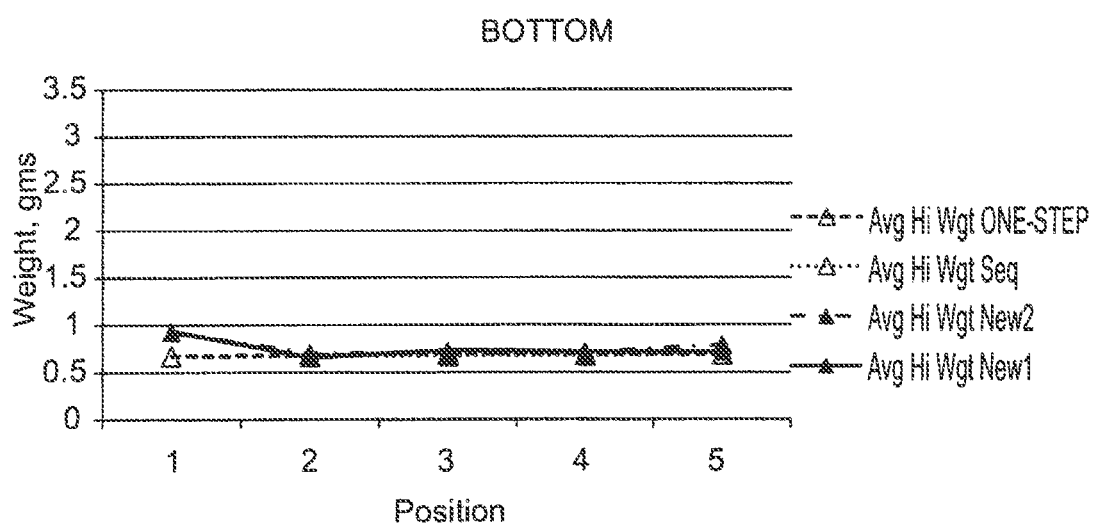
FIG. 35 is an illustration of a graph of data and information from Table 12.
Figure 36:
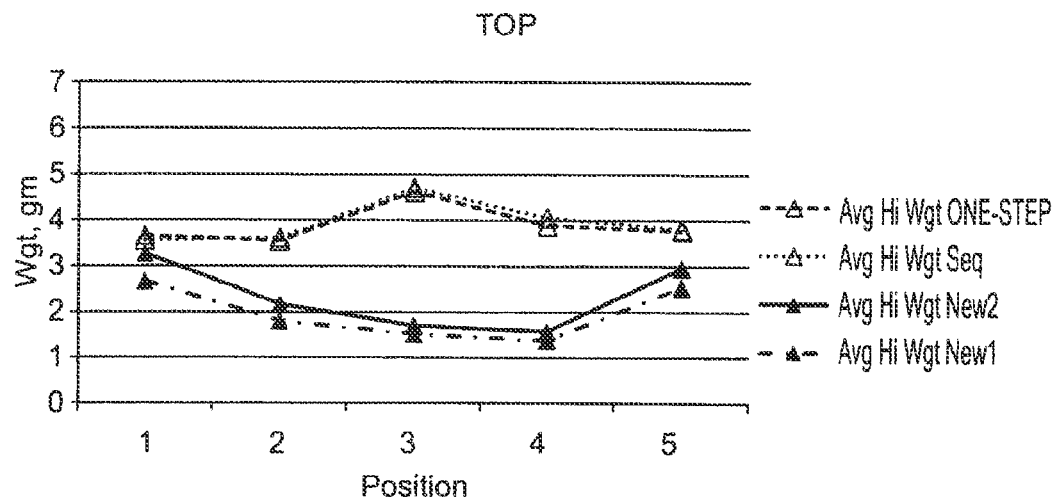
FIG. 36 is an illustration of a graph of data and information from Table 13.
Figure 37:
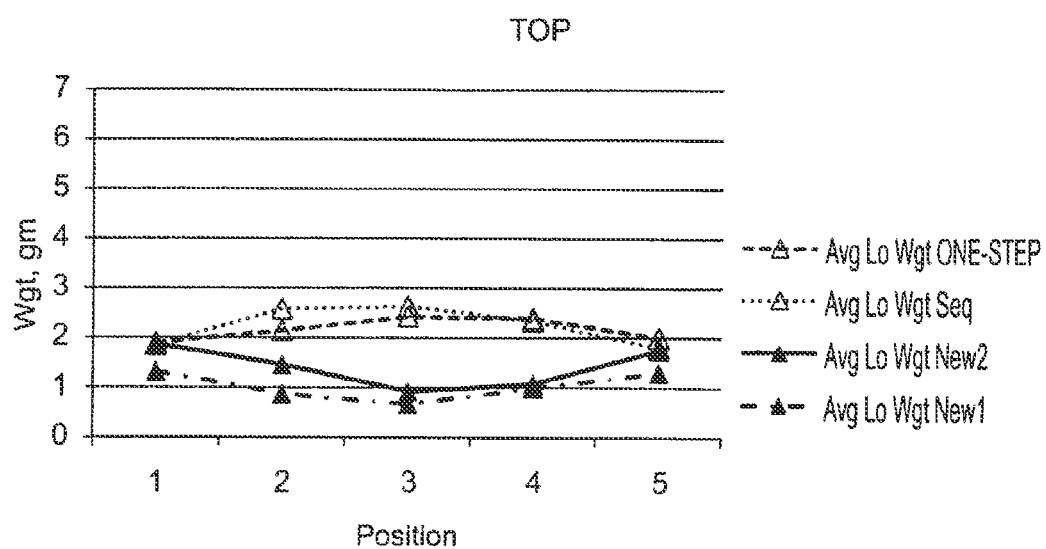
FIG. 37 is an illustration of a graph of data and information from Table 14.
Figure 38:
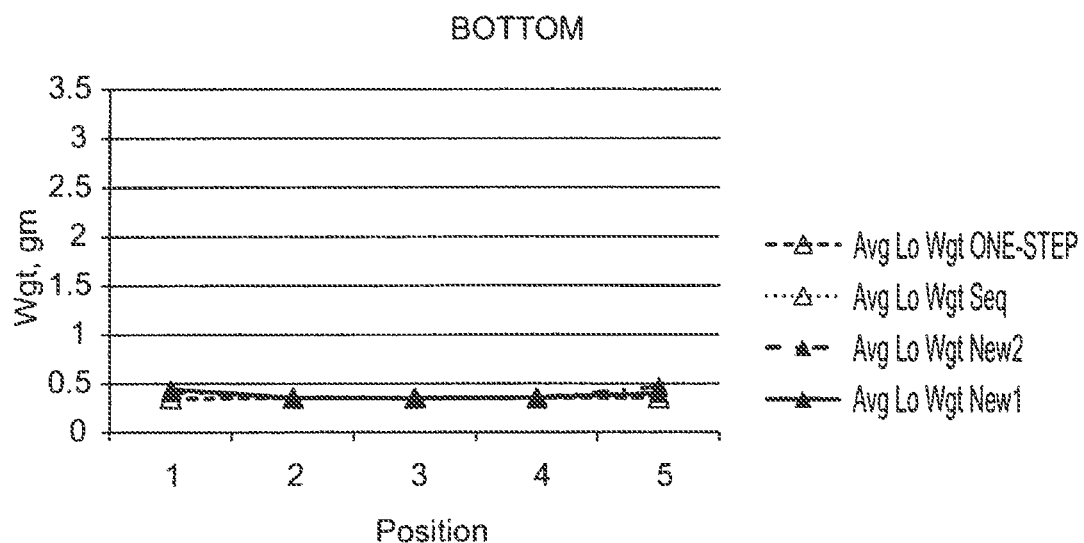
FIG. 38 is an illustration of a graph of data and information from Table 15.
Figure 39:
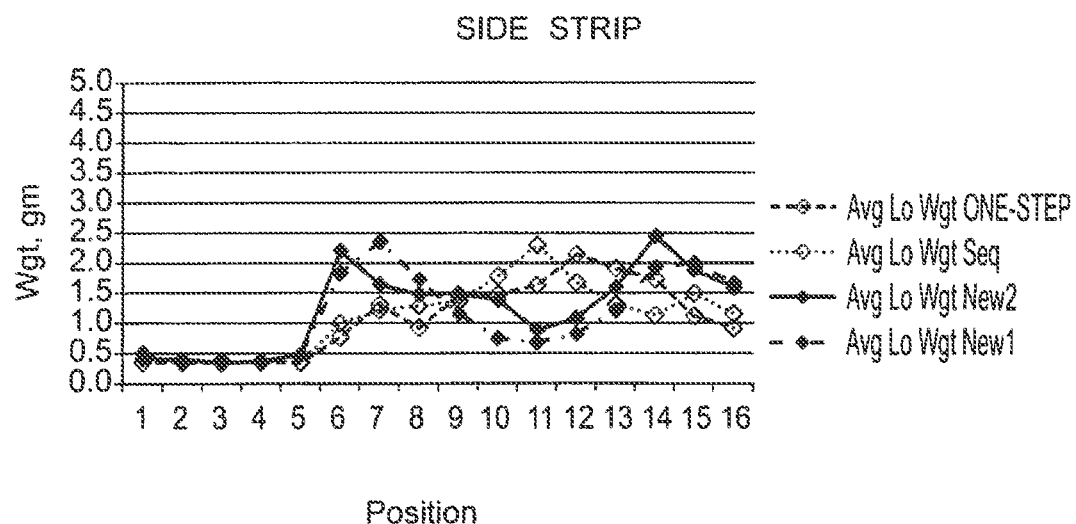
FIG. 39 is an illustration of a graph of data and information from Table 16.
Figure 40:
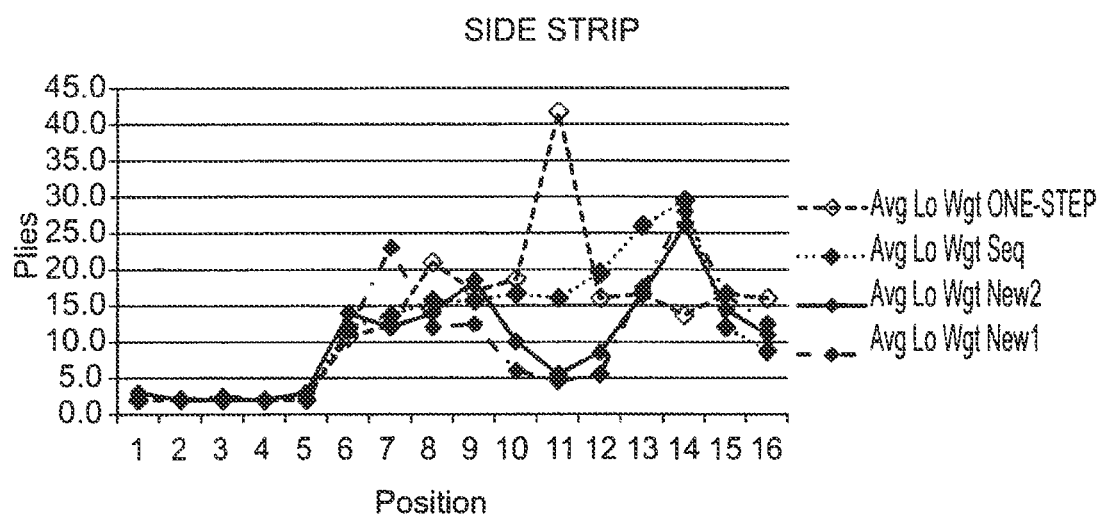
FIG. 40 is an illustration of a graph of data and information from Table 17.
Figure 41:
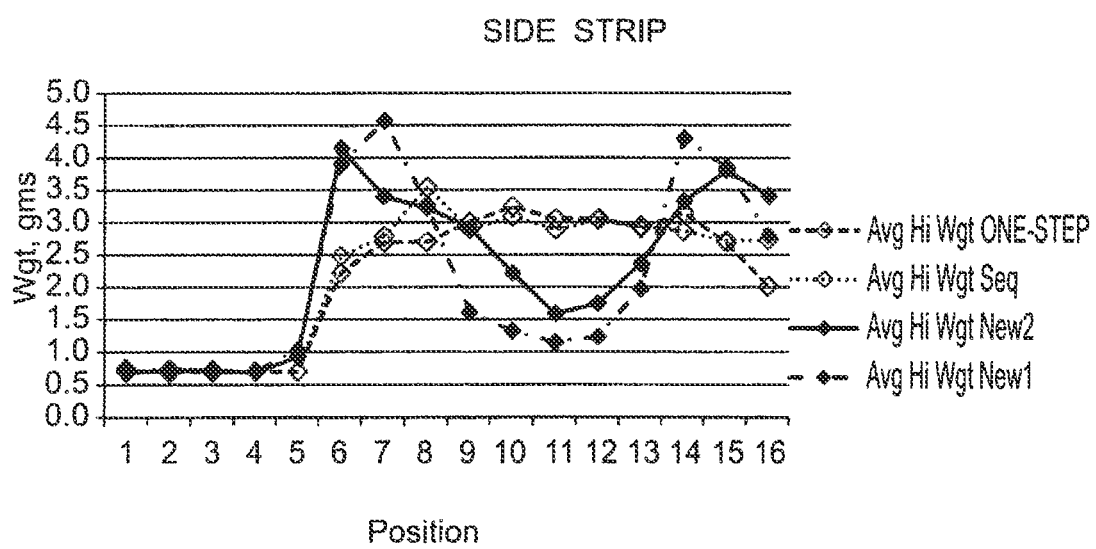
FIG. 41 is an illustration of a graph of data and information from Table 18.
Figure 42:
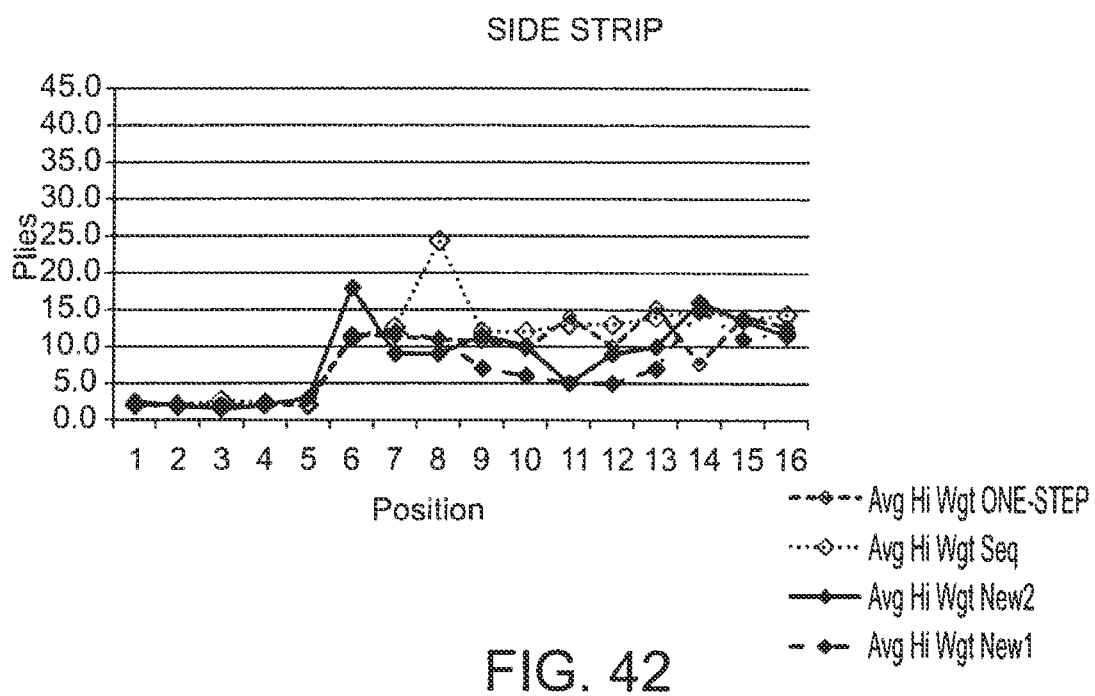
FIG. 42 is an illustration of a graph of data and information from Table 19.

FIGS. 31 and 33 show the general uniformity of Permeability through the Bottom regions for Hi Wgt and Lo Wgt samples and the differences are insignificant and are attributed to the presence (or absence) of reinforcement panels for the New1 and New2 samples, corresponding Wgt variations as respectively shown in FIGS. 35 and 38, and the inherent single ply permeability and basis weight variability as evidenced by Table 2.

Figure 32:
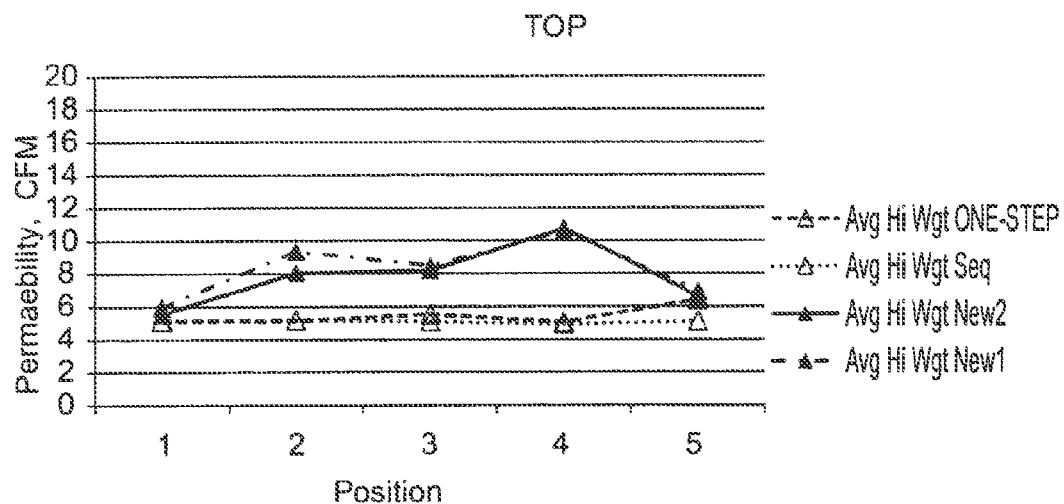
FIG. 32 is an illustration of a graph of data and information from Table 9.
Figure 34:
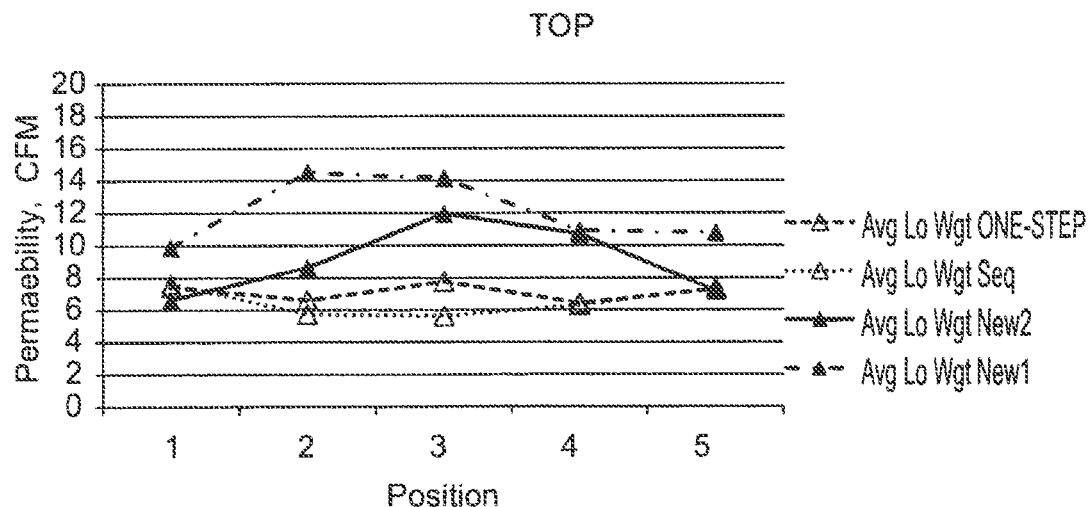
FIG. 34 is an illustration of a graph of data and information from Table 11.

FIGS. 32 and 34 show greater permeability in the central area of the Top region for the New1 and New2 samples compared to the other samples. This difference is attributed to the fewer Plies for New1 and New2 versus the other samples as respectively shown in FIGS. 29 and 30 and their corresponding Wgt values of FIGS. 37 and 36.

FIGS. 39-42 indicate the relationship between Plies and Wgt contributions and a greater concentration of Plies for New1 and New2 samples in the 5 to 9 positions and the 12 to 15 positions unlike the other samples.

Example 4

Testing of multi-panel sterilization assemblies were conducted using the Exposure Chamber Method outline by Dunkelberg H., Schmelz, U., Determination of the Efficacy of Sterile Barrier Systems Against Microbial Challenges During Transport and Storage, Infect. Control Hosp. Epidemiol. 2009; 30:179-183. The aim of this testing was to determine the microbial barrier effectiveness of the multi-panel sterilization assemblies in comparison to the current sterilization wrap product. Each prototype was tested 10 times. One set of prototypes were prepared in which the barrier panel was constructed of two plies of KC200 material. Another set of prototypes was constructed of two plies of KC400 material. These prototypes had dimensions as generally set forth in Example 2 and were used for the small tray size noted below. Proportionally larger prototypes were used for the large tray size noted below.

The size of the trays used was 250 mm×240×50 mm (small tray size) and 480 mm×24 mm×50 mm (large tray size). The trays were loaded with thermo-resistant dishes (140 mm×20 mm) filled with nutrient agar (CASO agar, Oxoid) prior to sterilization. For the large trays 2 dishes with culture medium were used.

Control samples were wrapped using KC 200 and K-C 400 KimGuard® One-Step® wrap using the conventional envelope fold technique. Double paper sheet packaging that are conventionally used as sterilization wrap were also used as control. Two wrapped trays of each prototype were prepared for 1 test run. In total 5 runs were done. The wrapped trays were positioned in shelves and then sterilized at 118° C. for 25 minutes (steam sterilization).

Using the exposure chamber method, the wraps were exposed to about 24 periodic atmospheric pressure changes of 70 hPa after sterilization and to an airborne bacteria challenge of *Micrococcus luteus* of about 5×106 to 5×107 cfu (colony forming units) per $m^3$. The microbial aerosol in the exposure chamber was produced by a nebulizer. As specified by the manufacturer, the median diameter of particles was 3.9 µm. The atmospheric pressure changes, the temperatures and the humidity were monitored continuously by an electronic data logger. Using an air sampler (impinger), samples of air were taken continuously by a vacuum pump in order to determine the mean airborne microbial concentration in the chamber. 5 uncovered settle plates with nutrient agar were placed as controls in the chamber to detect surface microbial load. After the exposure, the test items were incubated at 37° for 72 hours and then examined for colony growth. 5 runs were needed to test each prototype 10 times. The effectiveness of the microbial barrier was expressed as the logarithmic reduction value (LRV) and percent reduction. The tested prototypes and KimGuard® wrap controls showed no growth on the dishes with nutrient agar after incubation. The calculated LRV's of the microbial barrier of the examined concepts for terminally sterilized products were >6.09, that corresponds to a microbial reduction of >99.99992%.

Using the exposure chamber method, the different tested prototypes of wrapping material and KimGuard® wrap controls showed no bacterial recontamination after sterilization and exposure to airborne bacteria. The barrier efficiency was >99.99992%. 6 out of 10 tested double paper sheet packaging showed recontamination. A LRV of 3.90 and a microbial reduction of 99.987% were obtained as results for the paper sheet packaging.

Thus, exemplary embodiments of the invention are presented herein; however, the invention may be embodied in a variety of alternative forms, as will be apparent to those skilled in the art. To facilitate understanding of the invention, and provide a basis for the claims, various figures are included in the description. The figures are not drawn to scale and related elements may be omitted so as to emphasize the novel features of the invention. Structural and functional details depicted in the figures are provided for the purpose of teaching the practice of the invention to those skilled in the art and are not intended to be considered limitations. Directional terms such as left, right, front or rear are provided to assist in the understanding of the invention and are not intended to be considered as limitations.

While particular embodiments of the present invention have been described herein; it will be apparent to those skilled in the art that alterations and modifications may be made to the described embodiments without departing from the scope of the appended claims.

What is claimed is:

1. A disposable flexible multi-panel sterilization assembly comprising:
    a barrier panel comprising a permeable sheet material having barrier properties, the barrier panel including:
        a first surface and a second opposing surface,
        a first end generally defining a pre-determined fold line,
        a second end opposite the first end,
        a first edge that is generally perpendicular to the pre-determined fold line,
        a second edge that is generally opposite the pre-determined fold line, and
        a third edge that is generally perpendicular to the pre-determined fold line, the barrier panel having a having a width that is the distance from the first edge to the third edge and a length that is the distance from the first end to the second end, the barrier panel having a midpoint along the length and extending between the first edge and the third edge to generally delineate the barrier panel into a content receiving region extending from the pre-determined fold line to the midpoint and a content covering region extending from the midpoint to the second edge;
    a panel attachment means between the pre-determined fold line and the midpoint of the barrier panel and at or near the first edge or the third edge; the panel attachment means being joined to the barrier panel at a pre-determined position to identify the barrier panel's content receiving region and further to join the barrier panel's first edge and third edge to each other or to a portion of the content covering region after the barrier panel has been folded at or near its midpoint such that its second end is brought near its first end; and
    a fold protection panel in juxtaposed communication with the barrier panel, the fold protection panel comprising a permeable sheet material, the fold protection panel including:
        a proximal end generally adjacent the pre-determined fold line,
        a distal end generally opposite the proximal end; and
        at least a first edge and a second edge extending from the proximal end to the distal end, the fold protection panel having a width that is the distance from the first edge to the second edge and a length that is the distance from the proximal end to the distal end, such that, after the barrier panel has been folded at or near the barrier panel's midpoint so the barrier panel's second end is brought near its first end and its first and third edges are joined to each other or to its content covering region to form a package, the fold protection panel is configured to fold at or near the pre-determined fold line to cover at least the first edge and the third edge of the folded barrier panel,
    wherein the permeable sheet material having barrier properties comprises multiple layers or plies of a nonwoven laminate material and the permeability of the barrier panel is from about 10 cubic feet per minute to about 30 cubic feet per minute when determined generally in accordance with ISO 9237:1995.

2. The sterilization assembly of claim 1, wherein the barrier panel has a fourth edge.

3. The sterilization assembly of claim 2, wherein the barrier panel includes a fifth edge.

4. The sterilization assembly of claim 1, wherein the panel attachment means is at or near both the first edge and the third edge of the barrier panel.

5. The sterilization assembly of claim 4, wherein the panel attachment means is located at and extends from the first edge and the third edge of the barrier panel.

6. The sterilization assembly of claim 1, wherein the panel attachment means is selected from adhesive tape, double-sided adhesive tape, cohesive materials, hook and loop fastening systems, mechanical fastening systems, snaps, clips, magnets, catches, slots and tabs, and combinations thereof.

7. The sterilization assembly of claim 6, wherein the panel attachment means further includes a length of fabric having an end or portion joined to the barrier panel.

8. The sterilization assembly of claim 1, wherein the nonwoven laminate material comprising a layer of spunbonded filaments, a layer of meltblown fibers, and a layer of spunbonded filaments.

9. The sterilization assembly of claim 1, wherein the sterilization assembly further includes at least one pull tab extending from the second end of the barrier panel.

10. The sterilization assembly of claim 1, wherein the fold protection panel has at least a third edge located at or along its distal end.

11. The sterilization assembly of claim 1, wherein the fold protection panel has barrier properties.

12. The sterilization assembly of claim 1, wherein the sterilization assembly further comprises discrete reinforcement elements in the content receiving region that define an area for receiving content to be sterilized.

13. The sterilization assembly of claim 12, wherein the reinforcement elements comprise a layer of material are selected from fibrous webs, impermeable films, permeable or porous films, apertured films, foams, foils and combinations thereof.

14. The sterilization assembly of claim 1, wherein the sterilization assembly further comprises indicia or instructions on the sterilization assembly to inform the proper folding of the assembly into a package.

15. The sterilization assembly of claim 1, wherein the surface area of the content receiving region is between about 25 percent to about 49 percent of the total surface area of the barrier panel.

16. A disposable flexible multi-panel sterilization assembly comprising:
    a barrier panel comprising a permeable nonwoven sheet material having barrier properties, the barrier panel including:
        a first surface and a second opposing surface,
        a first end generally defining a pre-determined fold line,
        a second end opposite the first end,
        a first edge that is generally perpendicular to the pre-determined fold line,
        a second edge that is generally parallel to the pre-determined fold line, and
        a third edge that is generally perpendicular to the pre-determined fold line, and
        a fourth edge located between the second edge and the third edge; the barrier panel having a width that is the distance from the first edge to the third edge and an apex or vertex defined by the second edge and fourth edge; a length that is the distance from the first end to the second end, the barrier panel having a midpoint along the length and extending between the first edge and the third edge to generally delineate the barrier panel into a content receiving region extending from the pre-determined fold line to the midpoint and a content covering region extending from the midpoint to the second edge;

at least one pull tab extending from the second end of the barrier panel;

a panel attachment means between the pre-determined fold line and the midpoint of the barrier panel and at or near the first edge or the third edge; the panel attachment means being joined to the barrier panel at a pre-determined position to identify the barrier panel's content receiving region and further to join the barrier panel's first edge and third edge to each other or to a portion of the content covering region after the barrier panel has been folded at or near its midpoint such that its second edge is brought near its first end; and a fold protection panel in juxtaposed communication with the barrier panel, the fold protection panel comprising a permeable nonwoven sheet material, the fold protection panel including:

a proximal end generally adjacent the pre-determined fold line, a distal end generally opposite the proximal end; and at least a first edge and a second edge extending from the proximal end to the distal end, the fold protection panel having a width that is the distance from the first edge to the second edge and a length that is the distance from the proximal end to the distal end, such that, after the barrier panel has been folded at or near its midpoint so its second end is brought near its first end and its first and third edges are joined to each other or to its content covering region to form a package, the fold protection panel is configured to fold at or near the pre-determined fold line to cover at least the first edge and the third edge of the folded barrier panel.

\* \* \* \* \*